United States Patent
Hochedlinger et al.

(10) Patent No.: US 8,603,818 B1
(45) Date of Patent: *Dec. 10, 2013

(54) TGF-BETA RECEPTOR INHIBITORS TO ENHANCE DIRECT REPROGRAMMING

(71) Applicant: The General Hospital Corporation, Boston, MA (US)

(72) Inventors: Konrad Hochedlinger, Boston, MA (US); Matthias Stadtfeld, New York, NY (US)

(73) Assignee: The General Hospital Corporation, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/626,575

(22) Filed: Sep. 25, 2012

Related U.S. Application Data

(63) Continuation of application No. 12/547,022, filed on Aug. 25, 2009, now Pat. No. 8,298,825.

(60) Provisional application No. 61/091,574, filed on Aug. 25, 2008.

(51) Int. Cl.
*C12N 5/00* (2006.01)
*C12N 5/02* (2006.01)

(52) U.S. Cl.
USPC ............................. 435/377; 435/375; 435/325

(58) Field of Classification Search
USPC .......................................... 435/377, 375, 325
See application file for complete search history.

(56) References Cited

U.S. PATENT DOCUMENTS

2011/0104125 A1 * 5/2011 Yu ................................ 424/93.7

FOREIGN PATENT DOCUMENTS

WO    WO 2009/117439 A2    9/2009

OTHER PUBLICATIONS

Aoi, T. et al., Science, 321:699-702 (2008). "Generation of pluripotent stem cells from adult mouse liver and stomach cells."
Cowan, C. et al., Science, 309:1369-1373,(2005). "Nuclear reprogramming of somatic cells after fusion with human embryonic stem cells."
Eminli, S. et al., Stem Cells, 26:2467-2474 (2008). Reprogramming of neural progenitor cells into induced pluripotent stem cells in the absence of exogenous Sox2 expression.
Feng, B. et al., Nature Cell Biology 11(2):197-cells with orphan nuclear receptor Essrb.
Hanna, J. et al., Cell, 250-264 (2008). "Direct reprogramming of terminally differentiated mature B lymphocytes to pluripotency."
Hochedlinger K. et al., Nature, 441:1061-1067 (2006). "Nuclear reprogramming and pluripotency."
Huangfu, D. et al., Nature Biotechnology, 26(11):1269-1275 (2808). "Induction of pluripotent stem cells from primary human fibroblasts with only Oct4 and Sox2."
Jaenisch, R. et al. Cell 132:567-582, 2008. "Stem Cells, the Molecular Circuitry of Pluripotency and Nuclear Reprogramming."
Marson, A. et al., Cell Stem Cell, 3:132-135 (2008). "Wnt signaling promotes reprogramming of somatic cells to pluripotency."
Shi, Y. et al. Cell. 113:685-700, 2003. "Mechanisms of TGF-Beta Signaling from Cell Membrane to the Nucleus."
Shi, Y. et al., Cell Stem Cell, 3:568-574 (2008). "Induction of pluripotent stem cells from mouse embryonic fibroblasts by Oct4 and Klf4 with small-molecule compounds."
Stadtfeld, M. et al., Current Biology, 18:890-894 (2008). "Reprogramming of pancreatic beta cells into induced pluripotent stem cells."
Tada, M. et al., Current Biology, 11:1553-1558 (2001) "Nuclear reprogramming of somatic cells by in vitro hybridization with ES cells."
Takahashi, K. et al., Cell, 126:663-676 (2006). "Induction of pluripotent stem cells from mouse embryonic and adult fibroblast cultures by defined factors."
Takahashi, K. et al., Cell, 131:861-872 (2007). "Induction of pluripotent stem cells from adult human fibroblasts by defined factors."
Tojo, M. et al. Cancer Sci 96(11):791-800, 2005. "The ALK-5 inhibitor A-83-01 inhibits Smad signaling and epithelial-to-mesenchymal transition by transforming growth factor-Beta".
Yamanaka, S. Cell Stem Cell 1:39-49, 2007. "Strategies and New Developments in the Generation of Patient-Specific Pluripotent Stem Cells."
Yu, J. et al., Science, 318:1917-1920 (2007). "Induced pluripotent stem cell lines derived from human somatic cells."

* cited by examiner

*Primary Examiner* — Marcia S Noble
(74) *Attorney, Agent, or Firm* — David S. Resnick; Mark J. FitzGerald; Nixon Peabody LLP

(57) ABSTRACT

In general, iPS cells are produced by delivery of stem cell-associated genes into adult somatic cells (e.g., fibroblasts). Described herein are methods for enhancing the efficiency and rate of induced pluripotent stem cell production by treating somatic cells with a transforming growth factor-beta receptor (TGFβR) inhibitor. Also described herein are iPS cell compositions made according to the methods described herein and iPS cell compositions comprising an iPS cell in an admixture with a TGFβR inhibitor. Further described herein are kits for producing iPS cells using a TGFβR inhibitor.

12 Claims, 17 Drawing Sheets

SUMMARY OF REPLACEMENT EXPERIMENTS
O=Oct4, S=Sox2, M=cMyc, K=Klf4

| FACTOR COMBINATION | LENGTH OF DOX APPLICATION | DOX-INDEPENDENT LINE? |
|---|---|---|
| O | 16d | N |
| OS | 16d | N |
| OM | 16d | N |
| OK | 16d | N |
| SM | 16d | N |
| SK | 16d | N |
| SMK (-Oct4) | 16d | N |
| OMK (-Sox2) | 16d | Y - WITH INHIBITOR ONLY |
| OSK (-cMyc) | 8d | Y - WITH INHIBITOR ONLY |
| OSM (-Klf4) | 16d | N |
| OSMK | 8d | Y - BOTH WITH AND WITHOUT INHIBITOR |

FIG. 4

TGF-BETA RECEPTOR INHIBITORS TO ENHANCE DIRECT REPROGRAMMING

CROSS-REFERENCE TO RELATED APPLICATIONS

This application is a Continuation Application under 35 U.S.C. §120 of U.S. application Ser. No. 12/547,022 filed Aug. 25, 2009, and issued as U.S. Pat. No. 8,298,825 on Oct. 30, 2012, which claims the benefit under 35 U.S.C. 119(e) of U.S. Provisional Patent Application Ser. No. 61/091,574 filed Aug. 25, 2008, the contents of each of which are herein incorporated by reference in their entirety.

GOVERNMENT SUPPORT

This invention was made with Government support under Grant Nos. OD003166 and OD003266 awarded by the National Institutes of Health. The Government has certain rights in the invention.

SEQUENCE LISTING

The instant application contains a Sequence Listing which has been submitted in ASCII format via EFS-Web and is hereby incorporated by reference in its entirety. Said ASCII copy, created on Sep. 1, 2009, is named 20091110_SequenceListing_030258-061931.TXT and is 24,877 bytes.

FIELD OF THE INVENTION

The present invention relates to the production of induced pluripotent stem cells.

BACKGROUND

Reprogramming of cells by nuclear transfer (Wakayama et al., 1998; Wilmut et al., 1997) and cell fusion (Cowan et al., 2005; Tada et al., 2001) allows for the re-establishment of a pluripotent state in a somatic nucleus (Hochedlinger and Jaenisch, 2006). While the molecular mechanisms of nuclear reprogramming remain elusive, cell fusion experiments have implied that reprogramming factors can be identified in ES cells and be used to directly induce reprogramming in somatic cells. Indeed, a rational approach recently led to the identification of four transcription factors whose expression enabled the induction of a pluripotent state in adult fibroblasts (Takahashi and Yamanaka, 2006). Yamanaka and colleagues demonstrated that retroviral expression of the transcription factors Oct4, Sox2, c-Myc, and Klf4, combined with genetic selection for Fbx15 expression, gives rise to induced pluripotent stem (iPS) cells directly from fibroblast cultures. Fbx15-selected iPS cells contributed to diverse tissues in mid-gestation embryos, however, these embryos succumbed at mid-gestation, indicating a restricted developmental potential of iPS cells compared with ES cells. Consistent with this observation, only part of the ES cell transcriptome was expressed in iPS cells, and methylation analyses of the chromatin state of the Oct4 and Nanog promoters demonstrated an epigenetic pattern that was intermediate between that of fibroblasts and ES cells.

These observations raised three fundamental questions about the molecular and functional nature of directly reprogrammed cells: (i) can selection for a gene that is essential for the ES cell state generate pluripotent cells that are more similar to ES cells than the previously described Fbx15-selected iPS cells; (ii) does the pluripotent state of iPS cells depend on continuous expression of exogenous factors; and (iii) does transcription factor-induced reprogramming reset the epigenetic landscape of a fibroblast genome into that of a pluripotent cell.

Ectopic expression of the transcription factors Oct4, Sox2, cMyc, and Klf4, as well as variants of this factor combination, are sufficient to confer a pluripotent state upon several differentiated cell types, generating induced pluripotent stem cells (iPSCs) (Takahashi, K., and Yamanaka, S. (2006) *Cell* 126, 663-676; Takahashi, K., et al., (2007) *Cell* 131, 861-872; Yu, J., et al. (2007) *Science* 318, 1917-1920; Feng, B., et al., (2009) *Nat Cell Biol* 11, 197-203; Eminli, S., et al., (2008); Hanna, J., (2008) *Cell* 133, 250-264; Stadtfeld, M., et al., (2008) *Curr Biol* 18, 890-894; Aoi, T., et al., (2008) *Science* 321, 699-702). The derivation of iPSCs is a highly inefficient process with the underlying mechanisms largely unknown. This low efficiency argues for the existence of additional cooperative factors, whose identification is critical for understanding the process of reprogramming. Further, the therapeutic use of iPSCs relies on developing efficient non-genetic means of factor delivery, and while a handful of compounds that replace individual factors have been identified, their use yields a further reduction to the already low efficiency of reprogramming (Huangfu, D., et al., (2008) *Nat. Biotechnol.*; Shi, Y., (2008) *Cell Stem Cell* 3, 568-574; Marson, A., (2008) *Cell Stem Cell* 3, 132-135). Thus, the identification of compounds that enhance rather than solely replace the function of the reprogramming factors will be of great use.

SUMMARY OF THE INVENTION

Induced pluripotent stem cells (iPSs) are a type of pluripotent stem cell artificially derived from a somatic cell by inserting or expressing stem cell-associated genes. iPS cells are typically derived by viral delivery of stem cell-associated genes into adult somatic cells (e.g., fibroblasts). Described herein are methods for enhancing the efficiency and rate of induced pluripotent stem cell production by treating somatic cells with a transforming growth factor-beta receptor (TGFβR) inhibitor. Also described herein are iPS cell compositions comprising an iPS cell in an admixture with a TGFβR inhibitor, and kits for producing iPS cells using a TGFβR inhibitor.

One aspect described herein relates to a method for producing an induced pluripotent stem cell from a somatic cell, the method comprising: (a) treating a somatic cell to reprogram it or its progeny to a pluripotent stem cell phenotype; (b) contacting the somatic cell or its progeny with an inhibitor of the TGF-β signaling pathway; and (c) isolating a pluripotent stem cell from cells of step (b).

In one embodiment of this aspect and all other aspects disclosed herein, the somatic cell comprises a human cell. In an alternate embodiment, the cell is derived from a non-human organism, such as a non-human mammal.

In another embodiment of this aspect and all other aspects disclosed herein, treating comprises introducing a nucleic acid sequence encoding one or more transcription factors selected from the group consisting of Oct4, Sox2, c-MYC and Klf4 to a somatic cell.

In another embodiment of this aspect and all other aspects disclosed herein, the inhibitor of the TGF-β signaling pathway comprises an inhibitor of TGF-β receptor activity. In another embodiment of this aspect and all other aspects disclosed herein, the inhibitor of TGF-β receptor activity comprises an inhibitor of ALK4, ALK5, or ALK7.

In another embodiment of this aspect and all other aspects disclosed herein, the inhibitor of TGF-β receptor activity is selected from the group consisting of an antibody, a small molecule, and an RNA interference molecule.

In another embodiment of this aspect and all other aspects disclosed herein, the small molecule is selected from the group consisting of 2-(3-(6-Methylpyridin-2-yl)-1H-pyrazol-4-yl)-1,5 napththyridine, [3-(Pyridin-2-yl)-4-(4-quinoyl)]-1H-pyrazole, and 3-(6-Methylpyridin-2-yl)-4-(4-quinolyl)-1-phenylthiocarbamoyl-1H-pyrazole.

In another embodiment of this aspect and all other aspects disclosed herein, the nucleic acid sequences are comprised in a viral vector or a plasmid.

In another embodiment of this aspect and all other aspects disclosed herein, the viral vector is a retroviral vector.

In another embodiment of this aspect and all other aspects disclosed herein, production of the induced pluripotent stem cell is determined by detection of a stem cell marker.

In another embodiment of this aspect and all other aspects disclosed herein, the stem cell marker is selected from the group consisting of SSEA1, CD9, Nanog, Fbx15, Ecat1, Esg1, Eras, Gdf3, Fgf4, Cripto, Dax1, Zpf296, Slc2a3, Rex1, Utf1, and Nat1.

Another aspect described herein relates to a method for increasing the efficiency of induced pluripotent stem cell production, the method comprising: (a) treating a somatic cell to re-program it or its progeny to a pluripotent stem cell phenotype; (b) contacting the somatic cells subjected to the process of step (a) with an inhibitor of the TGF-β signaling pathway, wherein the efficiency of induced pluripotent stem cell generation is increased relative to such generation occurring without contacting.

Another aspect described herein relates to a method for increasing the rate of induced pluripotent stem cell production, the method comprising: (a) treating a somatic cell to re-program it or its progeny to a pluripotent stem cell phenotype; and (b) contacting the somatic cell with an inhibitor of the TGF-β signaling pathway, wherein the rate of induced pluripotent stem cell generation is increased relative to the rate of induced pluripotent stem cell generation occurring without contacting.

Another aspect described herein relates to an induced pluripotent stem cell composition comprising an induced pluripotent stem cell in an admixture with an inhibitor of the TGF-β signaling pathway. In one embodiment of this aspect and all other aspects described herein, the induced pluripotent stem cell composition consists essentially of an induced pluripotent stem cell in an admixture with an inhibitor of the TGF-β signaling pathway. In another embodiment of this aspect and all other aspects described herein, the induced pluripotent stem cell composition consists of an induced pluripotent stem cell in an admixture with an inhibitor of the TGF-β signaling pathway.

Another aspect described herein relates to a kit for producing induced pluripotent stem cells, the kit comprising: (a) nucleic acid sequences encoding one or more transcription factors selected from the group consisting of Oct4, Sox2, c-MYC and Klf4, (b) an inhibitor of the TGF-β signaling pathway, (c) packaging materials therefor.

Another aspect described herein relates to a cell composition derived from any combination of the methods described herein.

DEFINITIONS

The term "pluripotent" as used herein refers to a cell with the capacity, under different conditions, to differentiate to more than one differentiated cell type, and preferably to differentiate to cell types characteristic of all three germ cell layers. Pluripotent cells are characterized primarily by the ability to differentiate to more than one cell type, preferably to all three germ layers, using, for example, a nude mouse teratoma formation assay. Pluripotency is also evidenced by the expression of embryonic stem (ES) cell markers, although the preferred test for pluripotency is the demonstration of the capacity to differentiate into cells of each of the three germ layers.

The term "re-programming" as used herein refers to the process of altering the differentiated state of a terminally-differentiated somatic cell to a pluripotent phenotype.

By "differentiated primary cell" is meant any primary cell that is not, in its native form, pluripotent as that term is defined herein. It should be noted that placing many primary cells in culture can lead to some loss of fully differentiated characteristics. However, simply culturing such cells does not, on its own, render them pluripotent. The transition to pluripotency requires a re-programming stimulus beyond the stimuli that lead to partial loss of differentiated character in culture. Re-programmed pluripotent cells also have the characteristic of the capacity of extended passaging without loss of growth potential, relative to primary cell parents, which generally have capacity for only a limited number of divisions in culture.

As used herein, the term "TGF-β signaling pathway" is used to describe the downstream signaling events attributed to TGF-β and TGF-β like ligands. For example, in one signaling pathway a TGF-β ligand binds to and activates a Type II TGF-β receptor. The Type II TGF-β receptor recruits and forms a heterodimer with a Type I TGF-β receptor. The resulting heterodimer permits phosphorylation of the Type I receptor, which in turn phosphorylates and activates a member of the SMAD family of proteins. A signaling cascade is triggered, which is well known to those of skill in the art, and ultimately leads to control of the expression of mediators involved in cell growth, cell differentiation, tumorigenesis, apoptosis, and cellular homeostasis, among others. Other TGF-β signaling pathways are also contemplated for manipulation according to the methods described herein.

The term "inhibitor of the TGF-β signaling pathway" as used herein, refers to inhibition of at least one of the proteins involved in the signal transduction pathway for TGF-β. It is contemplated herein that an inhibitor of the TGF-β signaling pathway can be, for example, a TGF-β receptor inhibitor (e.g., a small molecule, an antibody, an siRNA), a TGF-β sequestrant (e.g., an antibody, a binding protein), an inhibitor of receptor phosphorylation, an inhibitor of a SMAD protein, or a combination of such agents.

In one embodiment, the TGF-β signaling pathway inhibitor comprises or consists essentially of a TGF-β receptor inhibitor. One of skill in the art can easily test a compound to determine if it inhibits TGF-β receptor signaling by assessing, for example, phosphorylation status of the receptor or expression of downstream proteins controlled by TGF-β in cultured cells and comparing the results to cells not treated with a TGF-β receptor inhibitor. An agent is determined to be a TGF-β signaling pathway inhibitor if the level of phosphorylation of the Type I TGF-β receptor in a culture of cells is reduced by at least 20% compared to the level of phosphorylation of the Type I TGF-β receptor in cells that are cultured in the absence of a TGF-β signaling pathway inhibitor; preferably the level of phosphorylation is reduced by at least 30%, at least 40%, at least 50%, at least 60%, at least 70%, at least 80%, at least 90%, at least 95%, at least 99%, or even 100% (no phosphorylation) in the presence of a TGF-β signaling pathway inhibitor.

As used herein, the term "Alk5" is used to denote a TGF-beta receptor type I having serine/threonine protein kinase activity (also referred to herein as TGFβR-1). The term "TGF-beta receptor" or "TGFβR" is used herein to encompass all three sub-types of the TGFβR family (i.e., TGFβR-1, TGFβR-2, TGFβR-3). The TGFβ receptors are characterized by serine/threonine kinase activity and exist in several different isoforms that can be homo- or heterodimeric.

An "RNA interference molecule" as used herein, is defined as any agent which interferes with or inhibits expression of a target gene or genomic sequence by RNA interference (RNAi). Such RNA interfering agents include, but are not limited to, nucleic acid molecules including RNA molecules which are homologous to the target gene or genomic sequence, or a fragment thereof, short interfering RNA (siRNA), short hairpin or small hairpin RNA (shRNA), microRNA (miRNA) and small molecules which interfere with or inhibit expression of a target gene by RNA interference (RNAi).

The term "vector" refers to a small carrier DNA molecule into which a DNA sequence can be inserted for introduction into a host cell. An "expression vector" is a specialized vector that contains the necessary regulatory regions needed for expression of a gene of interest in a host cell. In some embodiments the gene of interest is operably linked to another sequence in the vector. The term "operably linked" means that the regulatory sequences necessary for expression of the coding sequence are placed in the DNA molecule in the appropriate positions relative to the coding sequence so as to effect expression of the coding sequence. This same definition is sometimes applied to the arrangement of coding sequences and transcription control elements (e.g. promoters, enhancers, and termination elements) in an expression vector.

By "increasing the efficiency" of induced pluripotent stem cell production is meant that the percentage of reprogrammed cells in a given population is at least 5% higher in populations treated with a TGFβR inhibitor than a comparable, control treated population. It is preferred that the percentage of reprogrammed cells in a TGFβR inhibitor treated population is at least 10% higher, at least 20% higher, at least 30% higher, at least 40% higher, at least 50% higher, at least 60% higher, at least 70% higher, at least 80% higher, at least 90% higher, at least 1-fold higher, at least 2-fold higher, at least 5-fold higher, at least 10 fold higher, at least 100 fold higher, at least 1000-fold higher or more than a control treated population of comparable size and culture conditions. The term "control treated population of comparable size and culture conditions" is used herein to describe a population of cells that has been treated with identical media, viral induction, nucleic acid sequence, temperature, confluency, flask size, pH, etc., with the exception of the TGFβR inhibitor. To be clear, the only difference between a control treated population and a TGFβR inhibitor treated cell population is the condition of having been treated with a TGFβR inhibitor.

By "increasing the rate" of induced pluripotent stem cell production is meant that the amount of time for the induction of induced pluripotent stem cells is at least 2 days less in a TGFβR inhibitor treated cell population than in a control treated population of comparable size and culture conditions; preferably the time needed for pluripotent stem cell induction is at least 3 days less, at least 4 days less, at least 5 days less, at least 6 days less, at least 1 week less, at least 2 weeks less, at least 3 weeks less or more, in the presence of a TGFβR inhibitor than in a control treated population.

For simplicity, chemical moieties defined and referred to throughout can be univalent chemical moieties (e.g., alkyl, aryl, etc.) or multivalent moieties under the appropriate structural circumstances clear to those skilled in the art. For example, an "alkyl" moiety can be referred to a monovalent radical (e.g. $CH_3$—$CH_2$—), or in other instances, a bivalent linking moiety can be "alkyl," in which case those skilled in the art will understand the alkyl to be a divalent radical (e.g., —$CH_2$—$CH_2$—), which is equivalent to the term "alkylene." Similarly, in circumstances in which divalent moieties are required and are stated as being "alkoxy", "alkylamino", "aryloxy", "alkylthio", "aryl", "heteroaryl", "heterocyclic", "alkyl" "alkenyl", "alkynyl", "aliphatic", or "cycloalkyl", those skilled in the art will understand that the terms "alkoxy", "alkylamino", "aryloxy", "alkylthio", "aryl", "heteroaryl", "heterocyclic", "alkyl", "alkenyl", "alkynyl", "aliphatic", or "cycloalkyl" refer to the corresponding divalent moiety.

The term "halo" refers to any radical of fluorine, chlorine, bromine or iodine.

The term "acyl" refers to an alkylcarbonyl, cycloalkylcarbonyl, arylcarbonyl, heterocyclylcarbonyl, or heteroarylcarbonyl substituent, any of which may be further substituted by substituents. Exemplary acyl groups include, but are not limited to, ($C_1$-$C_6$)alkanoyl (e.g., formyl, acetyl, propionyl, butyryl, valeryl, caproyl, t-butylacetyl, etc.), ($C_3$-$C_6$)cycloalkylcarbonyl (e.g., cyclopropylcarbonyl, cyclobutylcarbonyl, cyclopentylcarbonyl, cyclohexylcarbonyl, etc.), heterocyclic carbonyl (e.g., pyrrolidinylcarbonyl, pyrrolid-2-one-5-carbonyl, piperidinylcarbonyl, piperazinylcarbonyl, tetrahydrofuranylcarbonyl, etc.), aroyl (e.g., benzoyl) and heteroaroyl (e.g., thiophenyl-2-carbonyl, thiophenyl-3-carbonyl, furanyl-2-carbonyl, furanyl-3-carbonyl, 1H-pyrroyl-2-carbonyl, 1H-pyrroyl-3-carbonyl, benzo[b]thiophenyl-2-carbonyl, etc.). In addition, the alkyl, cycloalkyl, heterocycle, aryl and heteroaryl portion of the acyl group may be any one of the groups described in the respective definitions.

The term "alkyl" refers to saturated non-aromatic hydrocarbon chains that may be a straight chain or branched chain, containing the indicated number of carbon atoms (these include without limitation propyl, allyl, or propargyl), which may be optionally inserted with N, O, S, SS, $SO_2$, C(O), C(O)O, OC(O), C(O)N or NC(O). For example, $C_1$-$C_6$ indicates that the group may have from 1 to 6 (inclusive) carbon atoms in it.

The term "alkenyl" refers to an alkyl that comprises at least one double bond. Exemplary alkenyl groups include, but are not limited to, for example, ethenyl, propenyl, butenyl, 1-methyl-2-buten-1-yl and the like.

The term "alkynyl" refers to an alkyl that comprises at least one triple bond.

The term "alkoxy" refers to an —O-alkyl radical.

The term "aminoalkyl" refers to an alkyl substituted with an amino.

The term "mercapto" refers to an —SH radical.

The term "thioalkoxy" refers to an —S-alkyl radical.

The term "aryl" refers to monocyclic, bicyclic, or tricyclic aromatic ring system wherein 0, 1, 2, 3, or 4 atoms of each ring may be substituted by a substituent. Exemplary aryl groups include, but are not limited to, phenyl, naphthyl, anthracenyl, azulenyl, fluorenyl, indanyl, indenyl, naphthyl, phenyl, tetrahydronaphthyl, and the like.

The term "arylalkyl" refers to alkyl substituted with an aryl.

The term "cyclyl" or "cycloalkyl" refers to saturated and partially unsaturated cyclic hydrocarbon groups having 3 to 12 carbons, for example, 3 to 8 carbons, and, for example, 3 to 6 carbons, wherein the cycloalkyl group additionally may be optionally substituted. Exemplary cycloalkyl groups include, but are not limited to, cyclopropyl, cyclobutyl, cyclopentyl, cyclopentenyl, cyclohexyl, cyclohexenyl, cycloheptyl, cyclooctyl, and the like.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2, 3, or 4 atoms of each ring may be substituted by a substituent. Exemplary heteroaryl groups include, but are not limited to, pyridyl, furyl or furanyl, imidazolyl, benzimidazolyl, pyrimidinyl, thiophenyl or thienyl, pyridazinyl, pyrazinyl, quinolinyl, indolyl, thiazolyl, naphthyridinyl, and the like.

The term "heteroarylalkyl" refers to an alkyl substituted with a heteroaryl.

The term "heterocyclyl" refers to a nonaromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2 or 3 atoms of each ring may be substituted by a substituent. Exemplary heterocyclyl groups include, but are not limited to piperazinyl, pyrrolidinyl, dioxanyl, morpholinyl, tetrahydrofuranyl, and the like.

The term "haloalkyl" refers to an alkyl group having one, two, three or more halogen atoms attached thereto. Exemplary haloalkyl groups include, but are not limited to chloromethyl, bromoethyl, trifluoromethyl, and the like.

The term "optionally substituted" means that the specified group or moiety, such as an aryl group, heteroaryl group and the like, is unsubstituted or is substituted with one or more (typically 1-4 substituents) independently selected from the group of substituents listed below in the definition for "substituents" or otherwise specified.

The term "substituents" refers to a group "substituted" on an alkyl, alkenyl, alkynyl, cycloalkyl, aryl, heterocyclyl, heteroaryl, acyl, amino group at any atom of that group. Suitable substituents include, without limitation, halo, hydroxy, oxo, nitro, haloalkyl, alkyl, alkenyl, alkynyl, alkaryl, aryl, aralkyl, alkoxy, aryloxy, amino, acylamino, alkylcarbanoyl, arylcarbanoyl, aminoalkyl, alkoxycarbonyl, carboxy, hydroxyalkyl, alkylthio, $CF_3$, N-morpholino, phenylthio, alkanesulfonyl, arenesulfonyl, alkanesulfonamido, arenesulfonamido, aralkylsulfonamido, alkylcarbonyl, acyloxy, cyano or ureido. In some embodiments, a substituent can itself be optionally substituted. In some cases, two substituents, together with the carbons to which they are attached to can form a ring.

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

3E. Pluripotency marker expression in an iPSC line made with the Alk5 inhibitor in the absence of Sox2. Colonies were analyzed after three passages without dox. (i) Nanog, (ii) Oct4, (iii), Sox2.

3F. Chimeric mice generated with OMK+inhibitor iPSC lines. iPSCs were labeled with lentivirally-delivered tdTomato, injected into diploid blastocysts, and harvested at E16.5. Three embryos are shown at identical exposures, demonstrating varying degrees of chimerism.

3G. Adult chimera (6 weeks) derived from an OMK+inhibitor iPSC line. Agouti coat color represents iPSC-derived cells.

FIG. 4. is a table depicting reprogramming of cells using different combinations of nucleic acid sequences with or without an exemplary TGF-beta inhibitor.

Figure 5:
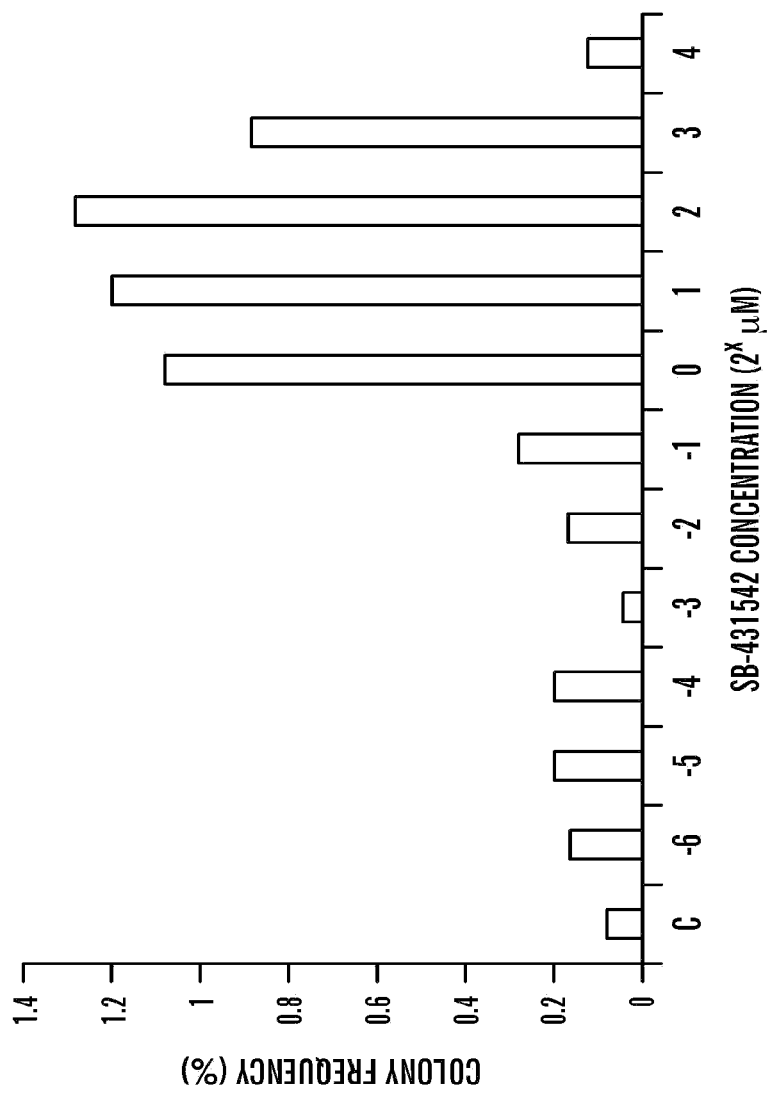

FIG. 5. Dose-Response Curve for the Alk-4/5/7 Inhibitor SB-431542.

Dox and the inhibitor were applied for 8 days in secondary STEMCCA MEFs, and colonies were quantified on day 12 based on Oct4 immunostaining.

Figure 6A:
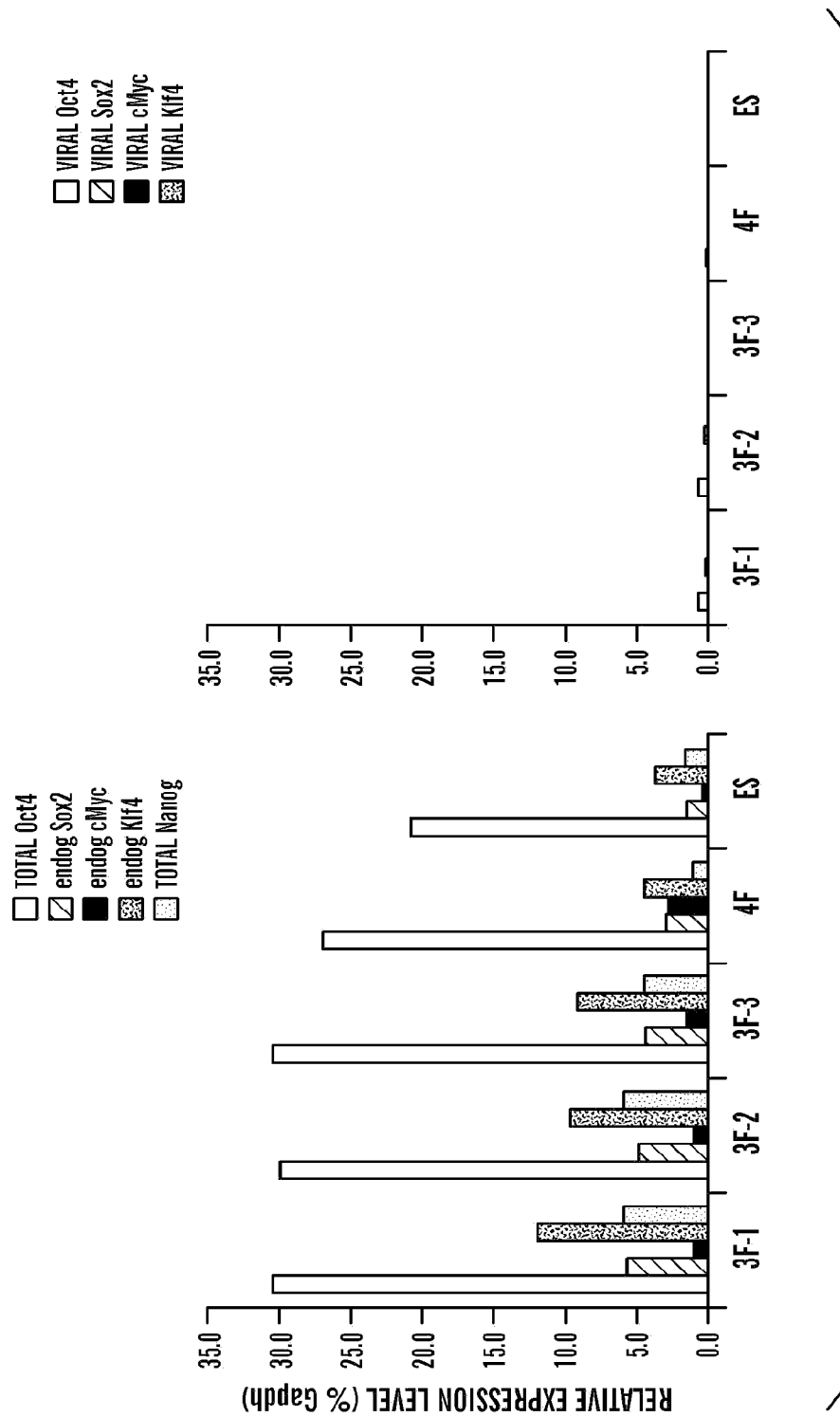

FIG. 6. Characterization of OMK+Inhibitor iPSCs.

6A. Quantitative RT-PCR data demonstrating expression of pluripotency genes (left) and silencing of viral genes (right). Expression level was normalized to Gapdh. Three 3-factor lines (OMK+inhibitor), a 4-factor line (OSMK), and a control ESC line (v6.5) were included in the analysis. Left: primers were designed to measure total Oct4 or Nanog; for Sox2, cMyc, and Klf4, primers only amplified endogenous transcripts. Right: primers were designed to only measure viral transcripts.

6B. Teratoma derived from an OMK+inhibitor iPSC line demonstrating differentiation into lineages from all three germ layers. Left, keratinized epithelium; middle, cartilage; right, gut-like epithelium.

6C. Southern blot analysis for Sox2 integrations. Three 3-factor (OMK+inhibitor) iPSC lines were analyzed (3F), as well as a control four-factor (OSMK) iPSC line, which showed an additional band in both digests, and an ESC line (v6.5), which showed no additional bands. Genomic DNA was digested with either BamHI or XhoI, and the blot was probed with a Sox2 cDNA. Panels on the right show the ethidium-bromide stained gels used for the blots.

FIG. 7. Cell Proliferation and Apoptosis During iPSC Induction.

7A. MEFs were infected with either three (OSK) or four (OSMK) factors, then induced with dox in the presence or absence of the Alk5 inhibitor (1 µM). Cells were counted at each timepoint noted, and values represent the fractional change in cell number: (fraction of starting cell number at timepoint b–fraction of starting cell number at timepoint a)/time between b and a.

7B. Annexin V and propidium iodide (PI) staining to quantify apoptosis during iPSC induction. Secondary cells carrying the polycistronic STEMCCA construct were treated with dox for 2 days in the presence or absence of the Alk5 inhibitor (1 µM), then stained and analyzed by flow cytometry. Annexin V-positive and PI-negative cells represent the fraction of living cells in the process of apoptosis.

Figure 8:
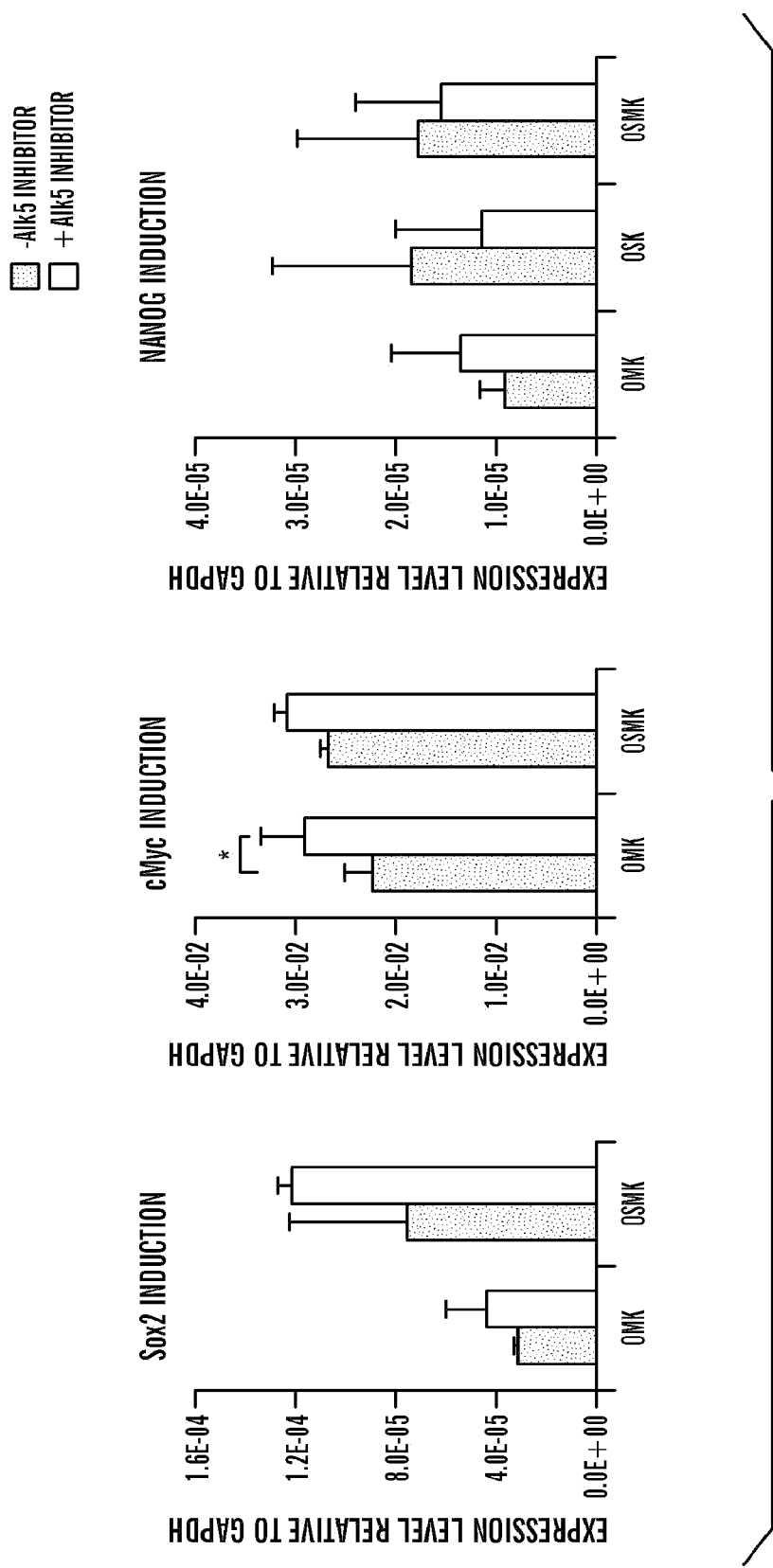

FIG. 8. Induction of Sox2, cMyc, or Nanog with Alk5 Inhibitor Treatment.

MEFs were infected with various factor combinations, then treated with dox for three days in the presence or absence of 1 mM either three (OSK) or four (OSMK) factors, then induced with dox in the presence or absence of Alk5 inhibitor (1 µM). qPCR analysis was done using primers that specifically detect endogenous Sox2 or cMyc, as well as total Nanog. Experiments were done with both biological and technical triplicates, and a Student's T-test (paired, two-tailed) was used to assess statistical significance. The Alk5 inhibitor led to a small (1.3-fold) but significant induction of cMyc in cells infected with OSK (p=0.016); No other genes showed a statistically significant change in expression (Sox2: OMK, p=0.31; OSMK, p=0.43. cMyc: OSMK, p=0.21. Nanog: OMK, p=0.25: OSK, p=0.55; OSMK, p=0.53).

DETAILED DESCRIPTION OF THE INVENTION

In general, iPS cells are produced by delivery of stem cell-associated genes into adult somatic cells (e.g., fibroblasts). Described herein are methods for enhancing the efficiency and rate of induced pluripotent stem cell production by treating somatic cells with a transforming growth factor-beta receptor (TGFβR) inhibitor. Also described herein are iPS cell compositions made according to the methods described herein and iPS cell compositions comprising an iPS cell in an admixture with a TGFβR inhibitor, and kits for producing iPS cells using a TGFβR inhibitor.

Cells

While fibroblasts are preferred, essentially any primary somatic cell type can be used. Some non-limiting examples of primary cells include, but are not limited to, epithelial, endothelial, neuronal, adipose, cardiac, skeletal muscle, immune cells, hepatic, splenic, lung, circulating blood cells, gastrointestinal, renal, bone marrow, and pancreatic cells. The cell can be a primary cell isolated from any somatic tissue including, but not limited to brain, liver, lung, gut, stomach, intestine, fat, muscle, uterus, skin, spleen, endocrine organ, bone, etc.

Where the cell is maintained under in vitro conditions, conventional tissue culture conditions and methods can be used, and are known to those of skill in the art. Isolation and culture methods for various cells are well within the abilities of one skilled in the art.

Further, the parental cell can be from any mammalian species, with non-limiting examples including a murine, bovine, simian, porcine, equine, ovine, or human cell. In one embodiment, the cell is a human cell. In an alternate embodiment, the cell is from a non-human organism such as e.g., a non-human mammal. The parental cell should not express embryonic stem cell (ES) markers, e.g., Nanog mRNA or other ES markers, thus the presence of Nanog mRNA or other ES markers indicates that a cell has been re-programmed. For clarity and simplicity, the description of the methods herein refers to fibroblasts as the parental cells, but it should be understood that all of the methods described herein can be readily applied to other primary parent cell types.

Where a fibroblast is used, the fibroblast is flattened and irregularly shaped prior to the re-programming, and does not express Nanog mRNA. The starting fibroblast will preferably not express other embryonic stem cell markers. The expression of ES-cell markers can be measured, for example, by RT-PCR. Alternatively, measurement can be by, for example, immunofluorescence or other immunological detection approach that detects the presence of polypeptides that are characteristic of the ES phenotype.

Reprogramming

The production of iPS cells is generally achieved by the introduction of nucleic acid sequences encoding stem cell-associated genes into an adult, somatic cell. In general, these nucleic acids are introduced using retroviral vectors and expression of the gene products results in cells that are morphologically and biochemically similar to pluripotent stem cells (e.g., embryonic stem cells). This process of altering a cell phenotype from a somatic cell phenotype to a stem cell-like phenotype is termed "reprogramming".

Reprogramming can be achieved by introducing a combination of stem cell-associated genes including, for example Oct3/4 (Pouf51), Sox1, Sox2, Sox3, Sox 15, Sox 18, NANOG, Klf1, Klf2, Klf4, Klf5, c-Myc, 1-Myc, n-Myc and LIN28. In general, successful reprogramming is accomplished by introducing Oct-3/4, a member of the Sox family, a member of the Klf family, and a member of the Myc family to a somatic cell. In one embodiment of the methods described herein, reprogramming is achieved by delivery of Oct-4, Sox2, c-Myc, and Klf4 to a somatic cell (e.g., fibroblast). In one embodiment, the nucleic acid sequences of Oct-4, Sox2, c-MYC, and Klf4 are delivered using a viral vector, such as an adenoviral vector, a lentiviral vector or a retroviral vector.

While it is understood that reprogramming is usually accomplished by viral delivery of stem-cell associated genes, it is also contemplated herein that reprogramming can be induced using other delivery methods.

The efficiency of reprogramming (i.e., the number of reprogrammed cells) can be enhanced by the addition of various small molecules as shown by Shi, Y., et al (2008) *Cell-Stem Cell* 2:525-528, Huangfu, D., et al (2008) *Nature Biotechnology* 26(7):795-797, Marson, A., et al (2008) *Cell-Stem Cell* 3:132-135, which are incorporated herein by reference in their entirety. It is contemplated that the methods described herein can also be used in combination with a single small molecule (or a combination of small molecules) that enhances the efficiency of induced pluripotent stem cell production. Some non-limiting examples of agents that enhance reprogramming efficiency include soluble Wnt, Wnt conditioned media, BIX-01294 (a G9a histone methyltransferase), PD0325901 (a MEK inhibitor), DNA methyltransferase inhibitors, histone deacetylase (HDAC) inhibitors, valproic acid, 5'-azacytidine, dexamethasone, suberoylanilide, hydroxamic acid (SAHA), and trichostatin (TSA), among others. It is also contemplated herein that inhibitors of the TGF-β signaling pathway either alone or in combination with another small molecule (or combination of small molecules) can be used to replace one or more of the reprogramming factors used for the production of iPS cells.

TGF-β Receptors

The TGF-β receptors contemplated for use in the methods described herein can be any TGF-β receptor including those from the Activin-like kinase family (ALK), the Bone Morphogenic Protein (BMP) family, the Nodal family, the Growth and Differentiation Factors family (GDF), and the TGF-β receptor family of receptors. TGF-β receptors are serine/threonine kinase receptors that effect various growth and differentiation pathways in the cell.

In one embodiment, the TGF-β receptor useful for the methods described herein is an ALK4, ALK5, or ALK7 receptor. In another embodiment, the TGF-β receptor inhibited by the methods described herein is an ALK5 receptor. In another embodiment, downstream effectors of any of the aforementioned TGF-beta receptor signaling pathways can be targeted directly to effect cell reprogramming with the methods described herein.

If desired, one of skill in the art can locate the protein sequence of any of the TGF-β receptors by simply searching "transforming growth factor beta receptor" in a protein sequence database such as NCBI. Some non-limiting examples of protein sequence accession numbers for TGF-β receptors are P36897.1 (SEQ ID NO:1), Q5T7S2 (SEQ ID NO:2), Q6IR47 (SEQ ID NO:3), P37173 (SEQ ID NO:4), Q6A176 (not shown), Q706C0 (not shown), Q706C1 (not shown), and Q03167.2 (SEQ ID NO:5), among others.

TGF-β1 is a prototypic member of a family of cytokines including the TGF-βs, activins, inhibins, bone morphogenetic proteins and Mullerian-inhibiting substance, that signal through a family of single transmembrane serine/threonine kinase receptors. These receptors can be divided into two classes, the type I or activin like kinase (ALK) receptors and type H receptors. The ALK receptors are distinguished from the type II receptors in that the ALK receptors (a) lack the serine/threonine rich intracellular tail, (b) possess serine/threonine kinase domains that are very homologous between type I receptors, and (c) share a common sequence motif called the GS domain, consisting of a region rich in glycine and serine residues. The GS domain is at the amino terminal end of the intracellular kinase domain and is critical for activation by the type II receptor. Several studies have shown that TGF-β signalling requires both the ALK and type H receptors. Specifically, the type II receptor phosphorylates the GS domain of the type I receptor for TGF-β, ALK5, in the presence of TGF-β. The ALK5, in turn, phosphorylates the cytoplasmic proteins Smad2 and Smad3 at two carboxy terminal serines. The phosphorylated Smad proteins translocate into the nucleus and activate genes that contribute to e.g., the production of extracellular matrix.

Activin ligands transduce signals in a manner similar to TGF-β ligands. Activins bind to and activate ALK receptors, which in turn phosphorylate Smad proteins such as Smad2 and Smad3. The consequent formation of a hetero-Smad complex with Smad4 results in the activin-induced regulation of gene transcription.

Smad proteins are exemplary downstream signal transduction factors in the TGF-beta pathway and therefore can be activated or inhibited directly to effect reprogramming (i.e., by treating a cell with an activator or inhibitor of a Smad protein). In one embodiment, an activator of Smad 7 is used to effect cell reprogramming. In another embodiment, inhibition of Smad 2, 3, or 5 is used to effect cell reprogramming.

TGF-Beta Receptor (TGFβR) Inhibitors

As used herein, the term "TGF-β signaling inhibitor" (also referred to as TGF-β signal transduction inhibitor) is a compound that inhibits TGF-β signal transduction by inhibiting any of the factors constituting the TGF-β signal transduction system pathway, such as TGF-β ligand, TGF-β Type I receptors, TGF-β Type II receptors, TGF-βType III receptors (β-glycan and endoglin), soluble forms of the TGF-β receptors, Smad proteins (1-8), antibodies against receptors and ligands implicated in the signaling pathway, nucleic acid based molecules (e.g., antisense, siRNA, aptamers and ribozymes) targeting the pathway members, or a combination thereof.

An "inhibitor" of a TGFβR, as the term is used herein, can function in a competitive or non-competitive manner, and can function, in one embodiment, by interfering with the expression of the TGFβR polypeptide. A TGFβR inhibitor includes any chemical or biological entity that, upon treatment of a cell, results in inhibition of a biological activity caused by activation of the TGFβR in response to binding of its natural ligand. While any TGF-β signaling pathway inhibitor can potentially be used in the methods described herein, it is preferable that a TGF-β signaling pathway inhibitor is either selective for, or specific for, a member of the TGF-β signaling pathway. By "specific" is meant that at the dose necessary for the inhibiting agent to inhibit the TGF-β signaling pathway, the inhibiting agent does not have any other substantial pharmacological action in the cell or host. By "selective" is meant that the dose of the inhibitor necessary for inhibition of the TGF-β signaling pathway is at least 2-fold lower than the dose necessary for activation or inhibition of another pharmacological action as measured by the $ED_{50}$ or $EC_{50}$ of the agent for each pharmacological effect; preferably the dose of inhibitor necessary for TGF-β pathway inhibition is at least 5-fold lower, at least 10 fold lower, at least 20-fold lower, at least 30-fold lower, at least 40-fold lower, at least 50-fold lower, at least 60-fold lower, at least 70-fold lower, at least 80-fold lower, at least 90-fold lower, at least 100-fold lower, at least 500-fold lower, at least 1000 fold lower or more, than the dose necessary for another pharmacological action. Thus, to be clear, the agents useful for the methods described herein primarily inhibit the TGF-β signaling pathway with only minor, if any, effects on other pharmacological pathways, and the dose used for inhibition of the TGF-β signaling pathway is sub-clinical or sub-threshold for other pharmacological responses.

Such an inhibitor can act by binding to the intracellular domain of the receptor and blockade of its serine/threonine kinase activity (e.g., ATP binding site). Alternatively, such an inhibitor can act by occupying or sterically hindering the ligand binding site (or a portion thereof) of the TGFβR, thereby rendering the receptor inaccessible to binding by the natural ligand, which prevents activation by that ligand. In addition, the TGFβR inhibitor can also bind to a non-ligand binding site and, for example, produce a conformational shift in the TGFβR, such that a ligand of the TGFβR can no longer access the binding site. An inhibitor can be, for example, a competitive inhibitor, a non-competitive inhibitor, an inverse agonist or a partial agonist of the TGFβR.

Alternatively, such an inhibitor can act by modulating the heterodimerization of TGFβR polypeptides, the interaction of TGFβR with other proteins, or the ubiquitination or endocytic degradation of the receptor. TGFβR inhibitors, include, but are not limited to small molecules, antibodies or antigen-binding antibody fragments, antisense constructs, siRNAs and ribozymes.

The receptor activity of a TGF-β receptor can be measured, for example, as described by Laping, N.J., et al (2002) *Molecular Pharmacology* 62(1):58-64, which is herein incorporated by reference in its entirety. In addition, the dose-response curve for a TGF-β receptor inhibitor can be determined by measuring TGF-β receptor activity over a variety of inhibitor concentrations using the method of Laping, N.J., et al (2002).

Small Molecule Inhibitors

As used herein, the term "small molecule" refers to a chemical agent which can include, but is not limited to, a peptide, a peptidomimetic, an amino acid, an amino acid analog, a polynucleotide, a polynucleotide analog, an aptamer, a nucleotide, a nucleotide analog, an organic or inorganic compound (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

Some non-limiting examples of small molecule inhibitors of TGFβRs include 24346-Methylpyridin-2-yl)-1H-pyrazol-4-yl)-1,5 napththyridine, [3-(Pyridin-2-yl)-4-(4-quinoyl)]-1H-pyrazole, and 3-(6-Methylpyridin-2-yl)-4-(4-quinolyl)-1-phenylthiocarbamoyl-1H-pyrazole, which can be purchased from Calbiochem (San Diego, Calif.). Other small molecule inhibitors include, but are not limited to, SB-431542 (see e.g., Halder et al., 2005; *Neoplasia* 7(5):509-521), SM16 (see e.g., Fu, K et al., 2008; *Arteriosclerosis, Thrombosis and Vascular Biology* 28(4):665), and SB-505124 (see e.g., Dacosta Byfield, S., et al., 2004; *Molecular Pharmacology* 65:744-52), among others.

In one embodiment, the ALK5 inhibitor 2-(3-(6-Methylpyridin-2-yl)-1H-pyrazol-4-yl)-1,5 napththyridine is used with the methods described herein. This inhibitor is also referred to herein as ALK5 inhibitor II and is available commercially from Calbiochem (Cat. No. 616452; San Diego, Calif.). In one embodiment, the inhibitor is SB 431542, an ALK-4, -5, -7 inhibitor, commercially available from Sigma (product no. 54317; Saint Louis, Mo.). SB 431542 is also referred to by the following chemical names: 4-[4-(1,3-Benzodioxol-5-yl)-5-(2-pyridinyl)-1H-imidazol-2-yl]-benzamide, 4-[4-(3,4-methylenedioxyphenyl)-5-(2-pyridyl)-1H-imidazol-2-yl]-benzamide, or 4-(5-benzol[1,3]dioxol-5-yl-4-pyridin-2-yl-1H-imidazol-2-yl)-benzamide hydrate.

Small molecules inhibitors of TGF-β signaling can be classified based on the basic scaffold of the molecule. For example, TGF-β signaling inhibitors can be based on the dihydropyrrlipyrazole-based scaffold, imidazole-based scaffold, pyrazolopyridine-based scaffold, pyrazole-based scaffold, imidazopyridine-based scaffold, triazole-based scaffold, pyridopyrimidine-based scaffold, pyrrolopyrazole-based scaffold, isothiazole-based scaffold and oxazole-based scaffold.

Inhibitors of TGF-β signaling are described in Callahan, J. F. et al., J. Med. Chem. 45, 999-1001 (2002); Sawyer, J. S. et al., J. Med. Chem. 46, 3953-3956 (20031; Gellibert, F. et al., J. Med. Chem. 47, 4494-4506 (2004); Tojo, M. et al., Cancer Sci. 96: 791-800 (2005); Valdimarsdottir, G. et al., APMIS 113, 773-389 (2005); Petersen et al. Kidney International 73, 705-715 (2008); Yingling, J. M. et al., Nature Rev. Drug Disc. 3, 1011-1022 (2004); Byfield, S. D. et al., Mol. Pharmacol., 65, 744-752 (2004); Dumont, N, et al., Cancer Cell 3, 531-536 (2003); WO Publication No. 2002/094833; WO Publication No. 2004/026865; WO Publication No. 2004/067530; WO Publication No. 209/032667; WO Publication No. 2004/013135; WO Publication No. 2003/097639; WO Publication No. 2007/048857; WO Publication No. 2007/018818; WO Publication No. 2006/018967; WO Publication No. 2005/039570; WO Publication No. 2000/031135; WO Publication No. 1999/058128; U.S. Pat. No. 6,509,318; U.S. Pat. No. 6,090,383; U.S. Pat. No. 6,419,928; U.S. Pat. No. 9,927,738; U.S. Pat. No. 7,223,766; U.S. Pat. No. 6,476,031; U.S. Pat. No. 6,419,928; U.S. Pat. No. 7,030,125; U.S. Pat. No. 6,943,191; U.S. Publication No. 2005/0245520; U.S. Publication No. 2004/0147574; U.S. Publication No. 2007/0066632; U.S. Publication No. 2003/0028905; U.S. Publication No. 2005/0032835; U.S. Publication No. 2008/0108656; U.S. Publication No. 2004/015781; U.S. Publication No. 2004/0204431; U.S. Publication No. 2006/0003929; U.S. Publication No. 2007/0155722; U.S. Publication No. 2004/0138188 and U.S. Publication No. 2009/0036382, the contents of each which are herein incorporated by reference in their entirety.

Oligonucleotide based modulators of TGF-β signaling, such as siRNAs and antisense oligonucleotides, are described in U.S. Pat. No. 5,731,424; U.S. Pat. No. 6,124,449; U.S. Publication Nos. 2008/0015161; 2006/0229266; 2004/0006030; 2005/0227936 and 2005/0287128, each of which are herein incorporated by reference in their entirety. Other antisense nucleic acids and siRNAs can be obtained by methods known to one of ordinary skill in the art.

Exemplary inhibitors of TGF-β signaling include, but are not limited to, AP-12009 (TGF-β Receptor type II antisense oligonucleotide), Lerdelimumab (CAT 152, antibody against TGF-β Receptor type II) GC-1008 (antibody to all isoforms of human TGF-β), ID11 (antibody to all isoforms of murine TGF-β), soluble TGF-β, soluble TGF-β Receptor type II, dihydropyrroloimidazole analogs (e.g., SKF-104365), tri-arylimidazole analogs (e.g., SB-202620 (4-(4-(4-fluorophenyl)-5-(pyridin-4-yl)-1H-imidazol-2-yl)benzoic acid) and SB-203580 (4-(4-Fluorophenyl)-2-(4-methylsulfinyl phenyl)-5-(4-pyridyl)-1H-imidazole)), RL-0061425, 1,5-naphthyridine aminothiazole and pyrazole derivatives (e.g., 4-(6-methyl-pyridin-2-yl)-5-(1,5-naphthyridin-2-yl)-1,3-thiazole-2-amine and 2-[3-(6-methyl-pyridin-2-yl)-1H-pyrazole-4-yl]-1,5-naphthyridine), SB-431542 (4-(5-Benzol[1,3]dioxol-5-yl-4-pyridin-2-yl-1H-imidazol-2-yl)-benzamide), GW788388 (4-(4-(3-(pyridin-2-yl)-1H-pyrazol-4-yl)pyridin-2-yl)-N-(tetrahydro-2H-pyran-4-yl) benzamide), A-83-01 (3-(6-Methyl-2-pyridinyl)-N-phenyl-4-(4-quinolinyl)-1,1-pyrazole-1-carbothioamide), Decorin, Lefty 1, Lefty 2, Follistatin, Noggin, Chordin, Cerberus, Gremlin, Inhibin, BIO (6-bromo-indirubin-3'-oxime), Smad proteins (e.g., Smad6, Smad7), and Cystatin C.

Inhibitors of TGF-β signaling also include molecules which inhibit TGF-β Receptor type I. Inhibitors of TGF-β Receptor type I are described in Byfield, S. D., and Roberts, A. B., Trends Cell Biol. 14, 107-111 (2004); Sawyer J. S. et al., Bioorg. Med. Chem. Lett. 14, 3581-3584 (2004); Sawyer, J. S. et al., J. Med. Chem. 46, 3953-3956 (2003); Byfield, S. D. et al., Mol. Pharmacol. 65, 744-752 (2004); Gellibert, F. et al., J. Med. Chem. 47, 4494-4506 (2004); Yingling, J. M. et al., Nature Rev. Drug Disc. 3, 1011-1022 (2004); Dumont, N, et al., Cancer Cell 3, 531-536 (2003); Tojo, M. et al., Cancer Sci. 96: 791-800 (2005); WO Publication No. 2004/026871; WO Publication No. 2004/021989; WO Publication No. 2004/026307; WO Publication No. 2000/012497; U.S. Pat. No. 5,731,424; U.S. Pat. No. 5,731,144; U.S. Pat. No. 7,151,169; U.S. Publication No. 2004/00038856 and U.S. Publication No. 2005/0245508, contents of all of which are herein incorporated in their entireties.

Exemplary inhibitors of TGF-β Receptor type I include, but are not limited to, soluble TGF-β Receptor type I; AP-11014 (TGF-β Receptor type I antisense oligonucleotide); Metelimumab (CAT 152, TGF-β Receptor type I antibody); LY550410; LY580276 (3-(4-fluorophenyl)-5,6-dihydro-2-(6-methylpyridin-2-yl)-4H-pyrrolo[1,2-b]pyrazole); LY364947 (4-[3-(2-Pyridinyl)-1H-pyrazol-4-yl]-quinoline); LY2109761; LY573636 (N-((5-bromo-2-thienyl)sulfonyl)-2,4-dichlorobenzamide); SB-505124 (2-(5-Benzo[1,3]dioxol-5-yl-2-tert-butyl-3H-imidazol-4-yl)-6-methylpyridine); SD-208 (2-(5-Chloro-2-fluorophenyl)-4-[(4-pyridyl)amino]pteridine); SD-093; KI2689; SM16; FKBP12 protein; 3-(4-(2-(6-methylpyridin-2-yl)H-imidazo[1,2-a]pyridin-3-yl)quinolin-7-yloxy)-N,N-dimethylpropan-1-amine; and

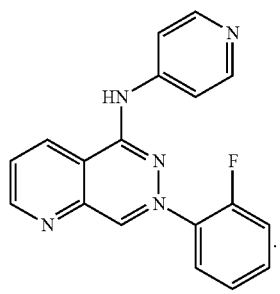

In one aspect, the TGF-β inhibitor has the structure shown in formula (I):

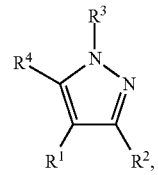

Formula (I)

wherein $R^1$ cyclyl, heterocyclcyl, aryl or heteroaryl, each of which can be optionally substituted;

$R^2$ cyclyl, heterocyclcyl, aryl or heteroaryl, each of which can be optionally substituted;

$R^3$ is H, $C_1$-$C_6$ alkyl, aryl$C_1$-$C_6$, or a nitrogen protecting group, each of which can be optionally substituted;

$R^4$ is H, optionally substituted $C_1$-$C_6$ alkyl, optionally substituted $C_2$-$C_6$ alkenyl, optionally substituted $C_2$-$C_6$ alkynyl, or $R^3$ and $R^4$ together with the atoms they are attached to form a cyclyl, heterocyclyl, aryl or heteroaryl, each of which can be optionally substituted.

In some embodiments, $R^1$ is aryl, e.g., a substituted aryl. In some embodiments, $R^1$ is substituted with two substituents. In some embodiments, $R^1$ is substituted with two substituents, which together with the carbons to which they are attached form a ring. In some embodiments, $R^1$ is a substituted phenyl. In some embodiments, $R^1$ is a nitrogen containing heteroaryl (e.g., including 1, 2, or 3 nitrogens). In some embodiments, $R^1$ is a bicyclic heteroaryl. In some embodiments, $R^1$ is a 6-6 fused heteroaryl. In some embodiments, $R^1$ is pyridyl, pyrimidyl, pyridazinyl, pyrazinyl, quinolinyl, naphthyridinyl (e.g., 1,5-naphthyridinyl), quinazolinyl, 5,6,7,8-tetrahydroquinazolinyl, 1,3-benzodioxlyl, 1,2,3-benzotriazolyl, benzoxazolyl, benzothiazolyl, 2,1,3-benzooxadiazole, imidazo[1,2-a]pyridinyl, pyrazolo[1,5-a]pyridinyl, [1,2,4]triazolo[1,5-a]pyridinyl, pyrazolo[1,5-a]pyrimidinyl, [1,2,4]triazolo[1,5-a]pyrimidinyl, [1,2,3]triazolo[1,5-a]pyrimidinyl, [1,2,4]triazolo[4,3-a]pyrimidinyl, [1,2,4]triazolo[4,3-a]pyridazinyl. In some embodiments, $R^1$ is

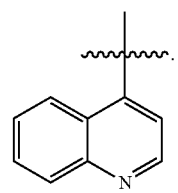 [SMILES: *c1ccnc2ccccc12]

In some embodiments, $R^1$ is

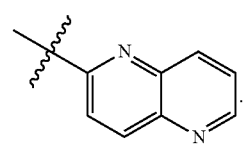 [SMILES: *c1ccc2ncccc2n1]

In some embodiments, R² is aryl, e.g., a substituted aryl. In some embodiments, R² is a nitrogen comprising heteroaryl (e.g., including 1, 2 or 3 nitrogens (e.g., 1 or 2)). In some embodiments, R² is an optionally substituted monocyclic heteroaryl (e.g., a six membered heteroaryl such as pyridyl, pyrimidyl, pyridazinyl or pyrazinyl). In some embodiments, R² is substituted. Exemplary substituents include halo, $C_1$-$C_6$ alkyl, halo$C_1$-$C_6$alkyl, $C_1$-$C_6$ alkoxy, OH, halo$C_1$-$C_6$alkoxy. In some embodiments, R² is monosubstituted. In some embodiments, R² is substituted with methyl. In one embodiment, R² is an optionally substituted pyridyl. In some embodiments, R² is

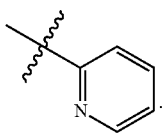

In some embodiments, R² is

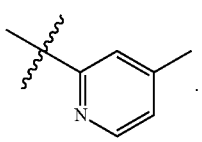

In one embodiment, R⁴ is H.

In one embodiment, the compound of formula (I) has the structure shown in formula (Ia):

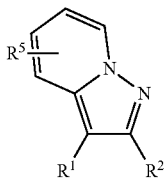

Formula (Ia), wherein R⁵ is H, benzyl, aryl, heteroaryl, $C_1$-$C_6$alkyl, alkenyl, alkynyl, halogen, amino, —C(O)-amino, —SO₂-alkyl, —O-alkyl or acyl, each of which can be optionally substituted.

In some embodiments, R⁵ is H.

In one embodiment, the compound of formula (I) has the structure shown in formula (Ib):

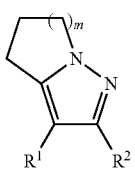

Formula (Ib), wherein m is 1, 2 or 3.

Exemplary compounds of formula (I) include:

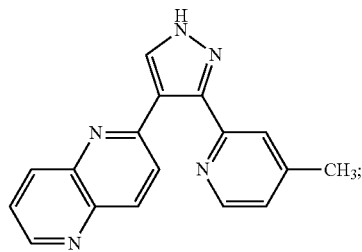

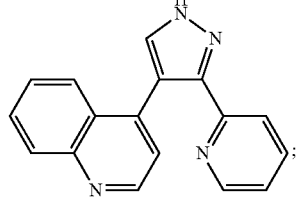

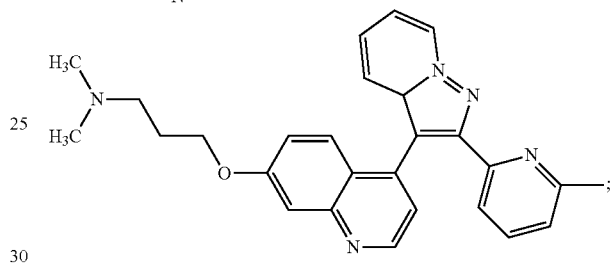

4-[2-(6-Ethyl-pyridin-2-yl)-pyrazolo[1,5-a]pyridin-3-yl]-quinoline;
[2-(6-Methyl-pyridin-2-yl)-pyrazolo[1,5-a]pyridin-3-yl] quinoline-7-carboxylic acid methyl ester;
4-[2-(6-Methyl-pyridin-2-yl)-pyrazolo[1,5-a]pyridin-3-yl]-quinoline-6-carboxylic acid methyl ester;
4-(5-Benzyl-2-pyridin-2-yl-pyrazolo[1,5-a]pyridin-3-yl)-quinoline-7-carboxylic acid methyl ester;
3-(4-Fluoro-phenyl)-2-(6-methyl-pyridin-2-yl)-pyrazolo[1,5-a]pyridine-6-carboxylic acid (2-dimethylamino-ethyl)-amide;
4-[2-(6-Methyl-pyridin-2-yl)-pyrazolo[1,5-a]pyridin-3-yl]-quinoline-6-carboxylic acid (2-dimethylamino-ethyl)-amide;
4-[2-(6-Methyl-pyridin-2-yl)-pyrazolo[1,5-a]pyridin-3-yl]-quinoline-7-carboxylic acid (2-dimethylamino-ethyl)-amide;
5-[2-(6-Methyl-pyridin-2-yl)-pyrazolo[1,5-a]pyridin-3-yl]-benzofuran-2-carboxylic acid (2-dimethyl amino-ethyl)-amide;
4-[2-(6-Methyl-pyridin-2-yl)-pyrazolo[1,5-a]pyridin-3-yl]-quinoline-7-carboxylic acid [3-(4-methyl-piperazin-1-yl)-propyl]-amide;
4-[2-(6-Methoxy-pyridin-2-yl)-pyrazolo[1,5-a]pyridin-3-yl]-quinoline, 4-[2-(6-Ethoxy-pyridin-2-yl)-pyrazolo[1,5-a]pyridin-3-yl]-quinoline;
3-(4-Fluoro-phenyl)-2-(6-methoxy-pyridin-2-yl)-pyrazolo[1,5-a]pyridine;
2-(6-Ethoxy-pyridin-2-yl)-3-(4-fluoro-phenyl)-pyrazolo[1,5-a]pyridine;
7-Benzyl-4-[2-(6-methyl-pyridin-2-yl)-pyrazolo[1,5-a]pyridin-3-yl]-quinoline;
3-{4-[2-(6-Methyl-pyridin-2-yl)-pyrazolo[1,5-a]pyridin-3-yl]-quinolin-7-yl}-acrylic acid methyl ester;
3-{4-[2-(6-Methyl-pyridin-2-yl)-pyrazolo[1,5-a]pyridin-3-yl]-quinolin-7-yl}-acrylic acid;

4-[2-(6-Ethylsulfanyl-pyridin-2-yl)-pyrazolo[1,5-a]-pyridin-3-yl]-quinoline;
4-[2-(6-Phenylsulfanyl-pyridin-2-yl)-pyrazolo[1,5-a]pyridin-3-yl]-quinoline;
4-[2-(6-Morpholin-4-yl-pyridin-2-yl)-pyrazolo[1,5-a]pyridin-3-yl]-quinoline;
3-(4-Fluoro-phenyl)-2-(6-methylsulfanyl-pyridin-2-yl)-pyrazolo[1,5-a]pyridine;
3-(4-Methylsulfanyl-phenyl)-2-(6-methylsulfanyl-pyridin-2-yl)-pyrazolo[1,5-a]pyridine;
Dimethyl-{4-[2-(6-methyl-pyridin-2-yl)-pyrazolo[1,5-a]pyridin-3-yl]-quinolin-7-ylsulfanyl}-ethyl)-amine;
2-(Pyridin-2-yl)-3-(quinolin-4-yl)-pyrazolo[1,5-a]pyridine-5-carboxylic acid dimethylamide;
2-(Pyridin-2-yl)-3-(quinolin-4-yl)-pyrazolo[1,5-a]pyridine-6-carboxylic acid dimethylamide;
4-[2-(6-Vinyl-pyridin-2-yl)-pyrazolo[1,5-a]pyridin-3-yl]-quinoline, 6-[2-(6-Methyl-pyridin-2-yl)-pyrazolo[1,5-a]pyridin-3-yl]-imidazo[1,2-a]pyridin-2-yl-amine;
6-[2-(6-Methyl-pyridin-2-yl)-pyrazolo[1,5-a]pyridin-3-yl]-1H-benzoimidazol-2-yl-amine;
[3-(4-Fluoro-phenyl)-2-(6-methyl-pyridin-2-yl)-pyrazolo[1,5-a]pyridin-6-yl]-methanol, 6-Allyloxymethyl-3-(4-fluoro-phenyl)-2-(6-methyl-pyridin-2-yl)-pyrazolo[1,5-a]pyridine;
4-[2-(6-Methyl-pyridin-2-yl)-pyrazolo[1,5-a]pyridin-3-yl]-quinoline-7-carboxylic acid (3-pyrrolidin-1-yl-propyl)-amide;
3-{4-[2-(6-Methyl-pyridin-2-yl)-pyrazolo[1,5-a]pyridin-3-yl]-quinolin-7-yl}-propionamide;
3-{4-[2-(6-Methyl-pyridin-2-yl)-pyrazolo[1,5-a]pyridin-3-yl]-quinolin-7-yl}-N-(3-pyrrolidin-1-yl-propyl)-propionamide;
N-(Dimethylamino-ethyl)-3-{4-[2-(6-methyl-pyridin-2-yl)-pyrazolo[1,5-a]pyridin-3-yl]-quinolin-7-yl}-propionamide;
2-Pyridin-2-yl-3-quinolin-4-yl-pyrazolo[1,5-a]pyridine-5-carboxylic acid (3-dimethylamino-propyl)-amide;
4-[2-(6-Methyl-pyridin-2-yl)-pyrazolo[1,5-a]pyridin-3-yl]-quinoline-7-carboxylic acid (2-hydroxy-ethyl)-amide;
4-[2-(6-Methyl-pyridin-2-yl)-pyrazolo[1,5-a]pyridin-3-yl]-quinoline-7-carboxylic acid hydrazide;
4-[2-(6-Methyl-pyridin-2-yl)-pyrazolo[1,5-a]pyridin-3-yl]-quinoline-7-carboxylic acid (3-hydroxy-propyl)-amide;
4-[2-(6-Methyl-pyridin-2-yl)-pyrazolo[1,5-a]pyridin-3-yl]-quinoline-7-carboxylic acid methylamide;
4-[2-(6-Methyl-pyridin-2-yl)-pyrazolo[1,5-a]pyridin-3-yl]-quinoline-7-carboxylic acid (3-ethoxy-propyl)-amide;
4-[2-(6-Methyl-pyridin-2-yl)-pyrazolo[1,5-a]pyridin-3-yl]-quinoline-7-carboxylic acid (3-morpholin-4-yl-propyl)-amide; 4-[2-(6-Methyl-pyridin-2-yl)-pyrazolo[1,5-a]pyridin-3-yl]-quinoline-7-carboxylic acid 3-imidazol-1-yl-propyl)-amide;
4-[2-(6-Methyl-pyridin-2-yl)-pyrazolo[1,5-a]pyridin-3-yl]-quinoline-7-carboxylic acid (3-dimethylamino-propyl)-amide;
4-[2-(6-Methyl-pyridin-2-yl)-pyrazolo[1,5-a]pyridin-3-yl]-quinoline-7-carboxylic acid [2-(2-methoxy-phenyl)-ethyl]-amide;
4-[2-(6-Methyl-pyridin-2-yl)-pyrazolo[1,5-a]pyridin-3-yl]-quinoline-7-carboxylic acid (2-morpholin-4-yl-ethyl)-amide;
4-[2-(6-Methyl-pyridin-2-yl)-pyrazolo[1,5-a]pyridin-3-yl]-quinoline-7-carboxylic acid amide;
Dimethyl-{4-[2-(6-methyl-pyridin-2-yl)-pyrazolo[1,5-a]pyridin-3-yl]-quinolin-7-yloxy}-propyl)-amine;
4-[2-(6-Methyl-pyridin-2-yl)-pyrazolo[1,5-a]pyridin-3-yl]-7-(2-morpholin-4-yl-ethoxy)-quinoline;
Diisopropyl-(2-{4-[2-(6-methyl-pyridin-2-yl)-pyrazol[1,5-a]pyridin-3-yl]-quinolin-7-yloxy}-ethyl)-amine;
4-[2-(6-Methyl-pyridin-2-yl)-pyrazolo[1,5-a]pyridin-3-yl]-7-(2-pyrrol-1-yl-ethoxy)-quinoline;
Dimethyl-(1-methyl-2-{4-[2-(6-methyl-pyridin-2-yl)-pyrazolo[1,5-a]pyridin-3-yl]-quinolin-7-yloxy}ethyl)-amine;
Methyl-(3-{4-[2-(6-methyl-pyridin-2-yl)-pyrazolo[1,5-a]pyridin-3-yl]-quinolin-7-yl-oxy}-propyl)-amine;
4-[2-(6-Methyl-pyridin-2-yl)-pyrazolo[1,5-a]pyridin-3-yl]-7-(2-piperidin-1-yl-ethoxy)-quinoline;
Diethyl-(2-{4-[2-(6-methyl-pyridin-2-yl)-pyrazolo[1,5-a]pyridin-3-yl]-quinolin-7-yloxy}-ethyl)-amine;
Dimethyl-{3-[4-(2-pyridin-2-yl-pyrazolo[1,5-a]pyridin-3-yl)-quinolin-7-yloxy]-propyl}-amine;
7-(2-Morpholin-4-yl-ethoxy)-4-(2-pyridin-2-yl-pyrazolo[1,5-a]pyridin-3-yl)-quinoline;
Diisopropyl-{2-[4-(2-pyridin-2-yl-pyrazolo[1,5-a]pyridin-3-yl)-quinolin-7-yloxy]-ethyl}-amine;
4-[2-(6-Methyl-pyridin-2-yl)-pyrazolo[1,5-a]pyridin-3-yl]-7-(3-morpholin-4-yl-propoxy)-quinoline;
1-(3-{4-[2-(6-Methyl-pyridin-2-yl)-pyrazolo[1,5-a]pyridine-3-yl]-quinolin-7-yloxy}-propyl)-1,3-dihydro-benzoimidazol-2-one 3-{4-[2-(6-Methyl-pyridin-2-yl)-pyrazolo[1,5-a]pyridin-3-yl]-quinolin-7-yl}-propionic acid methyl ester;
Diethyl-3-[4-(2-pyridin-2-yl-pyrazolo[1,5-a]pyridin-3-yl)-quinolin-7-yloxy]-propyl}-amine;
Ethyl-methyl-{3-[4-(2-pyridin-2-yl-pyrazolo[1,5-a]pyridin-3-yl)-quinolin-7-yloxy]-propyl}-amine;
4-(2-Pyridin-2-yl-pyrazolo[1,5-a]pyridin-3-yl)-7-(3-pyrrolidin-1-yl-propoxy)-quinoline;
7-(3-Piperidin-1-yl-propoxy)-4-(2-pyridin-2-yl-pyrazolo[1,5-a]pyridin-3-yl)-quinoline;
Diethyl-{2-[4-(2-pyridin-2-yl-pyrazolo[1,5-a]pyridin-3-yl)-quinolin-7-yloxy]-ethyl}-amine;
Dimethyl-{2-[4-(2-pyridin-2-yl-pyrazolo[1,5-a]pyridin-3-yl)-quinolin-7-yloxy]-ethyl}-amine;
6-Bromo-4-(2-pyridin-2-yl-5,6-dihydro-4H-pyrrolo[1,2-b]pyrazol-3-yl)-quinoline;
3-Pyridin-4-yl-2-pyridin-2-yl-5,6-dihydro-4H-pyrrolo[1,2-b]pyrazole;
2-(6-Methyl-pyridin-2-yl)-3-p-tolyl-5,6-dihydro-4H-pyrrolo[1,2-b]pyrazole;
4-[3-(6-Methyl-pyridin-2-yl)-5,6-dihydro-4H-pyrrolo[1,2-b]pyrazol-2-yl]-quinoline;
2-(6-Methyl-pyridin-2-yl)-3-naphthalen-1-yl-5,6-dihydro-4H-pyrrolo[1,2-b]pyrazole;
(6-Methyl-pyridin-2-yl)-3-pyridin-3-yl-5,6-dihydro-4H-pyrrolo[1,2-b]pyrazole;
3-(4-Fluoro-naphthalen-1-yl)-2-(6-methyl-pyridin-2-yl)-5,6-dihydro-4H-pyrrolo[1,2-b]pyrazole;
3-(3,4-Difluoro-phenyl)-2-(6-methyl-pyridin-2-yl)-5,6-dihydro-4H-pyrrolo[1,2-b]pyrazole;
1-[2-(4-Methanesulfonyl-phenyl)-1-(6-methyl-pyridin-2-yl)-ethylideneamino]-pyrrolidin-2-one;
7-Methoxy-4-(2-pyridin-2-yl-5,6-dihydro-4H-pyrrolo[1,2-b]pyrazol-3-yl)-quinoline;
7-Benzyloxy-6-methoxy-4-(2-pyridin-2-yl-5,6-dihydro-4H-pyrrolo[1,2-b]pyrazol-3-yl)-quinoline;
6-(2-Pyridin-2-yl-5,6-dihydro-4H-pyrrolo[1,2-b]pyrazol-3-yl)-quinoline;
6-[2-(6-Methyl-pyridin-2-yl)-5,6-dihydro-4H-pyrrolo[1,2-b]pyrazol-3-yl]-quinoline;
3-Naphthalen-2-yl-2-pyridin-2-yl-5,6-dihydro-4H-pyrrolo[1,2-b]pyrazole;

2-(6-Methyl-pyridin-2-yl)-3-naphthalen-2-yl-5,6-dihydro-4H-pyrrolo[1,2-b]pyrazole;
3-(4-Fluoro-phenyl)-2-(6-trifluoromethyl-pyridin-2-yl)-5,6-dihydro-4H-pyrrolo[1,2-b]pyrazole;
4-(Quinolin-4-yl)-3-(5-fluoropyridin-2-yl)-5,6-dihydro-4H-pyrrolo[1,2-b]pyrazole;
4-(7-Bromoquinolin-4-yl)-3-(pyridin-2-yl)-5,6-dihydro-4H-pyrrolo[1,2-b]pyrazole;
(Quinolin-4-yl)-3-(2,4-difluorophenyl)-5,6-dihydro-4H-pyrrolo[1,2-b]pyrazole;
4-(2-Pyrazin-2-yl-5,6-dihydro-4H-pyrrolo[1,2-b]pyrazol-3-yl)-quinoline;
4-(5-Methyl-2-pyridin-2-yl-5,6-dihydro-4H-pyrrolo[1,2-b]pyrazol-3-yl)-quinoline;
6-Bromo-4-[2-(6-methyl-pyridin-2-yl)-5,6-dihydro-4H-pyrrolo[1,2-b]pyrazol-3-yl]-quinoline;
4-[2-(6-Methyl-pyridin-2-yl)-5,6-dihydro-4H-pyrrolo[1,2-b]pyrazol-3-yl]-6-trifluoromethyl-quinoline;
3-(3-Chloro-4-fluoro-phenyl)-2-(6-methyl-pyridin-2-yl)-5,6-dihydro-4H-pyrrolo[1,2-b]pyrazole;
3-(2-Chloro-4-fluoro-phenyl)-2-(6-methyl-pyridin-2-yl)-5,6-dihydro-4H-pyrrolo[1,2-b]pyrazole;
3-(4-Fluoro-3-trifluoromethyl-phenyl)-2-(6-methyl-pyridin-2-yl)-5,6-dihydro-4H-pyrrolo[1,2-b]pyrazole;
2-(6-Methyl-pyridin-2-yl)-3-(2,4,5-trifluoro-phenyl)-5,6-dihydro-4H-pyrrolo[1,2-b]pyrazole;
8-Fluoro-4-[2-(6-methyl-pyridin-2-yl)-5,6-dihydro-4H-pyrrolo[1,2-b]pyrazol-3-yl]-quinoline;
7-Bromo-4-[2-(6-methyl-pyridin-2-yl)-5,6-dihydro-4H-pyrrolo[1,2-b]pyrazol-3-yl]-quinoline;
4-[2-(6-Methyl-pyridin-2-yl)-5,6-dihydro-4H-pyrrolo[1,2-b]pyrazol-3-yl]-6-trifluoromethoxy-quinoline;
4-[2-(6-Methyl-pyridin-2-yl)-5,6-dihydro-4H-pyrrolo[1,2-b]pyrazol-3-yl]-7-trifluoromethyl-quinoline;
7-Methoxy-4-[2-(6-methyl-pyridin-2-yl)-5,6-dihydro-4H-pyrrolo[1,2-b]pyrazol-3-yl]-quinoline;
3-(2-Chloro-pyridin-4-yl)-2-pyridin-2-yl-5,6-dihydro-4H-pyrrolo[1,2-b]pyrazole;
[2-(6-Methyl-pyridin-2-yl)-3-quinolin-4-yl-5,6-dihydro-4H-pyrrolo[1,2-b]pyrazol-6-yl]-methanol;
[3-(7-Bromo-quinolin-4-yl)-2-(6-methyl-pyridin-2-yl)-5,6-dihydro-4H-pyrrolo[1,2-b]pyrazol-6-yl]-methanol;
4-[2-(6-Chloro-pyridin-2-yl)-5-(4-fluorophenyl)-5,6-dihydro-4H-pyrrolo[1,2-b]pyrazol-3-yl]-quinoline;
4-[2-(6-Ethoxy-pyridin-2-yl)-5-(4-fluoro-phenyl)-5,6-dihydro-4H-pyrrolo[1,2-b]pyrazol-3-yl]-quinoline;
(S)-4-[6-Benzyloxymethyl-2-(6-methyl-pyridin-2-yl)-5,6-dihydro-4H-pyrrolo[1,2-b]pyrazol-3-yl]-7-chloro-quinoline;
(S)-4-[6-Benzyloxymethyl-2-(6-chloro-pyridin-2-yl)-5,6-dihydro-4H-pyrrolo[1,2-b]pyrazol-3-yl]-quinoline;
4-[2-(6-Methyl-pyridin-2-yl)-3-quinolin-4-yl-5,6-dihydro-4H-pyrrolo[1,2-b]pyrazol-5-yl]-benzoic acid ethyl ester;
3-(4-Fluoro-phenyl)-5,5-dimethyl-2-(6-methyl-pyridin-2-yl)-5,6-dihydro-4H-pyrrolo[1,2-b]pyrazole;
(R)-6-Benzyloxymethyl-3-(4-fluoro-phenyl)-2-(6-methyl-pyridin-2-yl)-5,6-dihydro-4H-pyrrolo[1,2-b]pyrazole;
5-(4-Chloro-phenyl)-3-(4-fluoro-phenyl)-2-(6-methyl-pyridin-2-yl)-5,6-dihydro-4H-pyrrolo[1,2-b]pyrazole;
4-[2-(3-Trifluoromethyl-phenyl)-4,5,6,7-tetrahydro-pyrazolo[1,5-a]pyridin-3-yl]-quinoline;
4-[2-(4-Trifluoromethyl-phenyl)-4,5,6,7-tetrahydro-pyrazolo[1,5-a]pyridin-3-yl]-quinoline;
4-[2-(4-Chloro-phenyl)-4,5,6,7-tetrahydro-pyrazolo[1,5-a]pyridin-3-yl]-quinoline;
4-[2-(3-Chloro-phenyl)-4,5,6,7-tetrahydro-pyrazolo[1,5-a]pyridin-3-y]-quinoline;
4-[2-(3-Fluoro-5-trifluoromethyl-phenyl)-5,6-dihydro-4H-pyrrolo[1,2-b]pyrazol-3-yl]-quinoline;
4-[2-(3-Fluoro-5-trifluoromethyl-phenyl)-4,5,6,7-tetrahydro-pyrazolo[1,5-a]pyridin-3-yl]-quinoline;
4-(2-Phenyl-4,5,6,7-tetrahydro-pyrazolo[1,5-a]pyridin-3-yl)-quinoline;
4-(2-Pyridin-2-yl-4,5,6,7-tetrahydro-pyrazolo[1,5-a]pyridin-3-yl)-[1,10]phenanthroline;
4-[2-(4-Fluoro-phenyl)-4,5,6,7-tetrahydro-pyrazolo[1,5-a]pyridin-3-yl]-quinoline;
4-[2-(3-Trifluoromethoxy-phenyl)-4,5,6,7-tetrahydro-pyrazolo[1,5-a]pyridin-3-yl]-quinoline;
4-[2-(2-Fluoro-phenyl)-4,5,6,7-tetrahydro-pyrazolo[1,5-a]pyridin-3-yl]-quinoline;
4-[2-Quinolin-2-yl-4,5,6,7-tetrahydro-pyrazolo[1,5-a]pyridin-3-yl]-quinoline;
4-[2-(4-Ethyl-pyridin-2-yl)-4,5,6,7-tetrahydro-pyrazolo[1,5-a]pyridin-3-yl]-quinoline;
4-(2-Quinolin-2-yl-5,6-dihydro-4H-pyrrolo[1,2-b]pyrazol-3-yl)-quinoline;
2-(3-Quinolin-4-yl-4,5,6,7-tetrahydro-pyrazolo[1,5-a]pyridin-2-yl)-[1,8]naphthyridine;
4-[5-(4-Fluoro-phenyl)-2-pyridin-2-yl-5,6-dihydro-4H-pyrrolo[1,2-b]pyrazol-3-yl]-quinoline;
4-(6-Hydroxymethyl-2-pyridin-2-yl-5,6-dihydro-4H-pyrrolo[1,2-b]pyrazol-3-yl)-quinoline;
4-(3-Pyridin-2-yl-5,6-dihydro-4H-pyrrolo[1,2-b]pyrazol-2-yl)-quinoline;
4-(4-Methyl-2-pyridin-2-yl-5,6-dihydro-4H-pyrrolo[1,2-b]pyrazol-3-yl)-quinoline;
4-(5-Benzyl-2-pyridin-2-yl-5,6-dihydro-4H-pyrrolo[1,2-b]pyrazol-3-yl)-quinoline;
4-(5-Phenethyl-2-pyridin-2-yl-5,6-dihydro-4H-pyrrolo[1,2-b]pyrazol-3-yl)-quinoline;
4-(5-Phenyl-2-pyridin-2-yl-5,6-dihydro-4H-pyrrolo[1,2-b]pyrazol-3-yl)-quinoline;
4-[2-(3-Trifluoromethylphenyl)-5,6-dihydro-4H-pyrrolo[1,2-b]pyrazol-3-yl]-quinoline;
4-[2-(4-Trifluoromethyl-phenyl)-5,6-dihydro-4H-pyrrolo[1,2-b]pyrazol-3-yl]-quinoline;
4-(2-Phenyl-5,6-dihydro-4H-pyrrolo[1,2-b]pyrazol-3-yl)-quinoline;
2-Chloro-4-(2-pyridin-2-yl-5,6-dihydro-4H-pyrrolo[1,2-b]pyrazol-3-yl)-quinoline;
6,8-Dimethoxy-4-[2-(6-methyl-pyridin-2-yl)-5,6-dihydro-4H-pyrrolo[1,2b]pyrazol-3-yl]-quinoline;
4-[2-(6-Bromo-pyridin-2-yl)-5,6-dihydro-4H-pyrrolo[1,2-b]pyrazol-3-yl]-quinoline;
6,8-Dimethoxy-4-[2-pyridin-2-yl-5,6-dihydro-4H-pyrrolo[1,2b]pyrazol-3-yl]-quinoline;
3-(4-Fluorophenyl)-2-pyridin-2-yl-5,6-dihydro-4H-pyrrolo[1,2-b]pyrazole;
3-(4-Methoxy-phenyl)-2-pyridin-2-yl-5,6-dihydro-4H-pyrrolo[1,2-b]pyrazole;
3-(4-Fluorophenyl)-2-(6-methylpyridin-2-yl)-5,6-dihydro-4H-pyrrolo[1,2-b]pyrazole;
3-(4-Methoxyphenyl)-2-(6-methylpyridin-2-yl)-5,6-dihydro-4H-pyrrolo[1,2-b]pyrazole;
4-(2-Thiophen-2-yl-5,6-dihydro-4H-pyrrolo[1,2-b]pyrazol-3-yl) quinoline;
4-[2-(6-Propylpyridin-2-yl)-5,6-dihydro-4H-pyrrolo[1,2-b]pyrazol-3-yl]-quinoline;
4-[2-(6-Isopropylpyridin-2-yl)-5,6-dihydro-4H-pyrrolo[1,2-b]pyrazol-3-yl]quinoline;
4-[2-(6-Ethyl-pyridin-2-yl)-5,6-dihydro-4H-pyrrolo[1,2-b]pyrazol-3-yl]quinoline;

4-[2-(6-Methyl-pyridin-2-yl)-5,6-dihydro-4H-pyrrolo[1,2-b]pyrazol-3-yl]-quinoline;
4-[2-(3-Fluorophenyl)-5,6-dihydro-4H-pyrrolo[1,2-b]pyrazol-3-yl]-quinoline;
4-[2-(2-Fluoro-phenyl)-5,6-dihydro-4H-pyrrolo[1,2-b]pyrazol-3-yl]-quinoline;
4-[2-(4-Fluoro-phenyl)-5,6-dihydro-4H-pyrrolo[1,2-b]pyrazol-3-yl]-quinoline;
4-[2-(3-Trifluoromethoxy-phenyl)-5,6-dihydro-4H-pyrrolo[1,2-b]pyrazol-3-yl]-quinoline;
4-[2-(4-Chloro-pyridin-2-yl)-5,6-dihydro-4H-pyrrolo[1,2-b]pyrazol-3-yl]-quinoline;
4-[2-(4-Fluoro-3-trifluoromethyl-phenyl)-5,6-dihydro-4H-pyrrolo[1,2-b]pyrazol-3-yl]quinoline;
4-[2-(2-Fluoro-3-trifluoromethyl-phenyl)-5,6-dihydro-4H-pyrrolo[1,2-b]-pyrazol-3-yl]-quinoline;
4-[5-(3-Methoxy-phenyl)-2-pyridin-2-yl-5,6-dihydro-4H-pyrrolo[1,2-b]pyrazol-3-yl]-quinoline;
4-[2-(4-Fluoro-3-trifluoromethyl-phenyl)-5-(3-methoxy-phenyl)-5,6-dihydro-4H-pyrrolo[1,2-b]pyrazol-3-yl]-quinoline;
4-(7-Chloro-quinolin-4-yl)-3-(6-methylpyridin-2-yl)-5,6-dihydro-4H-pyrrolo[1,2-b]pyrazole;
4-(7-Ethoxyquinolin-4-yl)-3-(6-methylpyridin-2-yl)-5,6-dihydro-4H-pyrrolo[1,2-b]pyrazole;
6-(3-Quinolin-4-yl-5,6-dihydro-4H-pyrrolo[1,2-b]pyrazol-2-yl)-pyridine-2-carboxylic acid hydrochloride;
6,7-Difluoro-4-[2-(6-methyl-pyridin-2-yl)-5,6-dihydro-4H-pyrrolo[1,2-b]pyrazol-3-yl]-quinoline;
6,7-Dimethoxy-4-[2-(6-methyl-pyridin-2-yl)-5,6-dihydro-4H-pyrrolo[1,2-b]pyrazol-3-yl]-quinoline;
3-Benzo[1,3]dioxol-5-yl-2-(6-methyl-pyridin-2-yl)-5,6-dihydro-4H-pyrrolo[1,2-b]pyrazole;
6-(4-Fluoro-phenyl)-4-[2-(6-methyl-pyridin-2-yl)-5,6-dihydro-4H-pyrrolo[1,2-b]pyrazol-3-yl]-quinoline;
6-Benzo[1,3]dioxol-5-yl-4-[2-(6-methyl-pyridin-2-yl)-5,6-dihydro-4H-pyrrolo[1,2-b]pyrazol-3-yl]-quinoline;
4-[2-(6-Methyl-pyridin-2-yl)-5,6-dihydro-4H-pyrrolo[1,2-b]pyrazol-3-yl]-6-thiophen-2-yl-quinoline;
4-[2-(6-Methyl-pyridin-2-yl)-5,6-dihydro-4H-pyrrolo[1,2-b]pyrazol-3-yl]-6-phenyl-quinoline;
8-[2-(6-Methyl-pyridin-2-yl)-5,6-dihydro-4H-pyrrolo[1,2-b]pyrazol-3-yl]-quinoline;
3-Benzo[b]thiophen-2-yl-2-(6-methyl-pyridin-2-yl)-5,6-dihydro-4H-pyrrolo[1,2-b]pyrazole;
4-(2-Pyridin-2-yl-5,6-dihydro-4H-pyrrolo[1,2-b]pyrazol-3-yl)-quinoline-6-carboxylic acid methyl ester;
4-[2-(6-Methyl-pyridin-2-yl)-5,6-dihydro-4H-pyrrolo[1,2-b]pyrazol-3-yl]-quinoline-6-carboxylic acid methyl ester;
4-[2-(6-Methyl-pyridin-2-yl)-5,6-dihydro-4H-pyrrolo[1,2-b]pyrazol-3-yl]-quinoline-7-carboxylic acid methyl ester;
4-[2-Pyridin-2-yl-5,6-dihydro-4H-pyrrolo[1,2-b]pyrazol-3-yl]-quinoline-7-carboxylic acid methyl ester;
2-Pyridin-2-yl-3-quinolin-4-yl-pyrazolo[5,1-c]morpholine;
2-Pyridin-2-yl-3-quinolin-4-yl-pyrazolo[5,1-c]morpholin-4-one;
Dimethyl-{3-[4-(2-pyridin-2-yl-5,6-dihydro-4H-pyrrolo[1,2-b]pyrazol-3-yl)-quinolin-7-yloxy]-propyl}-amine;
{3-[6-Methoxy-4-(2-pyridin-2-yl-5,6-dihydro-4H-pyrrolo[1,2-b]pyrazol-3-yl)-quinolin-7-yloxy]-propyl}-dimethyl-amine;
Cyclopropylmethyl-propyl-{3-[4-(2-pyridin-2-yl-5,6-dihydro-4H-pyrrolo[1,2-b]pyrazol-3-yl)-quinolin-7-yloxy]-propyl}-amine;
Diethyl-f3-[4-(2-pyridin-2-yl-5,6-dihydro-4H-pyrrolo[I,2-b]pyrazol-3-yl)-quinolin-7-yloxy]-propyl}-amine;
Ethyl-methyl-{3-[4-(2-pyridin-2-yl-5,6-dihydro-4H-pyrrolo[1,2-b]pyrazol-3-yl)-quinolin-7-yloxy]-propyl}-amine)
jjjjj) 3-[4-(2-Pyridin-2-yl-5,6-dihydro-4H-pyrrolo[1,2-b]pyrazol-3-yl)-quinolin-7-yloxy]-propylamine;
7-[3-(4-Methyl-piperazin-1-yl)-propoxy]-4-(2-pyridin-2-yl-5,6-dihydro-4H-pyrrolo[1,2-b]pyrazol-3-yl)-quinoline;
Benzyl-methyl-{3-[4-(2-pyridin-2-yl-5,6-dihydro-4H-pyrrolo[1,2-b]pyrazol-3-yl)-quinolin-7-yloxy]-propyl}-amine;
7-(3-Piperidin-1-yl-propoxy)-4-(2-pyridin-2-yl-5,6-dihydro-4H-pyrrolo[1,2-b]pyrazol-3-yl)-quinoline;
4-(2-Pyridin-2-yl-5,6-dihydro-4H-pyrrolo[1,2-b]pyrazol-3-yl)-7-(3-pyrrolidin-1-yl-propoxy)-quinoline;
7-(3-Azepan-1-yl-propoxy)-4-(2-pyridin-2-yl-5,6-dihydro-4H-pyrrolo[1,2-b]pyrazol-3-yl)-quinoline;
7-(3-Imidazol-1-yl-propoxy)-4-(2-pyridin-2-yl-5,6-dihydro-4H-pyrrolo[1,2-b]pyrazol-3-yl)-quinoline;
7-(3-Pyrazol-1-yl-propoxy)-4-(2-pyridin-2-yl-5,6-dihydro-4H-pyrrolo[1,2-b]pyrazol-3-yl)-quinoline;
1'-{3-[4-(2-Pyridin-2-yl-5,6-dihydro-4H-pyrrolo[1,2-b]pyrazol-3-yl)-quinolin-7-yloxy]-propyl}-[1,4']bipiperidinyl;
Cyclopropyl-(1-methyl-piperidin-4-yl)-f3-[4-(2-pyridin-2-yl-5,6-dihydro-4H-pyrrolo[1,2-b]pyrazol-3-yl)-quinolin-7-yloxy]-propyl}-amine;
4-(2-Pyridin-2-yl-5,6-dihydro-4H-pyrrolo[1,2-b]pyrazol-3-yl)-7-(3-[1,2,3]triazol-1-yl-propoxy)-quinoline;
Dimethyl-(3-{4-[2-(6-methyl-pyridin-2-yl)-5,6-dihydro-4H-pyrrolo[1,2-b]pyrazol-3-yl]-quinolin-7-yloxy}-propyl)-amine;
Diethyl-(3-{4-[2-(6-methyl-pyridin-2-yl)-5,6-dihydro-4H-pyrrolo[1,2-b]pyrazol-3-yl]-quinolin-7-yloxy}-propyl)-amine;
Cyclopropylmethyl-(3-{4-[2-(6-methyl-pyridin-2-yl)-5,6-dihydro-4H-pyrrolo[1,2-b]pyrazol-3-yl]-quinolin-7-yloxy}-propyl)-propyl-aurin;
Ethyl-methyl-(3-{4-[2-(6-methyl-pyridin-2-yl)-5,6-dihydro-4H-pyrrolo[1,2-b]pyrazol-3-yl]-quinolin-7-yloxy}-propyl)-amine;
Dimethyl-{2-[4-(2-pyridin-2-yl-5,6-dihydro-4H-pyrrolo[1,2-b]pyrazol-3-yl)-quinolin-7-yloxy]-ethyl}-amine;
Diethyl-{2-[4-(2-pyridin-2-yl-5,6-dihydro-4H-pyrrolo[1,2-b]pyrazol-3-yl)-quinolin-7-yloxy]-ethyl}-amine;
7-(2-Piperidin-1-yl-ethoxy)-4-(2-pyridin-2-yl-5,6-dihydro-4H-pyrrolo[1,2-b]pyrazol-3-yl)-quinoline;
Ethyl-methyl-{2-[4-(2-pyridin-2-yl-5,6-dihydro-4H-pyrrolo[1,2-b]pyrazol-3-yl)-quinolin-7-yloxy]ethyl}-amine;
4-(2-Pyridin-2-yl-5,6-dihydro-4H-pyrrolo[1,2-b]pyrazol-3-yl)-7-(2-pyrrolidin-1-yl-ethoxy)-quinoline;
7-[2-(4-Methyl-piperazin-1-yl)-ethoxy]-4-(2-pyridin-2-yl-5,6-dihydro-4H-pyrrolo[1,2-b]pyrazol-3-yl)-quinoline;
Dimethyl-{3-[1-oxy-4-(2-pyridin-2-yl-5,6-dihydro-4H-pyrrolo[1,2-b]pyrazol-3-yl)-quinolin-7-yloxy]-propyl}-amine;
7-Methylsulfanyl-4-(2-pyridin-2-yl-5,6-dihydro-4H-pyrrolo[1,2-b]pyrazol-3-yl)-quinoline;
7-Ethylsulfanyl-4-(2-pyridin-2-yl-5,6-dihydro-4H-pyrrolo[1,2-b]pyrazol-3-yl)-quinoline;
6-Methylsulfanyl-4-(2-pyridin-2-yl-5,6-dihydro-4H-pyrrolo[1,2-b]pyrazol-3-yl)-quinoline;
7-Benzylsulfanyl-4-(2-pyridin-2-yl-5,6-dihydro-4H-pyrrolo[1,2-b]pyrazol-3-yl)-quinoline;
3-[4-(2-Pyridin-2-yl-5,6-dihydro-4H-pyrrolo[1,2-b]pyrazol-3-yl)-quinolin-7-yl sulfanyl]-propan-1-ol;
Dimethyl-{2-[4-(2-pyridin-2-yl-5,6-dihydro-4H-pyrrolo[1,2-b]pyrazol-3-yl)-quinolin-7-yl sulfanyl]-ethyl}-amine;

Dimethyl [6-(3-quinolin-4-yl-5,6-dihydro-4H-pyrrolo[1,2-b]pyrazol-2-yl)-pyridin-2-yl-methyl]amine;
7-(2-Propoxy-ethoxy)-4-(2-pyridin-2-yl-5,6-dihydro-4H-pyrrolo[1,2-b]pyrazol-3-yl)-quinoline;
N,N-Dimethyl-N'-[4-(2-pyridin-2-yl-5,6-dihydro-4H-pyrrolo[1,2-b]pyrazol-3-yl)-pyridin-2-yl]-ethane-1,2-diamine;
N,N-Dimethyl-N'-[4-(2-pyridin-2-yl-5,6-dihydro-4H-pyrrolo[1,2-b]pyrazol-3-yl)-pyridin-2-yl]-propane-1,3-diamine;
3-{3-[4-(2-Pyridin-2-yl-5,6-dihydro-4H-pyrrolo[1,2-b]pyrazol-3-yl)-quinolin-7-yloxy]-propyl}-oxazolidin-2-one;
1-{3-[4-(2-Pyridin-2-yl-5,6-dihydro-4H-pyrrolo[1,2-b]pyrazol-3-yl)-quinolin-7-yloxy]-propyl}-imidazolidin-2-one;
3-{3-[4-(2-Pyridin-2-yl-5,6-dihydro-4H-pyrrolo[1,2-b]pyrazol-3-yl)-quinolin-7-yloxy]-propyl}-3H-benzooxazol-2-one;
Dimethyl-(2-{4-[2-(6-methyl-pyridin-2-yl)-5,6-dihydro-4H-pyrrolo[1,2-b]pyrazol-3-yl]-pyridin-2-ylsulfanyl}-ethyl-amine;
4-(2-Pyridin-2-yl-5,6-dihydro-4H pyrrolo[1,2-b]pyrazol-3-yl)-2pyrrolidin-1-yl-quinoline;
2-Phenylsulfanyl-4-(2-pyridin-2-yl-5,6-dihydro-4H-pyrrolo[1,2-b]pyrazol-3-yl)-quinoline;
2-Morpholin-4-yl-4-(2-pyridin-2-yl-5,6-dihydro-4H-pyrrolo[1,2-b]pyrazol-3-yl)-quinoline;
2-Ethylsulfanyl-4-(2-pyridin-2-yl-5,6-dihydro-4H-pyrrolo[1,2-b]pyrazol-3-yl)-quinoline;
Phenyl-[4-(2-pyridin-2-yl-5,6-dihydro-4H-pyrrolo[1,2-b]pyrazol-3-yl)-quinolin-2-yl]-amine;
2-Methoxy-4-(2-pyridin-2-yl-5,6-dihydro-4H-pyrrolo[1,2-b]pyrazol-3-yl)-quinoline;
2-Ethoxy-4-(2-pyridin-2-yl-5,6-dihydro-4H-pyrrolo[1,2-b]pyrazol-3-yl)-quinoline;
4-[2-(6-Phenylsulfanyl-pyridin-2-yl)-5,6-dihydro-4H-pyrrolo[1,2-b]pyrazol-3-yl]-quinoline;
Phenyl-[6-(3-quinolin-4-yl-5,6-dihydro-4H-pyrrolo[1,2-b]pyrazol-2-yl)-pyridin-2-yl]-amine;
4-{2-[6-(4-Methoxy-phenyl)-pyridin-2-yl]-5,6-dihydro-4H-pyrrolo[1,2-b]pyrazol-3-yl}-quinoline;
4-[2-(6-Phenyl-pyridin-2-yl)-5,6-dihydro-4H-pyrrolo[1,2-b]pyrazol-3-yl]-quinoline;
4-[2-(6-Morpholin-4-yl-pyridin-2-yl)-5,6-dihydro-4H-pyrrolo[1,2-b]pyrazol-3-yl]-quinoline;
4-[2-(6-Pyrrolidin-1-yl-pyridin-2-yl)-5,6-dihydro-4H-pyrrolo[1,2-b]pyrazol-3-yl]-quinoline;
4-[2-(6-Methoxy-pyridin-2-yl)-5,6-dihydro-4H-pyrrolo[1,2-b]pyrazol-3-yl]-quinoline;
2-{3-[4-(2-Pyridin-2-yl-5,6-dihydro-4H-pyrrolo[1,2-b]pyrazol-3-yl)-quinolin-7-yloxy]-propyl}-isoindole-1,3-dione;
7-(3-Fluoro-propoxy)-4-(2-pyridin-2-yl-5,6-dihydro-4H-pyrrolo[1,2-b]pyrazol-3-yl)-quinoline;
7-(3-Fluoro-propoxy)-4-(2-pyridin-2-yl-5,6-dihydro-4H-pyrrolo[1,2-b]pyrazol-3-yl)-quinoline;
7-(3-Chloro-propoxy)-4-(2-pyridin-2-yl-5,6-dihydro-4H-pyrrolo[1,2-b]pyrazol-3-yl)-quinolin;
7-(3-Chloro-propoxy)-6-methoxy-4-(2-pyridin-2-yl-5,6-dihydro-4H-pyrrolo[1,2-b]pyrazol-3-yl)-quinoline;
7-(3-Chloro-propoxy)-4-[2-(6-methyl-pyridin-2-yl)-5,6-dihydro-4H-pyrrolo[1,2-b]pyrazol-3-yl]-quinoline;
(1-{3-[7-(2-Chloro-ethoxy)-quinolin-4-yl]-5,6-dihydro-4H-pyrrolo[1,2-b]pyrazol-2-yl}-propenyl)-methylene-amine;
N,N-Diethyl-2-[4-(2-pyridin-2-yl-5,6-dihydro-4H-pyrrolo[1,2-b]pyrazol-3-yl)-quinolin-7-yloxy]-acetamide;
7-[2-((2R)-1-Methyl-pyrrolidin-2-yl)-ethoxy]-4-(2-pyridin-2-yl-5,6-dihydro-4H-pyrrolo[1,2-b]pyrazol-3-yl)-quinoline;
Dimethyl-{4-[4-(2-pyridin-2-yl-5,6-dihydro-4H-pyrrolo[1,2-b]pyrazol-3-yl)-pyridin-2-yloxy]-butyl}-amine;
1-{3-[4-(2-Pyridin-2-yl-5,6-dihydro-4H-pyrrolo[1,2-b]pyrazol-3-yl)-pyridin-2-yloxy]-propyl}-pyrrolidin-2-one;
7-(1-Methyl-piperidin-3-ylmethoxy)-4-(2-pyridin-2-yl-5,6-dihydro-4H-pyrrolo[1,2-b]pyrazol-3-yl)-quinoline;
7-(3-N,N-Dimethylamino-2-methyl-propyloxy)-4-(2-pyridin-2-yl-5,6-dihydro-4H-pyrrolo[1,2-b]pyrazol-3-yl)-quinoline;
4-[2-(6-Methyl-pyridin-2-yl)-5,6-dihydro-4H-pyrrolo[1,2-b]pyrazol-3-yl]-7-propoxy-quinoline;
4-[6-Benzyloxymethyl-2-(6-methyl-pyridin-2-yl)-5,6-dihydro-4H-pyrrolo[1,2-b]pyrazol-3-yl]-quinoline;
{4-[2-(6-Methyl-pyridin-2-yl)-5,6-dihydro-4H-pyrrolo[1,2-b]pyrazol-3-yl]-quinolin-7-yloxy}-acetic acid methyl ester;
7-Isopropoxy-4-[2-(6-methyl-pyridin-2-yl)-5,6-dihydro-4H-pyrrolo[1,2-b]pyrazol-3-yl]-quinoline;
4-[2-(6-Methyl-pyridin-2-yl)-5,6-dihydro-4H-pyrrolo[1,2-b]pyrazol-3-yl]-7-(3-morpholin-4-yl-propoxy)-quinoline;
4-(6-Benzyloxymethyl-2-pyridin-2-yl-5,6-dihydro-4H-pyrrolo[1,2-b]pyrazol-6-yl)-quinoline;
7-Benzyloxy-2-Pyridin-2-yl-3-quinolin-4-yl-pyrazolo[1,5-a]piperidine;
2-[4-(2-pyridin-2-yl-5,6-dihydro-4H-pyrrolo[1,2-b]pyrazol-3-yl)-quinolin-7-yloxy]-acetamide;
7-(5-Phenyl-[1,2,4]oxadiazol-3-ylmethoxy)-4-(2-pyridin-2-yl-5,6-dihydro-4H-pyrrolo[1,2-b]pyrazol-3-yl)-quinoline;
7-(2,2-Difluoro-benzo[1,3]dioxol-5-ylmethoxy)-4-(2-pyridin-2-yl-5,6-dihydro-4H-pyrrolo[1,2-b]pyrazol-3-yl)-quinoline;
7-[2-((2S9-1-Methyl-pyrrolidin-2-yl)-ethoxy]-4-(2-pyridin-2-yl-5,6-dihydro-4H-pyrrolo[1,2-b]pyrazol-3-yl)-quinoline;
5-[4-(2-Pyridin-2-yl-5,6-dihydro-4H-pyrrolo[1,2-b]pyrazol-3-yl)-quinolin-7-yloxymethyl]-pyrrolidin-2-one;
4-(6-Phenoxymethyl-2-pyridin-2-yl-5,6-dihydro-4H-pyrrolo[1,2-b]pyrazol-3-yl)-quinoline;
4-(6-Methylene-2-pyridin-2-yl-5,6-dihydro-4H-pyrrolo[1,2-b]pyrazol-3-yl)-quinoline;
3-(4-Fluoro-phenyl)-6-methylene-2-(6-methyl-pyridin-2-yl)-5,6-dihydro-4H-pyrrolo[1,2-b]pyrazole;
7-(1-Methyl-piperidin-2-ylmethoxy)-4-(2-pyridin-2-yl-5,6-dihydro-4H-pyrrolo[1,2-b]pyrazol-3-yl)-quinoline hydrochloride;
7-[2-(1-Methyl-pyrrolidin-2-yl)-ethoxy]-4-(2-pyridin-2-yl-5,6-dihydro-4H-pyrrolo[1,2-b]pyrazol-3-yl)-quinoline hydrochloride;
4-[2-(6-Methyl-1-oxy-pyridin-2-yl)-5,6-dihydro-4H-pyrrolo[1,2-b]pyrazol-3-yl]-quinoline 1-oxide;
4-[2-(6-Methyl-pyridin-2-yl)-5,6-dihydro-4H-pyrrolo[1,2-b]pyrazol-3-yl]-quinoline 1-oxide;
4-[2-(6-Methyl-1-oxy-pyridin-2-yl)-5,6-dihydro-4H-pyrrolo[1,2-b]pyrazol-3-yl]-quinoline;
7-(3-Chloro-propoxy)-4-(2-pyridin-2-yl-5,6-dihydro-4H-pyrrolo[1,2-b]pyrazol-3-yl)-quinoline 1-oxide;
7-Methanesulfonyl-4-(2-pyridin-2-yl-5,6-dihydro-4H-pyrrolo[1,2-b]pyrazol-3-yl)-quinoline;
3-(4-Fluoro-phenyl)-2-(6-methyl-1-oxy-pyridin-2-yl)-5,6-dihydro-4H-pyrrolo[1,2-b]pyrazole;
4-(Quinolin-N-1-oxide-4-yl)-3-(6-methylpyridin-2-yl)-5,6-dihydro-4H-pyrrolo[1,2-b]pyrazole;

6-Methanesulfonyl-4-(2-pyridin-2-yl-5,6-dihydro-4H-pyrrolo[1,2-b]pyrazol-3-yl)-quinoline;

7-Ethanesulfonyl-4-(2-pyridin-2-yl-5,6-dihydro-4H-pyrrolo[1,2-b]pyrazol-3-yl)-quinoline;

4-(2-Pyridin-2-yl-5,6-dihydro-4H-pyrrolo[1,2-b]pyrazol-3-yl)-7-[3-(pyrimidine-2-sulfonyl)-propoxy]-quinoline;

7-[3-(1-Methyl-1H-imidazole-2-sulfonyl)-propoxy]-4-(2-pyridin-2-yl-5,6-dihydro-4H-pyrrolo[1,2-b]pyrazol-3-yl)-quinoline;

7-[3-(4-Chloro-benzenesulfonyl)-propoxy]-4-(2-pyridin-2-yl-5,6-dihydro-4H-pyrrolo[1,2-b]pyrazol-3-yl)-quinoline;

4-(2-Pyridin-2-yl-5,6-dihydro-4H-pyrrolo[1,2-b]pyrazol-3-yl)-7-[3-(pyridin-2-ylmethanesulfonyl)-propoxy]-quinoline;

4-(2-Pyridin-2-yl-5,6-dihydro-4H-pyrrolo[1,2-b]pyrazol-3-yl)-7-[3-(pyridin-2-ylmethanesulfonyl)-propoxy]-quinoline;

4-(Quinolin-1-N-oxide-4-yl)-3-(6-methylpyridin-2-yl-1-N-oxide)-5,6-dihydro-4H-pyrrolo[1,2-b]pyrazole;

3-{4-[2-(6-Methyl-pyridin-2-yl)-5,6-dihydro-4H-pyrrolo[1,2-b]pyrazol-3-yl]-quinolin-7-yl}-acrylic acid methyl ester;

3-{4-[2-(6-Methylpyridin-2-yl)-5,6-dihydro-4H-pyrrolo[1,2-b]pyrazol-3-yl]quinolin-7-yl}-1-piperidin-1-yl-propenone;

3-{4-[2-(6-Methyl-pyridin-2-yl)-5,6-dihydro-4H-pyrrolo[1,2-b]pyrazol-3-yl]-quinolin-6-yl}-acrylic acid methyl ester;

4-[2-(6-Methyl-pyridin-2-yl)-5,6-dihydro-4H-pyrrolo[1,2-b]pyrazol-3-yl]-7-vinyl-quinoline;

4-[2-(6-Benzyl-pyridin-2-yl)-5,6-dihydro-4H-pyrrolo[1,2-b]pyrazol-3-yl]-quinoline;

7-Benzyl-4-[2-(6-methyl-pyridin-2-yl)-5,6-dihydro-4H-pyrrolo[1,2-b]pyrazol-3-yl]-quinoline;

4-[2-(6-Methyl-pyridin-2-yl)-5,6-dihydro-4H-pyrrolo[1,2-b]pyrazol-3-yl]-quinoline-7-carboxylic acid;

4-[2-(6-Methyl-pyridin-2-yl)-5,6-dihydro-4H-pyrrolo[1,2-b]pyrazol-3-yl]-quinoline-6-carboxylic acid;

3-{4-[2-(6-Methyl-pyridin-2-yl)-5,6-dihydro-4H-pyrrolo[1,2-b]pyrazol-3-yl]-quinolin-7-yl}-acrylic acid;

3-{4-[2-(6-Methyl-pyridin-2-yl)-5,6-dihydro-4H-pyrrolo[1,2-b]pyrazol-3-yl]-quinolin-7-yl}-propionic acid;

4-[2-(6-Methyl-pyridin-2-yl)-3-quinolin-4-yl-5,6-dihydro-4H-pyrrolo[1,2-b]pyrazol-5-yl]-benzoic acid;

4-(2-Pyridin-2-yl-5,6-dihydro-4H-pyrrolo[1,2-b]pyrazol-3-yl)-quinoline-7-carboxylic acid cyclopentylamide;

4-(2-Pyridin-2-yl-5,6-dihydro-4H-pyrrolo[1,2-b]pyrazol-3-yl)-quinoline-7-carboxylic acid (2-morpholin-4-yl-ethyl)-amide;

4-(2-Pyridin-2-yl-5,6-dihydro-4H-pyrrolo[1,2-b]pyrazol-3-yl)-quinoline-7-carboxylic acid 2-(1H-imidazol-4-yl)-ethyl]-amide;

4-(2-Pyridin-2-yl-5,6-dihydro-4H-pyrrolo[1,2-b]pyrazol-3-yl)-quinoline-7-carboxylic acid (2-methylamino-ethyl)-amide;

4-(2-Pyridin-2-yl-5,6-dihydro-4H-pyrrolo[1,2-b]pyrazol-3-yl)-quinoline-7-carboxylic acid (3-methylamino-propyl)-amide;

4-(2-Pyridin-2-yl-5,6-dihydro-4H-pyrrolo[1,2-b]pyrazol-3-yl)-quinoline-7-carboxylic acid (2-dimethylamino-ethyl)-amide;

(4-Methyl-piperazine-I-yl)-[4-(2-pyridin-2-yl-5,6-dihydro-4H-pyrrolo[1,2-b]pyrazol-3-yl)-quinolin-7-yl]-methanone;

4-(2-Pyridin-2-yl-5,6-dihydro-4H-pyrrolo[1,2-b]pyrazol-3-yl)-quinoline-7-carboxylic acid cyclobutylamide;

4-(2-Pyridin-2-yl-5,6-dihydro-4H-pyrrolo[1,2-b]pyrazol-3-yl)-quinoline-7-carboxylic acid cyclopropylamide, 4-(2-Pyridin-2-yl-5,6-dihydro-4H-pyrrolo[1,2-b]pyrazol-3-yl)-quinoline-7-carboxylic acid (1-ethyl-propyl)-amide;

4-(2-Pyridin-2-yl-5,6-dihydro-4H-pyrrolo[1,2-b]pyrazol-3-yl)-quinoline-7-carboxylic acid ethylamide;

4-(2-Pyridin-2-yl-5,6-dihydro-4H-pyrrolo[1,2-b]pyrazol-3-yl)-quinoline-7-carboxylic acid isobutyl-amide;

4-(2-Pyridin-2-yl-5,6-dihydro-4H-pyrrolo[1,2-b]pyrazol-3-yl)-quinoline-7-carboxylic acid tert-butylamide;

4-(2-Pyridin-2-yl-5,6-dihydro-4H-pyrrolo[1,2-b]pyrazol-3-yl)-quinoline-7-carboxylic acid isopropylamide;

4-(2-Pyridin-2-yl-5,6-dihydro-4H-pyrrolo[1,2-b]pyrazol-3-yl)-quinoline-7-carboxylic acid propylamide;

4-(2-Pyridin-2-yl-5,6-dihydro-4H-pyrrolo[1,2-b]pyrazol-3-yl)-quinoline-7-carboxylic acid (2-methyl-butyl)-amide;

4-(2-Pyridin-2-yl-5,6-dihydro-4H-pyrrolo[1,2-b]pyrazol-3-yl)-quinoline-7-carboxylic acid ((2S)-2-methyl-butyl)-amide;

4-(2-Pyridin-2-yl-5,6-dihydro-4H-pyrrolo[1,2-b]pyrazol-3-yl)-quinoline-7-carboxylic acid (2S)-sec-butylamide;

4-(2-Pyridin-2-yl-5,6-dihydro-4H-pyrrolo[1,2-b]pyrazol-3-yl)-quinoline-7-carboxylic acid (2R)-sec-butylamide;

4-(2-Pyridin-2-yl-5,6-dihydro-4H-pyrrolo[1,2-b]pyrazol-3-yl)-quinoline-7-carboxylic acid ((IR)-1,2-dimethyl-propyl)-amide;

4-(2-Pyridin-2-yl-5,6-dihydro-4H-pyrrolo[1,2-b]pyrazol-3-yl)-quinoline-7-carboxylic acid (pyridin-4-ylmethyl)-amide;

4-(2-Pyridin-2-yl-5,6-dihydro-4H-pyrrolo[1,2-b]pyrazol-3-yl)-quinoline-7-carboxylic acid (pyridin-3-ylmethyl)-amide;

4-(2-Pyridin-2-yl-5,6-dihydro-4H-pyrrolo[1,2-b]pyrazol-3-yl)-quinoline-7-carboxylic acid (pyridin-2-ylmethyl)-amide;

6-(3-Quinolin-4-yl-5,6-dihydro-4H-pyrrolo[1,2-b]pyrazol-2-yl)-pyridine-2-carboxylic acid amide;

1-(4-Methyl-piperazin-1-yl)-2-[4-(2-pyridin-2-yl-5,6-dihydro-4H-pyrrolo[1,2-b]pyrazol-3-yl)-quinolin-7-yloxy]-ethanone;

N-(2-dimethylamino-ethyl)-2-[4-(2-pyridin-2-yl-5,6-dihydro-4H-pyrrolo[1,2-b]pyrazol-3-yl)-quinolin-7-yloxy]-acetamide;

N-(2-dimethylamino-ethyl)-N-methyl-2-[4-(2-pyridin-2-yl-5,6-dihydro-4H-pyrrolo[1,2-b]pyrazol-3-yl)-quinolin-7-yloxy]-acetamide;

N,N-Dimethyl-3-[4-(2-pyridin-2-yl-5,6-dihydro-4H-pyrrolo[1,2-b]pyrazol-3-yl)-quinolin-7-yloxy]-benzamide;

4-(2-Pyridin-2-yl-5,6-dihydro-4H-pyrrolo[1,2-b]pyrazol-3-yl)-quinoline-7-carboxylic acid amide;

4-(2-Pyridin-2-yl-5,6-dihydro-4H-pyrrolo[1,2-H]pyrazol-3-yl)-quinoline-7-carboxylic acid (2-dimethylamino-ethyl)-methyl-amide;

4-(2-Pyridin-2-yl-5,6-dihydro-4H-pyrrolo[1,2-H]pyrazol-3-yl)-quinoline-7-carboxylic acid (3-dimethylamino-propyl)-methyl-amide;

4-(2-Pyridin-2-yl-5,6-dihydro-4H-pyrrolo[1,2-H]pyrazol-3-yl)-quinoline-7-carboxylic acid dimethylamide;

4-(2-Pyridin-2-yl-5,6-dihydro-4H-pyrrolo[1,2-H]pyrazol-3-yl)-quinoline-7-carboxylic acid methylamide;

4-(2-Pyridin-2-yl-5,6-dihydro-4H-pyrrolo[1,2-b]pyrazol-3-yl)-quinoline-7-carboxylic acid pyridin-2-ylamide;

N-(2,2-Dimethylamino-ethyl)-N-methyl-3-{4-[2-(6-methyl-pyridin-2-yl)-5,6-dihydro-4H-pyrrolo[1,2-b]pyrazol-3-yl]-quinolin-7-yl}-propionamide;

2-(6-Methyl-pyridin-2-yl)-5,6-dihydro-4H-pyrrolo[1,2-b]
pyrazol-3-yl)-quinoline-6-carboxylic acid (2-dimethylamino-ethyl)-amide;
4-[2-(6-Methyl-pyridin-2-yl)-5,6-dihydro-4H-pyrrolo[1,2-b]pyrazol-3-yl]-quinoline-6-carboxylic acid (3-dimethylamino-propyl)-amide;
4-[2-(6-Methyl-pyridin-2-yl)-5,6-dihydro-4H-pyrrolo[1,2-b]pyrazol-3-yl]-quinoline-6-carboxylic acid (2-morpholin-4-yl-ethyl)-amide;
1-[2-(Quinolin-4-yl)-1-(6-methyl-pyridin-2-yl)-5,6-dihydro-4H-pyrrolo[1,2-b]pyrazol-3-yl]quinoline-7-carboxylic acid N,N-dimethylaminoethylamide;
4-[2-(6-Methylpyridin-2-yl)-5,6-dihydro-4H-pyrrolo[1,2-b]pyrazol-3-yl]quinoline-7-carbox-ylic acid (2-piperidin-1-yl-ethyl)amide;
N-(2-Dimethylamino-ethyl)-3-{4-[2-(6-methyl-pyridin-2-yl)-5,6-dihydro-4H-pyrrolo[1,2-b]pyrazol-3-yl]-quinolin-7-yl}-propionamide;
4-[2-(6-Methyl-pyridin-2-yl)-5,6-dihydro-4H-pyrrolo[1,2-b]pyrazol-3-yl]-quinoline-7-carboxylic acid (3-dimethylamino-propyl)-amide;
4-(2-(6-Methyl-pyridin-2-yl)-5,6-dihydro-4H-pyrrolo[1,2-b]pyrazol-3-yl]-quinoline-7-carboxylic acid (3-pyrrolidin-1-yl-propyl)-amide;
4-(6-Methyl-pyridin-2-yl)-5,6-dihydro-4H-pyrrolo[1,2-b]pyrazol-3-yl]-quinoline-7-carboxylic acid (3-morpholin-4-yl-propyl)-amide;
3-{4-[2-(6-Methyl-pyridin-2-yl)-5,6-dihydro-4H-pyrrolo[1,2-b]pyrazol-3-yl]-quinolin-7-yl}-propionamide;
4-(2-Pyridin-2-yl-5,6-dihydro-4H-pyrrolo[1,2-b]pyrazol-3-yl)-quinoline-6-carboxylic acid (2-dimethylamino-ethyl)-amide;
4-(2-Pyridin-2-yl-5,6-dihydro-4H-pyrrolo[1,2-b]pyrazol-3-yl)-quinoline-6-carboxylic acid (2-morpholin-4-yl-ethyl)-amide;
4-(2-Pyridin-2-yl-5,6-dihydro-4H-pyrrolo[1,2-b]pyrazol-3-yl)-quinoline-6-carboxylic acid;
4-(2-Pyridin-2-yl-5,6-dihydro-4H-pyrrolo[1,2-b]pyrazol-3-yl)-quinoline-6-carboxylic acid hydrazide;
4-(2-Pyridin-2-yl-5,6-dihydro-4H-pyrrolo[1,2-b]pyrazol-3-yl)-quinoline-6-carboxylic acid amide;
4-(2-Pyridin-2-yl-5,6-dihydro-4H-pyrrolo[1,2-b]pyrazol-3-yl)-quinoline-6-carboxylic acid (3-methylamino-propyl)-amide;
4-(2-Pyridin-2-yl-5,6-dihydro-4H-pyrrolo[1,2-b]pyrazol-3-yl)-quinoline-6-carboxylic acid amide;
4-(2-Pyridin-2-yl-5,6-dihydro-4H-pyrrolo[1,2-b]pyrazol-3-yl)-quinoline-6-carboxylic acid (2-hydroxy-ethyl)-amide;
4-(2-Pyridin-2-yl-5,6-dihydro-4H-pyrrolo[1,2-b]pyrazol-3-yl)-quinoline-7-carboxylic acid hydrazide;
4-(2-Pyridin-2-yl-5,6-dihydro-4H-pyrrolo[1,2-b]pyrazol-3-yl)-. quinoline-7-carboxylic acid hydroxyamide;
4-(2-Pyridin-2-yl-5,6-dihydro-4H-pyrrolo[1,2-b]pyrazol-3-yl)-quinoline-7-carboxylic acid (2-amino-ethyl)-amide;
4-(2-Pyridin-2-yl-5,6-dihydro-4H-pyrrolo[1,2-b]pyrazol-3-yl)-quinoline-7-carboxylic acid (2-hydroxy-ethyl)-amide;
4-(2-Pyridin-2-yl-5,6-dihydro-4H-pyrrolo[1,2-b]pyrazol-3-yl)-quinoline-7-sulfonic acid amide;
4-(2-Pyridin-2-yl-5,6-dihydro-4H-pyrrolo[1,2-b]pyrazol-3-yl)-quinoline-7-sulfonic acid methylamide;
4-(2-Pyridin-2-yl-5,6-dihydro-4H-pyrrolo[1,2-b]pyrazol-3-yl)-quinoline-7-sulfonic acid dimethylamide;
4-(2-Pyridin-2-yl-5,6-dihydro-4H-pyrrolo[1,2-b]pyrazol-3-yl)-quinoline-7-sulfonic acid (3-dimethylamino-propyl)-amide;
4-(2-Pyridin-2-yl-5,6-dihydro-4H-pyrrolo[1,2-b]pyrazol-3-yl)-quinoline-7-sulfonic acid diethylamide;
4-(2-Pyridin-2-yl-5,6-dihydro-4H-pyrrolo[1,2-b]pyrazol-3-yl)-quinoline-7-sulfonic acid (2-piperidin-1-yl-ethyl)-amide;
4-(2-Pyridin-2-yl-5,6-dihydro-4H-pyrrolo[1,2-b]pyrazol-3-yl)-quinoline-7-sulfonic acid (2-hydroxy-ethyl)-amide;
4-(2-Pyridin-2-yl-5,6-dihydro-4H-pyrrolo[1,2-b]pyrazol-3-yl)-quinolin-7-ylamine;
2-Dimethylamino-N-[4-(2-pyridin-2-yl-5,6-dihydro-4H-pyrrolo[1,2-b]pyrazol-3-yl)-quinolin-7-yl]-acetamide;
3-Dimethylamino-N-[4-(2-pyridin-2-yl-5,6-dihydro-4H-pyrrolo[1,2-b]pyrazol-3-yl)-quinolin-7-yl]propionamide;
N-[4-(2-Pyridin-2-yl-5,6-dihydro-4H-pyrrolo[1,2-b]pyrazol-3-yl)-quinolin-7-yl]-methanesulfonamide;
N-[4-(2-Pyridin-2-yl-5,6-dihydro-4H-pyrrolo[1,2-b]pyrazol-3-yl)-quinolin-7-yl]-acetamide;
4-(2-Pyridin-2-yl-5,6-dihydro-4H-pyrrolo[1,2-b]pyrazol-3-yl)-quinoline-7-carboxylic acid (2-acetylamino-ethyl)-amide;
N-{3-[4-(2-Pyridin-2-yl-5,6-dihydro-4H-pyrrolo[1,2-b]pyrazol-3-yl)-quinolin-7-yloxy]-propyl}-methanesulfonamide;
1-methyl-1H-imidazole-4-sulfonic acid{3-[4-(2-pyridin-2-yl-5,6-dihydro-4H-pyrrolo[1,2-b]pyrazol-3-yl)-quinolin-7-yloxy]-propyl}-amide;
1-(2-Dimethylamino-ethyl)-3-[4-(2-pyridin-2-yl-5,6-dihydro-4H-pyrrolo[1,2-b]pyrazol-3-yl)-quinolin-7-yl]-urea;
1-(3-Dimethylamino-propyl)-3-[4-(2-pyridin-2-yl-5,6-dihydro-4H-pyrrolo[1,2-b]pyrazol-3-yl)-quinolin-7-yl]-urea;
1-(3-Hydroxy-ethyl)-3-[4-(2-pyridin-2-yl-5,6-dihydro-4H-pyrrolo[1,2-b]pyrazol-3-yl)-quinolin-7-yl]-urea;
[4-(2-Pyridin-2-yl-5,6-dihydro-4H-pyrrolo[1,2-b]pyrazol-3-yl)-quinolin-7-yl]-carbamic acid methyl ester;
[4-(2-Pyridin-2-yl-5,6-dihydro-4H-pyrrolo[1,2-b]pyrazol-3-yl)-quinolin-7-yl]-carbamic acid 2-hydroxy-ethyl ester;
[4-(2-Pyridin-2-yl-5,6-dihydro-4H-pyrrolo[1,2-b]pyrazol-3-yl)-quinolin-7-yl]-carbamic acid 2-methoxy-ethyl ester;
1,3-Bis-[4-(2-pyridin-2-yl-5,6-dihydro-4H-pyrrolo[1,2-b]pyrazol-3-yl)-quinolin-7-yl]-urea;
Dimethyl-carbamic acid 4-(2-pyridin-2-yl-5,6-dihydro-4H-pyrrolo[1,2-b]pyrazol-3-yl)-quinolin-7-yl ester;
7-Bromo-2-isopropyl-4-(2-pyridin-2-yl-5,6-dihydro-4H-pyrrolo[1,2-b]pyrazol-3-yl)-quinoline;
2-{4-[2-(6-Methyl-pyridin-2-yl-5,6-dihydro-4H-pyrrolo[1,2-b]pyrazol-3-yl]-quinolin-6-yl}-propan-2-ol;
7-(3-Chloro-propylsulfanyl)-4-(2-pyridin-2-yl-5,6-dihydro-4H-pyrrolo[1,2-b]pyrazol-3-yl)-quinoline;
7-Bromo-4-(4-chloro-2-pyridin-2-yl-5,6-dihydro-4H-pyrrolo[1,2-b]pyrazol-3-yl)-quinoline;
8-Chloro-4-(2-Pyridin-2-yl-5,6-dihydro-4H-pyrrolo[1,2-b]pyrazol-3-yl)-quinolin-7-ol;
8-Bromo-4-(2-pyridin-2-yl-5,6-dihydro-4H-pyrrolo[1,2-b]pyrazol-3-yl)-quinolin-7-ol;
3-(7-Bromo-quinolin-4-yl)-2-pyridin-2-yl-5,6-dihydro-4H-pyrrolo[1,2-b]pyrazol-4-ol;
7-Bromo-4-(4-methoxy-2-pyridin-2-yl-5,6-dihydro-4H-pyrrolo[1,2-b]pyrazol-3-yl)-quinoline;
[3-(7-Bromo-quinolin-4-yl)-2-pyridin-2-yl-5,6-dihydro-4H-pyrrolo[1,2-b]pyrazol-4-yl]-methyl-amine;
3-(7-Bromo-quinolin-4-yl)-2-pyridin-2-yl-5,6-dihydro-pyrrolo[1,2-b]pyrazol-4-one;
3-[4-(2-Pyridin-2-yl-5,6-dihydro-4H-pyrrolo[1,2-b]pyrazol-3-yl)-quinolin-7-yloxy]-benzamide;
N,N-Dimethyl-3-[4-(2-pyridin-2-yl-5,6-dihydro-4H-pyrrolo[1,2-b]pyrazol-3-yl)-quinolin-7-yloxy]-thiobenzamide;
Dimethyl-{3-[4-(2-Pyridin-2-yl-5,6-dihydro-4H-pyrrolo[1,2-b]pyrazol-3-yl)-quinolin-7-yloxy]-benzyl}-amine;

4-(2-(6-Methyl-pyridin-2-yl-5,6-dihydro-4H-pyrrolo[1,2-b]pyrazol-3-yl]-1H-quinolin-2-one;
4-(2-Pyridin-2-yl-5,6-dihydro-4H-pyrrolo[1,2-b]pyrazol-3-yl)-quinolin-7-ol;
4-[2-(6-Methyl-pyridin-2-yl)-5,6-dihydro-4H-pyrrolo[1,2-b]pyrazol-3-yl]-quinolin-7-ol;
6-Methoxy-4-(2-pyridin-2-yl-5,6-dihydro-4H-pyrrolo[1,2-b]pyrazol-3-yl)-quinolin-7-ol;
3-{4-[2-(6-Methyl-pyridin-2-yl)-5,6-dihydro-4H-pyrrolo[1,2-b]pyrazol-3-yl]-quinolin-7-yl}-propionic acid methyl ester;
4-(6-(Methyl-2-pyridin-2-yl-5,6-dihydro-4H-pyrrolo[1,2-b]pyrazol-3-yl)-quinoline;
3-{4-[2-(6-Methyl-pyridin-2-yl)-5,6-dihydro-4H-pyrrolo[1,2-b]pyrazol-3-yl]-quinolin-6-yl}-propionic acid methyl ester;
7-Amino-4-[2-(6-Methyl-pyridin-2-yl)-5,6-dihydro-4H-pyrrolo[1,2-b]pyrazol-3-yl]-quinoline;
N,N-Dimethyl-3-{4-(2-methyl-pyridin-2-yl-5,6-dihydro-4H-pyrrolo[1,2-b]pyrazol-3-yl)-quinolin-7-yl}-propionamide;
N-{3-[4-(2-Pyridin-2-yl-5,6-dihydro-4H-pyrrolo[1,2-b]pyrazol-3-yl)-quinolin-7-yloxy]-propyl}-acetamide;
N-Acetyl-N-{4-[2-(6-methyl-pyridin-2-yl)-5,6-dihydro-4H-pyrrolo[1,2-b]pyrazol-3-yl]-quinolin-7-yl}-acetamide,
2-Pyridin-2-yl-3-quinolin-4-yl-pyrazolo[1,5-a]piperidin-7-ol;
7-Acetoxy-2-pyridin-2-yl-3-quinolin-4-yl-pyrazol[1,5-a]piperidine;
Methyl-{3-[4-(2-pyridin-2-yl-5,6-dihydro-4H-pyrrolo[1,2-b]pyrazol-3-yl)-quinolin-7-yloxy]-propyl}-amine;
7-(Piperidin-4-yloxy)-4-(2-pyridin-2-yl-5,6-dihydro-4H-pyrrolo[1,2-b]pyrazol-3-yl)-quinoline;
4-(6-(Methyl-2-pyridin-2-yl)-5,6-dihydro-4H-pyrrolo[1,2-b]pyrazol-3-yl]-quinoline-7-carboxylic acid (2-amino-1,1-dimethyl-ethyl)-amide;
16-[3-(4-Fluoro-phenyl)-5,6-dihydro-4H-pyrrolo[1,2-b]pyrazol-2-yl]-pyridin-2-yl}-methanol,rrrrrm-rrrrr) [6-(3-Quinolin-4-yl-5,6-dihydro-4H-pyrrolo[1,2-b]pyrazol-2-yl)-pyridin-2-yl]-methanol;
4-(6-(Methyl-2-pyridin-2-yl)-5,6-dihydro-4H-pyrrolo[1,2-b]pyrazol-3-yl]-phenol;
7-(1-Methyl-pyrrolidin-3-ylmethoxy)-4-(2-pyridin-2-yl-5,6-dihydro-4H-pyrrolo[1,2-b]pyrazol-3-yl)-quinoline;
7-(1-Methyl-piperidin-4-ylmethoxy)-4-(2-pyridin-2-yl-5,6-dihydro-4H-pyrrolo[1,2-b]pyrazol-3-yl)-quinoline;
4-[2-(6-Methyl-pyridin-2-yl)-5,6-dihydro-4H-pyrrolo[1,2-b]pyrazol-3-yl]-quinoline-7-carboxylic acid (2-dimethylamino-1,1-dimethyl-ethyl)-amide;
(S)-[3-(4-Fluoro-phenyl)-2-(6-methyl-pyridin-2-yl)-5,6-dihydro-4H-pyrrolo[1,2-b]pyrazol-6-yl]-methanol;
(R)-[3-(4-Fluoro-phenyl)-2-(6-methyl-pyridin-2-yl)-5,6-dihydro-4H-pyrrolo[1,2-b]pyrazol-6-yl]-methanol;
(S)-[3-(4-Fluoro-phenyl)-2-(6-methyl-pyridin-2-yl)-5,6-dihydro-4H-pyrrolo[1,2-b]pyrazol-6-yl]-acetonitrile;
(R)-[3-(4-Fluoro-phenyl)-2-(6-methyl-pyridin-2-yl)-5,6-dihydro-4H-pyrrolo[1,2-b]pyrazol-6-yl]-acetonitrile;
4-(3-Pyridin-2-yl-5,6-dihydro-4H-pyrrolo[1,2-b]pyrazol-2-yl)-quinoline;
4-(6-Pyridin-2-yl-2,3-dihydro-pyrazolo[5,1-b]oxazol-7-yl)-quinoline;
3-[4-(2-Pyridin-2-yl-5,6-dihydro-4H-pyrrolo[1,2-b]pyrazol-3-yl)-quinolin-7-yl]-oxazolidin-2-one;
1-[4-(2-Pyridin-2-yl-5,6-dihydro-4H-pyrrolo[1,2b]pyrazol-3-yl)-quinolin-7-yl]-imidazolidin-2-one;
4-(2-Pyridin-2-yl-5,6-dihydro-4H-pyrrolo[1,2-b]pyrazol-3-yl)-7-(pyridin-4-ylmethoxy)-quinoline;
4-(2-Pyridin-2-yl-5,6-dihydro-4H-pyrrolo[1,2-b]pyrazol-3-yl)-7-(3-pyridin-3-yl-propoxy)-quinoline;
7-(4,5-Dihydro-1H-imidazol-2-yl)-4-(2-pyridin-2-yl-5,6-dihydro-4H-pyrrolo[1,2-b]pyrazol-3-yl)-quinoline;
4-[5-(4-Fluoro-phenyl)-2-(6-methyl-pyridin-2-yl)-5,6-dihydro-4H-pyrrolo[1,2-b]pyrazol-3-yl]-quinoline (Enantiomer A);
4-[5-(4-Fluoro-phenyl)-2-(6-methyl-pyridin-2-yl)-5,6-dihydro-4H-pyrrolo[1,2-b]pyrazol-3-yl]-quinoline (Enantiomer B);
2-Pyridin-2-yl-3-quinolin-4-yl-pyrazolo[5,1-c]morpholine;
4-[2-(6-Vinyl-pyridin-2-yl)-5,6-dihydro-4H-pyrrolo[1,2-b]pyrazol-3-yl]-quinoline;
3-{4-[2-(6-Methyl-pyridin-2-yl)-5,6-dihydro-4H-pyrrolo[1,2-b]pyrazol-3-yl]-quinolin-6-yl}-acrylic acid;
7-(6-Methyl-pyridin-3-yloxy)-4-(2-pyridin-2-yl-5,6-dihydro-4H-pyrrolo[1,2-b]pyrazol-3-yl)-quinoline;
4-(2-Pyridin-2-yl-5,6-dihydro-4H-pyrrolo[1,2-b]pyrazol-3-yl)-7-[4-(4-pyrimidin-2-yl-piperazin-1-yl)-butoxy]-quinoline;
7-[3-[4-(2-Methoxy-phenyl)-piperazin-1-yl]-propoxy}-4-(2-pyridin-2-yl-5,6-dihydro-4H-pyrrolo[1,2-b]pyrazol-3-yl)-quinoline;
Pyridin-2-yl-{3-[4-(2-pyridin-2-yl-5,6-dihydro-4H-pyrrolo[1,2-b]pyrazol-3-yl)-quinolin-7-yloxy]-propyl}-amine;
4-(6-(Methyl-pyridin-2-yl)-5,6-dihydro-4H-pyrrolo[1,2-b]pyrazol-3-yl]-quinoline-7-carboxylic acid (2-dimethylamino-1-methyl-ethyl)-amide, rrrrnTn-rr) 4-[2-(6-Methyl-pyridin-2-yl)-5,6-dihydro-4H-pyrrolo[1,2-b]pyrazol-3-yl]-quinoline-7-carboxylic acid amide;
4-(2-Pyridin-2-yl-5,6-dihydro-4H-pyrrolo[1,2-b]pyrazol-3-yl)-quinoline-7-carboxylic acid (3-dimethylamino-propyl)-amide;
4-[2-(6-Methyl-pyridin-2-yl)-5,6-dihydro-4H-pyrrolo[1,2-b]pyrazol-3-yl]-quinoline-7-carboxylic acid (2-dimethylamino-ethyl)-methyl-amide;
N,N-Dimethyl-3-{4-[2-(6-methyl-pyridin-2-yl)-5,6-dihydro-4H-pyrrolo[1,2-b]pyrazol-3-yl]-quinolin-7-yl}-acrylamide;
4-(2-Pyridin-2-yl-5,6-dihydro-4H-pyrrolo[1,2-b]pyrazol-3-yl)-quinoline 1-oxide;
7-Benzyloxy-4-[2-(6-methyl-pyridin-2-yl)-5,6-dihydro-4H-pyrrolo[1,2-b]pyrazol-3-yl]-quinoline;
4-(2-(6-Chloro-6-dihydro-4H-pyrrolo-pyridin-2-yl)-5[1,2-b]pyrazol-3-yl)-quinoline;
6-(3-Quinolin-4-yl-5,6-dihydro-4H-pyrrolo[1,2-b]pyrazol-2-yl)pyridine-2-carboxylic acid methyl ester;
4-(7-Chloroquinolin-4-yl)-3-(pyridin-2-yl)-5,6-dihydro-4H-pyrrolo[1,2#b]pyrazole;
4-(2-Furan-2-yl-5,6-dihydro-4H-pyrrolo[1,2-b]pyrazol-3-yl)-quinoline;
3-{4-(6-Methyl-pyridin-2-yl)-5,6-dihydro-4H-pyrrolo[1,2-b]pyrazol-3-yl]-quinolin-6-yl}-acrylic acid methyl ester;
4-[2-(2-Methyl-thiazol-4-yl)-5,6-dihydro-4H-pyrrolo[1,2-b]pyrazol-3-yl]-quinoline;
3-(4-Fluoro-phenyl)-2-(2-methyl-thiazol-4-yl)-5,6-dihydro-4H-pyrrolo[1,2-b]pyrazole;
4-[2-(2-Methyl-2H-pyrazol-3-yl)-5,6-dihydro-4H-pyrrolo[1,2-b]pyrazol-3-yl]-quinoline;
4-(2-Thiazol-2-yl-5,6-dihydro-4H-pyrrolo[1,2-b]pyrazol-3-yl)-quinoline;
4-[2-(1-Methyl-1H-imidazol-2-yl-5,6-dihydro-4H-pyrrolo[1,2-b]pyrazol-3-yl]-quinoline;
6,7-Dichloro-4-[2-(6-methyl-pyridin-2-yl)-5,6-dihydro-4H-pyrrolo[1,2-b]pyrazol-3-yl]-quinoline;
(S)-6-Benzyloxymethyl-3-(4-fluoro-phenyl)-2-(6-methyl-pyridin-2-yl)-5,6-dihydro-4H-pyrrolo[1,2-b]pyrazole;

N,N-Dimethyl-3-{4-[2-(6-methyl-pyridin-2-yl)-5,6-dihydro-4H-pyrrolo[1,2-b]pyrazol-3-yl]-quinolin-7-yl}-acrylamide;

3-methyl-6-[2-[6-methyl-(pyridin-2-yl)]-5,6-di-hydro-4H-pyrrolo[1,2-b]pyrazol-3-yl]-3H-quinazolin-4-one;

1-methyl-7-[2-[6-methyl-(pyridin-2-yl)]-5,6-di-hydro-4H-pyrrolo[1,2-b]pyrazol-3-yl]-1H-quinoxalin-2-one;

3-methyl-6-[2-(pyridin-2-yl)-5,6-dihydro-4H-pyrrolo[1,2-b]pyrazol-3-yl]-3H-quinazolin-4-one;

3-methyl-6-[2-[6-pentyl-(pyridin-2-yl)]-5,6-di-hydro-4H-pyrrolo[1,2-b]pyrazol-3-yl]-3H-quinazolin-4-one;

6-[2-[6-Methyl-(pyridin-2-yl)]-5,6-dihydro-4H-pyrrolo[1,2-b]pyrazol-3-yl]-4H-benzo[1,4]oxazin-3-one;

3-(2-Chloro-ethyl)-6-[2-[6-methyl-(pyridin-2-yl)]-5,6-dihydro-4H-pyrrolo[1,2-b]pyrazol-3-yl]-3H-quinazolin-4-one;

6-[2-[6-methyl-(pyridin-2-yl)]-5,6-dihydro-4H-pyrrolo[1,2-b]pyrazol-3-yl]-3-(2-morpholin-4-yl-ethyl)-3H-quinazolin-4-one;

3-(2-Dimethylamino-ethyl)-6-[2-[6-methyl-(py-ridin-2-yl)]-5,6-dihydro-4H-pyrrolo[1,2-b]pyrazol-3-yl]-3H-quinazolin-4-one;

6-[2-[6-Methyl-(pyridin-2-yl)]-5,6-dihydro-4H-pyrrolo[1,2-b]pyrazol-3-yl]-3-(2-piperidin-1-yl-ethyl)-3H-quinazolin-4-one;

6-[2-[6-Methyl-(pyridin-2-yl)]-5,6-dihydro-4H-pyrrolo[1,2-b]pyrazol-3-yl]-3-(2-pyrrolidin-1-yl-ethyl)-3H-quinazolin-4-one;

3-(2-Azepan-1-yl-ethyl)-6-[2-[6-methyl-(pyridin-2-yl)]-5,6-dihydro-4H-pyrrolo[1,2-b]pyrazol-3-yl]-3H-quinazolin-4-one;

7-[2-[6-Methyl-(pyridin-2-yl)]-5,6-dihydro-4H-pyrrolo[1,2-b]pyrazol-3-yl]-1-(2-pyrrolidin-1-yl-ethyl)-3,4-dihydro-1H-quinoxalin-2-one; and 1-(2-Dimethylamino-ethyl)-7-[2-[6-methyl-(pyridin-2-yl)]-5,6-dihydro-4H-pyrrolo[1,2-b]pyrazol-3-yl]-3,4-dihydro-1H-quinoxalin-2-one.

In one aspect, the TGF-β inhibitor has the structure shown in formula (II)

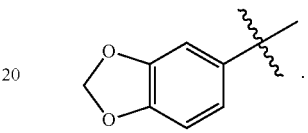

Formula (II)

wherein $R^1$ is cyclyl, heterocyclcyl, aryl or heteroaryl, each of which can be optionally substituted;

$R^2$ is cyclyl, heterocyclcyl, aryl or heteroaryl, each of which can be optionally substituted;

$R^3$ is cyclyl, heterocyclcyl, aryl, heteroaryl or —S(O)alkyl, each of which can be optionally substituted;

$R^4$ is H, optionally substituted $C_1$-$C_6$ alkyl, optionally substituted $C_2$-$C_6$ alkenyl, optionally substituted $C_2$-$C_6$ alkynyl, or $R^3$ and $R^4$ together with the atoms they are attached to form a cyclyl, heterocyclyl, aryl or heteroaryl, each of which can be optionally substituted.

In some embodiments, $R^1$ is aryl, e.g., a substituted aryl. In some embodiments, $R^1$ is substituted with two substituents. In some embodiments, $R^1$ is substituted with two substituents, which together with the carbons to which they are attached form a ring. In some embodiments, $R^1$ is a substituted phenyl. In some embodiments, $R^1$ is a nitrogen containing heteroaryl (e.g., including 1, 2, or 3 nitrogens (e.g., 1 or)). In some embodiments, $R^1$ is a bicyclic heteroaryl. In some embodiments, $R^1$ is a 6-6 fused heteroaryl. In some embodiments, $R^1$ is pyridyl, pyrimidyl, pyridazinyl, pyrazinyl, quinolinyl, naphthyridinyl (e.g., 1,5-naphthyridinyl), quinazolinyl, 5,6,7,8-tetrahydroquinazolinyl, 1,3-benzodioxlyl, 1,2,3-benzotriazolyl, benzoxazolyl, benzothiazolyl, 2,1,3-benzooxadiazole, imidazo[1,2-a]pyridinyl, pyrazolo[1,5-a]pyridinyl, [1,2,4]triazolo[1,5-a]pyridinyl, pyrazolo[1,5-a]pyrimidinyl, [1,2,4]triazolo[1,5-a]pyrimidinyl, [1,2,3]triazolo[1,5-a]pyrimidinyl, [1,2,4]triazolo[4,3-a]pyrimidinyl, [1,2,4]triazolo[4,3-a]pyridazinyl. In some embodiments, $R^1$ is

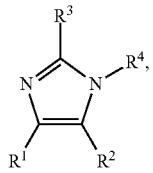

In some embodiments, $R^2$ is aryl, e.g., a substituted aryl. In some embodiments, $R^2$ is a nitrogen comprising heteroaryl (e.g., including 1, 2 or 3 nitrogens (e.g., 1 or 2)). In some embodiments, $R^2$ is an optionally substituted monocyclic heteroaryl (e.g., a six membered heteroaryl such as pyridyl, pyrimidyl, pyridazinyl or pyrazinyl). In some embodiments, $R^2$ is substituted. Exemplary substituents include halo, $C_1$-$C_6$ alkyl, halo$C_1$-$C_6$alkyl, $C_1$-$C_6$ alkoxy, OH, halo$C_1$-$C_6$alkoxy. In some embodiments, $R^2$ is monosubstituted. In some embodiments, $R^2$ is substituted with methyl. In one embodiment, $R^2$ is an optionally substituted pyridyl. In some embodiments, $R^2$ is

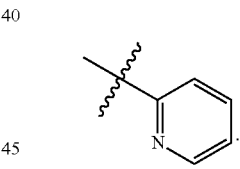

In some embodiments, $R^3$ is aryl, e.g., a substituted aryl. In some embodiments, $R^3$ is substituted with two substituents, which together with the carbons to which they are attached form a ring. In some embodiments, $R^3$ is a substituted phenyl. In some embodiments, $R^3$ is a nitrogen containing heteroaryl (e.g., including 1, 2, or 3 nitrogens (e.g., 1 or)). In some embodiments, $R^3$ is a bicyclic heteroaryl. In some embodiments, $R^3$ is a 6-6 fused heteroaryl. In some embodiments, $R^3$ is pyridyl, pyrimidyl, pyridazinyl, pyrazinyl, quinolinyl, naphthyridinyl (e.g., 1,5-naphthyridinyl), quinazolinyl, 5,6,7,8-tetrahydroquinazolinyl, 1,3-benzodioxlyl, 1,2,3-benzotriazolyl, benzoxazolyl, benzothiazolyl, 2,1,3-benzooxadiazole, imidazo[1,2-a]pyridinyl, pyrazolo[1,5-a]pyridinyl, [1,2,4]triazolo[1,5-a]pyridinyl, pyrazolo[1,5-a]pyrimidinyl, [1,2,4]-triazolo[1,5-a]pyrimidinyl, [1,2,3]triazolo[1,5-a]pyrimidinyl, [1,2,4]triazolo[4,3-a]pyrimidinyl, [1,2,4]triazolo[4,3-a]pyridazinyl. In some embodiments, $R^3$ is monosubstituted. In some embodiments, $R^3$ is an optionally substituted phenyl. In some embodiments, $R^3$ is

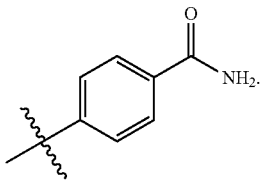 [SMILES: *c1ccc(C(N)=O)cc1]

In some embodiment, $R^4$ is H.

In some embodiments, the compound of formula (II) has the structure shown in formula (IIa):

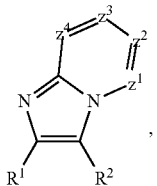

Formula (IIa)

wherein $z^1$-$z^4$ are independently $CR^5$ or N; $R^5$ is H, benzyl, aryl, heteroaryl, $C_1$-$C_6$alkyl, alkenyl, alkynyl, halogen, amino, —C(O)-amino, —$SO_2$-alkyl, —O-alkyl or acyl, each of which can be optionally substituted, provided that no two N are not next to each other.

In some embodiments, one of $z^2$ or $z^3$ is N.

In some embodiments, the compound of formula (II) has the structure shown in formula (IIb):

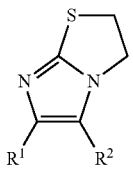

Formula (IIb)

Exemplary compounds of formula (II) include

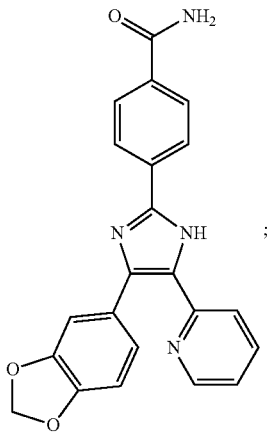 [SMILES: NC(=O)c1ccc(-c2nc(-c3ccc4c(c3)OCO4)c(-c3ccccn3)[nH]2)cc1]

6-(2-(6-methylpyridin-2-yl)H-imidazo[1,2-a]pyridin-3-yl)-N-(3-(piperidin-1-yl)propyl)pyridin-2-amine;

3-isopropyl-6-(5-(6-methylpyridin-2-yl)-2H-1,2,3-triazol-4-yl)H-imidazo[1,2-a]pyridine;

1-(3-((pyridin-3-yl)methoxy)-4-carbamoylisothiazol-5-yl)-3-(3,5-dimethoxybenzyl)urea;

(2-Methoxy-ethyl)-{4-[2-(6-methyl-pyridin-2-yl)-imidazo-[1,2-a]pyridin-3-yl]-pyrimidin-2-yl}-amine;

(3-{4-[2-(6-Methyl-pyridin-2-yl)-imidazo[1,2-a]pyridin-3-yl]-pyrimidin-2-ylamino}-propyl)-carbamic acid tert-butyl ester;

(3-Imidazol-1-yl-propyl)-{4-[2-(6-methyl-pyridin-2-yl)-imidazo[1,2-a]pyridin-3-yl]-pyrimidin-2-yl}-amine;

(4-Methoxy-benzyl)-{4-[2-(6-methyl-pyridin-2-yl)-imidazo[1,2-a]pyridin-3-yl]-pyrimidin-2-yl}-amine;

[2-(6-Methyl-pyridin-2-yl)-3-(2-methylsulfanyl-pyrimidin-4-yl)-imidazo[1,2-a]pyridin-6-yl]-methanol;

3-(2-Methanesulfonyl-pyrimidin-4-yl)-2-(6-methyl-pyridin-2-yl)-imidazo[1,2-a]pyridine;

(4-4-[2-(6-Methyl-pyridin-2-yl)-imidazo[1,2-a]pyridin-3-yl]-pyrimidin-2-ylamino}-butyl)-carbamic acid tert-butyl ester;

(4-Amino-benzyl)-{4-[2-(6-methyl-pyridin-2-yl)-imidazo[1,2-a]pyridin-3-yl]-pyrimidin-2-yl}-amine;

(5-{4-[2-(6-Methyl-pyridin-2-yl)-imidazo[1,2-a]pyridin-3-yl]-pyrimidin-2-ylamino}-pentyl)-carbamic acid tert-butyl ester;

[3-(2-Amino-pyrimidin-4-yl)-2-(6-methyl-pyridin-2-yl)-imidazo[1,2-a]pyridin-6-yl]-methanol;

[3-(2-amino-pyrimidin-4-yl)-2-(6-methyl-pyridin-2-yl)-imidazo[1,2-a]pyridin-7-yl]-methanol;

[3-(2-Amino-pyrimidin-4-yl)-6-methyl-2-(6-methyl-pyridin-2-yl)-imidazo[1,2-a]pyridin-8-yl]-(2-morpholin-4-yl-ethyl)-amine;

[3-(2-Amino-pyrimidin-4-yl)-6-methyl-2-(6-methyl-pyridin-2-yl)-imidazo[1,2-a]pyridin-8-yl]-(2-pyridin-2-yl-ethyl)-amine;

[3-(2-Amino-pyrimidin-4-yl)-6-methyl-2-(6-methyl-pyridin-2-yl)-imidazo[1,2-a]pyridin-8-yl]-(2-pyridin-3-yl-ethyl)-amine;

[3-(2-methanesulfonyl-pyrimidin-4-yl)-2-(6-methyl-pyridin-2-yl)-imidazo[1,2-a]pyridin-6-yl]-methanol;

[3-(2-Amino-pyrimidin-4-yl)-6-methyl-2-(6-methyl-pyridin-2-yl)-imidazo[1,2-a]pyridin-8-yl]-(2-pyridin-4-yl-ethyl)-amine;

[3-(2-Amino-pyrimidin-4-yl)-6-methyl-2-(6-methyl-pyridin-2-yl)-imidazo[1,2-a]pyridin-8-yl]-(3-morpholin-4-yl-propyl)-amine;

[3-(4-Methyl-piperazin-1-yl)-propyl]-{4-[2-(6-methyl-pyridin-2-yl)-imidazo[1,2-a]pyridin-3-yl]-pyrimidin-2-yl}-amine;

[3-(4-Methyl-piperidin-1-yl)-propyl]-{4-[2-(6-methyl-pyridin-2-yl)-imidazo[1,2-a]pyridin-3-yl]-pyrimidin-2-yl}-amine;

[4-(2-Pyridin-2-yl-imidazo[1,2-a]pyridin-3-yl)-pyrimidin-2-yl]-pyridin-3-ylmethyl-amine;

{4-[2-(6-Methyl-pyridin-2-yl)-imidazo[1,2-a]pyridin-3-yl]-pyrimidin-2-yl}-(R)-1-phenyl-ethyl)-amine;

{4-[2-(6-Methyl-pyridin-2-yl)-imidazo[1,2-a]pyridin-3-yl]-pyrimidin-2-yl}-(S)-1-phenyl-ethyl)-amine;

{4-[2-(6-Methyl-pyridin-2-yl)-imidazo[1,2-a]pyridin-3-y]-pyrimidin-2-yl}-(1H-tetrazol-5-yl) -amine;

{4-[2-(6-Methyl-pyridin-2-yl)-imidazo[1,2-a]pyridin-3-yl]-pyrimidin-2-yl}-(2H-pyrazol-3-yl) -amine;

{4-[2-(6-Methyl-pyridin-2-yl)-imidazo[1,2-a]pyridin-3-yl]-pyrimidin-2-yl}-(2-morpholin-4-yl-ethyl)-amine;

{4-[2-(6-Methyl-pyridin-2-yl)-imidazo[1,2-a]pyridin-3-yl]-pyrimidin-2-yl}-(2-pyridin-2-yl-ethyl)-amine;

{4-[2-(6-Methyl-pyridin-2-yl)-imidazo[1,2-a]pyridin-3-yl]-pyrimidin-2-yl}-(2-pyridin-3-yl-ethyl)-amine;

{4-[2-(6-Methyl-pyridin-2-yl)-imidazo[1,2-a]pyridin-3-yl]-pyrimidin-2-yl}-(2-pyridin-4-yl-ethyl)-amine;
{4-[2-(6-Methyl-pyridin-2-yl)-imidazo[1,2-a]pyridin-3-yl]-pyrimidin-2-yl}-(3-morpholin-4-yl-propyl)-amine;
{4-[2-(6-Methyl-pyridin-2-yl)-imidazo[1,2-a]pyridin-3-yl]-pyrimidin-2-yl}-(3-piperidin-1-yl-propyl)-amine;
{4-[2-(6-Methyl-pyridin-2-yl)-imidazo[1,2-a]pyridin-3-yl]-pyrimidin-2-yl}-[1,3,4]thiadiazol-2-yl-amine;
2-(6-Methyl-pyridin-2-yl)-3-(2-methylsulfanyl-pyrimidin-4-yl)-imidazo[1,2-a]pyridine;
2-(6-Methyl-pyridin-2-yl)-3-(2-methylsulfanyl-pyrimidin-4-yl)-imidazo[1,2-a]pyridine-6-carboxylic acid methyl ester;
2-(6-Methyl-pyridin-2-yl)-3-(2-methylsulfanyl-pyrimidin-4-yl)-imidazo[1,2-a]pyridine-7-carboxylic acid ethyl ester;
2-(6-Methyl-pyridin-2-yl)-3-(2-methylsulfanyl-pyrimidin-4-yl)-imidazo[1,2-a]pyrimidin-7-ylamine;
{7,7-Dimethyl-8-[5-(4-4-[2-(6-methyl-pyridin-2-yl)-imidazo[1,2-a]pyridin-3-yl]-pyrimidin-2-ylamino}-butylcarbamoyl)-pentyl]-2-oxo-4-trifluoromethyl-7,8-dihydro-2H-1-oxa-8-aza-anthracen-5-yl}-methanesulfonic acid;
2-(2,7-Difluoro-6-hydroxy-3-oxo-9,9a-dihydro-3H-xanthen-9-yl)-3,5,6-trifluoro-4-[(4-{4-[2-(6-methyl-pyridin-2-yl)-imidazo[1,2-a]pyridin-3-yl]-pyrimidin-2-ylamino}-butylcarbamoyl)-methylsulfanyl]-benzoic acid;
2-(6-Methyl-pyridin-2-yl)-3-(2-morpholin-4-yl-pyrimidin-4-yl)-imidazo[1,2-a]pyridine;
2-(6-Methyl-pyridin-2-yl)-3-(2-piperidin-1-yl-pyrimidin-4-yl)-imidazo[1,2-a]pyridine;
2-(6-Methyl-pyridin-2-yl)-3-(2-pyrrolidin-1-yl-pyrimidin-4-yl)-imidazo[1,2-a]pyridine;
2-(6-Methyl-pyridin-2-yl)-3-[2-(1H-tetrazol-5-yl)-pyrimidin-4-yl]-imidazo[1,2-a]pyridine;
2-(6-Methyl-pyridin-2-yl)-3-pyrimidin-4-yl-imidazo[1,2-a]pyridine;
2-(6-Methyl-pyridin-2-yl)-3-pyrimidin-4-yl-imidazo[1,2-a]pyrimidin-7-ylamine;
3-(2-Amino-pyrimidin-4-yl)-2-(6-methyl-pyridin-2-yl)-imidazo[1,2-a]pyridin-8-ylamine;
3-(2-Amino-pyrimidin-4-yl)-2-(6-methyl-pyridin-2-yl)-imidazo[1,2-a]pyridine-6-carbonitrile;
3-(2-Amino-pyrimidin-4-yl)-2-(6-methyl-pyridin-2-yl)-imidazo[1,2-a]pyridine-6-carboxylic acid;
3-(2-Amino-pyrimidin-4-yl)-2-(6-methyl-pyridin-2-yl)-imidazo[1,2-a]pyridine-6-carboxylic acid ([1,4]dioxan-2-ylmethyl)-amide;
3-(2-Amino-pyrimidin-4-yl)-2-(6-methyl-pyridin-2-yl)-imidazo[1,2-a]pyridine-6-carboxylic acid ([1,4]dioxan-2-ylmethyl)-amide;
3-(2-Amino-pyrimidin-4-yl)-2-(6-methyl-pyridin-2-yl)-imidazo[1,2-a]pyridine-6-carboxylic acid (2-dimethylamino-ethyl)-amide;
3-(2-Amino-pyrimidin-4-yl)-2-(6-methyl-pyridin-2-yl)-imidazo[1,2-a]pyridine-6-carboxylic acid (2-methoxy-ethyl)-amide;
3-(2-Amino-pyrimidin-4-yl)-2-(6-methyl-pyridin-2-yl)-imidazo[1,2-a]pyridine-6-carboxylic acid (2-thiophen-2-yl-ethyl)-amide;
3-(2-Amino-pyrimidin-4-yl)-2-(6-methyl-pyridin-2-yl)-imidazo[1,2-a]pyridine-6-carboxylic acid [3-(4-methyl-piperazin-1-yl)-propyl]amide;
3-(2-Amino-pyrimidin-4-yl)-2-(6-methyl-pyridin-2-yl)-imidazo[1,2-a]pyridine-6-carboxylic acid amide;
3-(2-Amino-pyrimidin-4-yl)-2-(6-methyl-pyridin-2-yl)-imidazo[1,2-a]pyridine-6-carboxylic acid cyclopropylamide;
3-(2-Amino-pyrimidin-4-yl)-2-(6-methyl-pyridin-2-yl)-imidazo[1,2-a]pyridine-6-carboxylic acid ethylamide;
3-(2-Amino-pyrimidin-4-yl)-2-(6-methyl-pyridin-2-yl)-imidazo[1,2-a]pyridine-6-carboxylic acid hydroxyamide;
3-(2-Amino-pyrimidin-4-yl)-2-(6-methyl-pyridin-2-yl)-imidazo[1,2-a]pyridine-6-carboxylic acid methoxy-amide;
3-(2-Amino-pyrimidin-4-yl)-2-(6-methyl-pyridin-2-yl)-imidazo[1,2-a]pyridine-6-carboxylic acid methyl ester;
3-(2-Amino-pyrimidin-4-yl)-2-(6-methyl-pyridin-2-yl)-imidazo[1,2-a]pyridine-7-carboxylic acid;
3-(2-Amino-pyrimidin-4-yl)-2-(6-methyl-pyridin-2-yl)-imidazo[1,2-a]pyridine-7-carboxylic acid [1,4]dioxan-2-ylmethyl)-amide;
3-(2-Amino-pyrimidin-4-yl)-2-(6-methyl-pyridin-2-yl)-imidazo[1,2-a]pyridine-7-carboxylic acid (2-amino-ethyl)-amide;
3-(2-Amino-pyrimidin-4-yl)-2-(6-methyl-pyridin-2-yl)-imidazo[1,2-a]pyridine-7-carboxylic acid (2-dimethylamino-ethyl)-amide;
3-(2-Amino-pyrimidin-4-yl)-2-(6-methyl-pyridin-2-yl)-imidazo[1,2-a]pyridine-7-carboxylic acid (2-hydroxy-ethyl)-amide;
3-(2-Amino-pyrimidin-4-yl)-2-(6-methyl-pyridin-2-yl)-imidazo[1,2-a]pyridine-7-carboxylic acid (2-oxo-2-pyridin-3-yl-ethyl)-amide;
3-(2-Amino-pyrimidin-4-yl)-2-(6-methyl-pyridin-2-yl)-imidazo[1,2-a]pyridine-7-carboxylic acid (2-thiophen-2-yl-ethyl)-amide;
3-(2-Amino-pyrimidin-4-yl)-2-(6-methyl-pyridin-2-yl)-imidazo[1,2-a]pyridine-7-carboxylic acid (piperidin-3-ylmethyl)-amide;
3-(2-Amino-pyrimidin-4-yl)-2-(6-methyl-pyridin-2-yl)-imidazo[1,2-a]pyridine-7-carboxylic acid 2,2-dimethylhydrazide;
3-(2-Amino-pyrimidin-4-yl)-2-(6-methyl-pyridin-2-yl)-imidazo[1,2-a]pyridine-7-carboxylic acid amide;
3-(2-Amino-pyrimidin-4-yl)-2-(6-methyl-pyridin-2-yl)-imidazo[1,2-a]pyridine-7-carboxylic acid cyclopropylamide;
3-(2-Amino-pyrimidin-4-yl)-2-(6-methyl-pyridin-2-yl)-imidazo[1,2-a]pyridine-7-carboxylic acid ethyl ester;
3-(2-Amino-pyrimidin-4-yl)-2-(6-methyl-pyridin-2-yl)-imidazo[1,2-a]pyridine-7-carboxylic acid ethylamide;
3-(2-Amino-pyrimidin-4-yl)-2-(6-methyl-pyridin-2-yl)-imidazo[1,2-a]pyridine-7-carboxylic acid hydroxyamide;
3-(2-Amino-pyrimidin-4-yl)-2-(6-methyl-pyridin-2-yl)-imidazo[1,2-a]pyridine-7-carboxylic acid methoxy-amide;
3-(2-Amino-pyrimidin-4-yl)-2-(6-methyl-pyridin-2-yl)-imidazo[1,2-a]pyrimidin-7-ylamine;
3-(2-Azetidin-1-yl-pyrimidin-4-yl)-2-(6-methyl-pyridin-2-yl)-imidazo[1,2-a]pyridine;
3-(2-Methanesulfonyl-pyrimidin-4-yl)-2-(6-methyl-pyridin-2-yl)-imidazo[1,2-a]pyridine-7-carboxylic acid ethyl ester;
3-(2-Methanesulfonyl-pyrimidin-4-yl)-2-(6-methyl-pyridin-2-yl)-imidazo[1,2-a]pyridine-6-carboxylic acid methyl ester;
3-(2-Methanesulfonyl-pyrimidin-4-yl)-7-methyl-2-(6-methyl-pyridin-2-yl)-imidazo[1,2-a]pyridine;
3-(2-Methanesulfonyl-pyrimidin-4-yl)-8-methyl-2-(6-methyl-pyridin-2-yl)-imidazo[1,2-a]pyridine;
3,3-Dimethyl-N-[2-(6-methyl-pyridin-2-yl)-3-(2-methylsulfanyl-pyrimidin-4-yl)-imidazo[1,2-a]pyrimidin-7-yl]-butyramide;
3-(2-Methanesulfonyl-pyrimidin-4-yl)-2-(6-methyl-pyridin-2-yl)-imidazo[1,2-a]pyridine-6-carbonitrile;
3-(2-Methylsulfanyl-pyrimidin-4-yl)-2-pyridin-2-yl-imidazo[1,2-a]pyridine;

3,6-Dichloro-N-(4-{4-[2-(6-methyl-pyridin-2-yl)-imidazo [1,2-a]pyridin-3-yl]-pyrimidin-2-ylamino}-butyl)-2-(2,4, 5,7-Tetrachloro-6-hydroxy-3-oxo-9,9a-dihydro-3H-xanthen-9-yl)-terephthalamic acid;

3-[2-(2-Methyl-aziridin-1-yl)-pyrimidin-4-yl]-2-(6-methyl-pyridin-2-yl)-imidazo[1,2-a]pyridine;

3-[2-(4-Methyl-piperazin-1-yl)-pyrimidin-4-yl]-2-(6-methyl-pyridin-2-yl)-imidazo[1,2-a]pyridine;

3-{[3-(2-Amino-pyrimidin-4-yl)-2-(6-methyl-pyridin-2-yl)-imidazo[1,2-a]pyridine-6-carbonyl]-amino}-propionic acid methyl ester;

3-{[3-(2-Amino-pyrimidin-4-yl)-2-(6-methyl-pyridin-2-yl)-imidazo[1,2-a]pyridine-7-carbonyl]-amino}-propionic acid methyl ester;

3-{4-[2-(6-Methyl-pyridin-2-yl)-imidazo[1,2-a]pyridin-3-yl]-pyrimidin-2-ylamino}-phenol;

4-(2-{4-[2-(6-Methyl-pyridin-2-yl)-imidazo[1,2-a]pyridin-3-yl]-pyrimidin-2-ylamino}-ethyl)-benzenesulfonamide;

4-(2-Pyridin-2-yl-imidazo[1,2-a]pyridin-3-yl)-pyrimidin-2-ylamine;

4-[2-(6-Chloro-pyridin-2-yl)-imidazo[1,2-a]pyridin-3-yl]-pyrimidin-2-ylamine;

4-[2-(6-Methyl-pyridin-2-yl)-7-trifluoromethyl-imidazo[1,2-a]pyridin-3-yl]-pyrimidin-2-ylamine;

4-[2-(6-Methyl-pyridin-2-yl)-imidazo[1,2-a]pyridin-3-yl]-pyrimidin-2-ylamine;

4-[2-(6-Methyl-pyridin-2-yl)-imidazo[1,2-a]pyridin-3-yl]-pyrimidine-2-carbonitrile;

4-[2-(6-Methyl-pyridin-2-yl)-imidazo[1,2-a]pyridin-3-yl]-pyrimidine-2-carboxylic acid amide;

4-[6-Bromo-2-(6-methyl-pyridin-2-yl)-imidazo[1,2-a]pyridin-3-yl]-pyrimidin-2-ylamine;

4-[6-Chloro-2-(6-methyl-pyridin-2-yl)-imidazo[1,2-a]pyridin-3-yl]-pyrimidin-2-ylamine;

4-[6-Fluoro-2-(6-methyl-pyridin-2-yl)-imidazo[1,2-a]pyridin-3-yl]-pyrimidin-2-ylamine;

4-[6-Methyl-2-(6-methyl-pyridin-2-yl)-8-(2-morpholin-4-yl-ethylamino)-imidazo[1,2-a]pyridin-3-yl]-pyrimidin-2-ol;

4-[6-Methyl-2-(6-methyl-pyridin-2-yl)-8-(2-pyridin-2-yl-ethylamino)-imidazo[1,2-a]pyridin-3-yl]-pyrimidin-2-ol;

4-[6-Methyl-2-(6-methyl-pyridin-2-yl)-8-(2-pyridin-3-yl-ethylamino)-imidazo[1,2-a]pyridin-3-yl]-pyrimidin-2-ol;

4-[6-Methyl-2-(6-methyl-pyridin-2-yl)-8-(2-pyridin-4-yl-ethylamino)-imidazo[1,2-a]pyridin-3-yl]-pyrimidin-2-ol;

4-[6-Methyl-2-(6-methyl-pyridin-2-yl)-8-morpholin-4-yl-imidazo[1,2-a]pyridin-3-yl]-pyrimidin-2-ol;

4-[6-Methyl-2-(6-methyl-pyridin-2-yl)-8-morpholin-4-yl-imidazo[1,2-a]pyridin-3-yl]-pyrimidin-2-ylamine;

4-[6-Methyl-2-(6-methyl-pyridin-2-yl)-imidazo[1,2-a]pyridin-3-yl]-pyrimidin-2-ylamine;

4-[7-Aminomethyl-2-(6-methyl-pyridin-2-yl)-imidazo[1,2-a]pyridin-3-yl]-pyrimidin-2-ylamine;

4-[7-Methyl-2-(6-methyl-pyridin-2-yl)-imidazo[1,2-a]pyridin-3-yl]-pyrimidin-2-ylamine;

4-[8-Benzyloxy-2-(6-methyl-pyridin-2-yl)-imidazo[1,2-a]pyridin-3-yl]-pyrimidin-2-ol;

4-[8-Benzyloxy-2-(6-methyl-pyridin-2-yl)-imidazo[1,2-a]pyridin-3-yl]-pyrimidin-2-ylamine;

4-[8-Bromo-6-methyl-2-(6-methyl-pyridin-2-yl)-imidazo[1,2-a]pyridin-3-yl]-pyrimidin-2-ol;

4-[8-Methyl-2-(6-methyl-pyridin-2-yl)-imidazo[1,2-a]pyridin-3-yl]-pyrimidin-2-ylamine;

6-Chloro-3-(2-methanesulfonyl-pyrimidin-4-yl)-2-(6-methyl-pyridin-2-yl)-imidazo[1,2-a]pyridine;

5-Dimethylamino-naphthalene-1-sulfonic acid (4-{4-[2-(6-methyl-pyridin-2-yl)-imidazo[1,2-a]pyridin-3-yl]-pyrimidin-2-ylamino}-butyl)-amide;

6-(2,7-Difluoro-6-hydroxy-3-oxo-3H-xanthen-9-yl)-N-(4-{4-[2-(6-methyl-pyridin-2-yl)-imidazo[1,2-a]pyridin-3-yl]-pyrimidin-2-ylamino}-butyl)-isophthalamic acid;

6-Amino-9-[2-carboxy-5-(4-{4-[2-(6-methyl-pyridin-2-yl)-imidazo[1,2-a]pyridin-3-yl]-pyrimidin-2-ylamino}-butyl-carbamoyl)-phenyl]-xanthen-3-ylidene-ammonium;

6-Bromo-2-(6-methyl-pyridin-2-yl)-3-(2-methylsulfanyl-pyrimidin-4-yl)-imidazo[1,2-a]pyridine;

6-Fluoro-2-(6-methyl-pyridin-2-yl)-3-(2-methylsulfanyl-pyrimidin-4-yl)-imidazo[1,2-a]pyridine;

7-Amino-4-methyl-3-[(4-{4-[2-(6-methyl-pyridin-2-yl)-imidazo[1,2-a]pyridin-3-yl]-pyrimidin-2-ylamino}-butyl-carbamoyl)-methyl]-2-oxo-2H-chromene-6-sulfonic acid;

Cyclobutyl-{4-[2-(6-methyl-pyridin-2-yl)-imidazo[1,2-a]pyridin-3-yl]-pyrimidin-2-yl}-amine;

Cyclopentyl-{4-[2-(6-methyl-pyridin-2-yl)-imidazo[1,2-a]pyridin-3-yl]-pyrimidin-2-yl}-amine;

Cyclopropyl-{4-[2-(6-methyl-pyridin-2-yl)-imidazo[1,2-a]pyridin-3-yl]-pyrimidin-2-yl}-amine;

Cyclopropyl-methyl-{4-[2-(6-methyl-pyridin-2-yl)-imidazo[1,2-a]pyridin-3-yl]-pyrimidin-2-yl}-amine;

Dimethyl-{4-[2-(6-methyl-pyridin-2-yl)-imidazo[1,2-a]pyridin-3-yl]-pyrimidin-2-yl}-amine;

Isopropyl-4-[2-(6-methyl-pyridin-2-yl)-imidazo[1,2-a]pyridin-3-yl]-pyrimidin-2-yl}-amine;

Methyl-{4-[2-(6-methyl-pyridin-2-yl)-imidazo[1,2-a]pyridin-3-yl]-pyrimidin-2-yl}-amine;

N-(2-{4-[2-(6-Methyl-pyridin-2-yl)-imidazo[1,2-a]pyridin-3-yl]-pyrimidin-2-ylamino}-ethyl)-acetamide;

N-(4-{4-[2-(6-Methyl-pyridin-2-yl)-imidazo[1,2-a]pyridin-3-yl]-pyrimidin-2-ylamino}-butyl)-acetamide;

N,N-Dimethyl-N'-{4-[2-(6-methyl-pyridin-2-yl)-imidazo[1,2-a]pyridin-3-yl]-pyrimidin-2-yl}-ethane-1,2-diamine;

N-[2-(6-Methyl-pyridin-2-yl)-3-(2-methylsulfanyl-pyrimidin-4-yl)-imidazo[1,2-a]pyrimidin-7-yl]-3-pyridin-3-yl-propionamide;

N-[2-(6-Methyl-pyridin-2-yl)-3-(2-methylsulfanyl-pyrimidin-4-yl)-imidazo[1,2-a]pyrimidin-7-yl]-nicotinamide;

N-[2-(6-Methyl-pyridin-2-yl)-3-(2-methylsulfanyl-pyrimidin-4-yl)-imidazo[1,2-a]pyrimidin-7-yl]-propionamide;

N-[3-(2-Amino-pyrimidin-4-yl)-2-(6-methyl-pyridin-2-yl)-imidazo[1,2-a]pyridine-6-carbonyl]-methanesulfonamide;

N-[3-(2-Amino-pyrimidin-4-yl)-2-(6-methyl-pyridin-yl)-imidazo[1,2-a]pyridine-7-carbonyl]-methanesulfonamide;

N-[3-(2-Amino-pyrimidin-4-yl)-2-(6-methyl-pyridin-2-yl)-imidazo[1,2-a]pyrimidin-7-yl]-2-(3-methoxy-phenyl)-acetamide;

N-[3-(2-Amino-pyrimidin-4-yl)-2-(6-methyl-pyridin-2-yl)-imidazo[1,2-a]pyrimidin-7-yl]-3,3-dimethyl-butyramide;

N-[3-(2-Amino-pyrimidin-4-yl)-2-(6-methyl-pyridin-2-yl)-imidazo[1,2-a]pyrimidin-7-yl]-3-pyridin-3-yl-propionamide;

N-[3-(2-Amino-pyrimidin-4-yl)-2-(6-methyl-pyridin-2-yl)-imidazo[1,2-a]pyrimidin-7-yl]-acetamide;

N-[3-(2-Amino-pyrimidin-4-yl)-2-(6-methyl-pyridin-2-yl)-imidazo[1,2-a]pyrimidin-7-yl]-nicotinamide;

N-[3-(2-Methanesulfonyl-pyrimidin-4-yl)-2-(6-methyl-pyridin-2-yl)-imidazo[1,2-a]pyrimidin-7-yl]-2-(3-methoxy-phenyl)-acetamide;

N-[3-(2-Methanesulfonyl-pyrimidin-4-yl)-2-(6-methyl-pyridin-2-yl)-imidazo[1,2-a]pyrimidin-7-yl]-3,3-dimethyl-butyramide;

N-[3-(2-Methanesulfonyl-pyrimidin-4-yl)-2-(6-methyl-pyridin-2-yl)-imidazo[1,2-a]pyrimidin-7-yl]-3-pyridin-3-yl-propionamide;

N-[3-(2-Methanesulfonyl-pyrimidin-4-yl)-2-(6-methyl-pyridin-2-yl)-imidazo[1,2-a]pyrimidin-7-yl]-nicotinamide;

N-[3-(2-Methanesulfonyl-pyrimidin-4-yl)-2-(6-methyl-pyridin-2-yl)-imidazo[1,2-a]pyrimidin-7-yl]-propionamide;

N-[3-(2-Amino-pyrimidin-4-yl)-2-(6-methyl-pyridin-2-yl)-imidazo[1,2-a]pyrimidin-7-yl]-propionamide;

N-{4-[2-(6-Methyl-pyridin-2-yl)-imidazo[1,2-a]pyridin-3-yl]-pyrimidin-2-yl}-acetamide;

N1-{4-[2-(6-Methyl-pyridin-2-yl)-imidazo[1,2-a]pyridin-3-yl]-pyrimidin-2-yl}-butane-1,4-diamine;

N1-{4-[2-(6-Methyl-pyridin-2-yl)-imidazo[1,2-a]pyridin-3-yl]-pyrimidin-2-yl}-propane-1,3-diamine;

N-(4-{4-[2-(6-Methyl-pyridin-2-yl)-imidazo[1,2-a]pyridin-3-yl]-pyrimidin-2-ylamino}-butyl)-(BODIPY FL)amide; and N-(4-{4-[2-(6-Methyl-pyridin-2-yl)-imidazo[1,2-a]pyridin-3-yl]-pyrimidin-2-ylamino}-butyl)- (Texas Red-X)amide.

In one aspect, the TGF-β inhibitor has the structure shown in formula (IIIa):

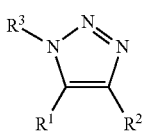

Formula (IIIa)

or formula (IIIb)

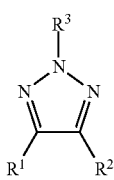

Formula (IIIb)

wherein:

$R^1$ is cyclyl, heterocyclcyl, aryl or heteroaryl, each of which can be optionally substituted;

$R^2$ is cyclyl, heterocyclcyl, aryl or heteroaryl, each of which can be optionally substituted;

$R^3$ is $R^3$ is H, $C_1$-$C_6$ alkyl, $C_2$-$C_6$ alkenyl, $C_2$-$C_6$ alkynyl, aryl, heteroaryl, cyclyl, heterocyclyl, acyl or a nitrogen protecting group, each of which can be optionally substituted.

In some embodiments, $R^1$ is a nitrogen containing heteroaryl (e.g., including 1, 2, or 3 nitrogens (e.g., 1 or)). In some embodiments, $R^1$ is a bicyclic heteroaryl. In some embodiments, $R^1$ is a 6-6 fused heteroaryl. In some embodiments, $R^1$ is pyridyl, pyrimidyl, quinolinyl, naphthyridinyl (e.g., 1,5-naphthyridinyl), quinazolinyl, 5,6,7,8-tetrahydroquinazolinyl, 1,3-benzodioxlyl, 1,2,3-benzotriazolyl, benzoxazolyl, benzothiazolyl, 2,1,3-benzooxadiazole, imidazo[1,2-a]pyridinyl, pyrazolo[1,5-a]pyridinyl, [1,2,4]triazolo[1,5-a]pyridinyl, pyrazolo[1,5-a]pyrimidinyl, [1,2,4]triazolo[1,5-a]pyrimidinyl, [1,2,3]triazolo[1,5-a]pyrimidinyl, [1,2,4]triazolo[4,3-a]pyrimidinyl, [1,2,4]triazolo[4,3-a]pyridazinyl. In some embodiments, $R^1$ is

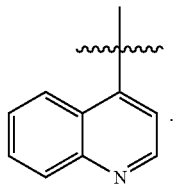 [SMILES: *c1ccnc2ccccc12]

In some embodiments, $R^1$ is

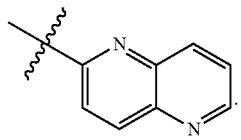 [SMILES: *c1ccc2ncccc2n1]

In some embodiments, $R^2$ is aryl, e.g., a substituted aryl. In some embodiments, $R^2$ is a nitrogen comprising heteroaryl (e.g., including 1, 2 or 3 nitrogens (e.g., 1 or 2)). In some embodiments, $R^2$ is an optionally substituted monocyclic heteroaryl (e.g., a six membered heteroaryl such as pyridyl, pyrimidyl, pyridazinyl or pyrazinyl). In some embodiments, $R^2$ is substituted. Exemplary substituents include halo, $C_1$-$C_6$ alkyl, halo$C_1$-$C_6$alkyl, $C_1$-$C_6$ alkoxy, OH, halo$C_1$-$C_6$alkoxy. In some embodiments, $R^2$ is monosubstituted. In some embodiments, $R^2$ is substituted with methyl. In one embodiment, $R^2$ is an optionally substituted pyridyl. In some embodiments, $R^2$ is

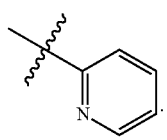

In some embodiments, $R^2$ is

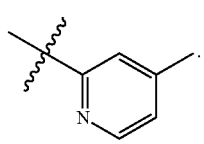 [SMILES: *c1cc(C)ccn1]

In one aspect, the TGF-β inhibitor has the structure shown in formula (IV):

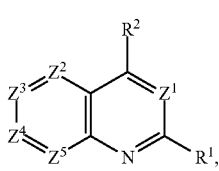

Formula (IV)

wherein:

$R^1$ is H, $C_1$-$C_6$ alkyl, $C_1$-$C_6$ alkenyl, $C_1$-$C_6$ alkynyl, aryl, heteroaryl, cyclyl, optionally substituted heterocyclyl or acyl, each of which can be optionally substituted;

$R^2$ is H, $C_1$-$C_6$ alkyl, $C_1$-$C_6$ alkenyl, $C_1$-$C_6$ alkynyl, aryl, heteroaryl, cyclyl, optionally substituted heterocyclyl, acyl or amino (e.g., $N(R^3)_2$), each of which can be optionally substituted;

$R^3$ is independently for each occurrence H, $C_1$-$C_6$ alkyl, $C_1$-$C_6$ alkenyl, $C_1$-$C_6$ alkynyl, aryl, heteroaryl, cyclyl, optionally substituted heterocyclyl or acyl, each of which can be optionally substituted;

$Z^1$, $Z^2$, $Z^3$, $Z^4$ and $Z^5$ are each independently N or $CR^3$, provided that at least two of $Z^2$, $Z^3$, $Z^4$ and $Z^5$ are $CR^3$, and further provided that two adjacent Z positions are not N.

In one embodiment, $R^1$ is aryl, e.g., a substituted aryl. In one embodiment, $R^1$ is phenyl. In one embodiment, $R^1$ is phenyl substituted with at least one halogen.

In one embodiment, $R^2$ is $NHR^3$.

Exemplary compounds of formula (IV) include:
2-phenyl-4-(4-pyridylamino)-quinazoline;
2-(2-bromophenyl)-4-(4-pyridylamino)-quinazoline;
2-(2-chlorophenyl)-4-(4-pyridylamino)-quinazoline;
2-(2-fluorophenyl)-4-(4-pyridylamino)-quinazoline;
2-(2-methylphenyl)-4-(4-pyridylamino)-quinazoline;
2-(4-fluorophenyl)-4-(4-pyridylamino)-quinazoline;
2-(3-methoxyanilyl)-4-(4-pyridylamino)-quinazoline;
2-(2,6-dichlorophenyl)-4-(4-pyridylamino)-quinazoline;
2-(2,6-dibromophenyl)-4-(4-pyridylamino)-quinazoline;
2-(2,6-difluorophenyl)-4-(4-pyridylamino)-quinazoline;
2-(2-fluorophenyl)-4-(6-pyridylamino)-6,7-dimethoxyquinazoline;
2-(4-fluorophenyl)-4-(4-pyridylamino)-6,7-dimethoxyquinazoline;
2-(2-fluorophenyl)-4-(4-pyridylamino)-6-nitroquinazoline;
2-(2-fluorophenyl)-4-(4-pyridylamino-6-aminoquinazoline;
2-(2-fluorophenyl)-4-(4-pyridylamino)-7-aminoquinazoline;
2-(2-fluorophenyl)-4-(4-pyridylamino)-6-(3-methoxybenzylamino)-quinazoline;
2-(2-fluorophen)-4-(4-pyridylamino)-6-(4-methoxybenzylamino)-quinazoline;
2-(2-fluorophenyl)-4-(4-pyridyla17nino)-6-(2-isobutylamino)-quinazoline; and
2-(2-fluorophenyl)-4-(4-pyridylamino)-6-(4-methylmercaptobenzylamino)-quinazoline.

In one aspect, the disclosure features a method of producing an iPS cell from a somatic cell, the method comprising:

In one aspect, the TGF-β inhibitor has the structure shown in formula (V):

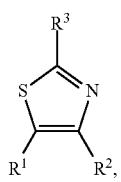

Formula (V)

wherein:
$R^1$ is H, $C_1$-$C_6$ alkyl, $C_1$-$C_6$ alkenyl, $C_1$-$C_6$ alkynyl, aryl, heteroaryl, cyclyl, optionally substituted heterocyclyl or acyl, each of which can be optionally substituted;

$R^2$ is H, $C_1$-$C_6$ alkyl, $C_1$-$C_6$ alkenyl, $C_1$-$C_6$ alkynyl, aryl, heteroaryl, cyclyl, optionally substituted heterocyclyl or acyl, each of which can be optionally substituted;

$R^3$ is H, $C_1$-$C_6$ alkyl, $C_1$-$C_6$ alkenyl, $C_1$-$C_6$ alkynyl, aryl, heteroaryl, cyclyl, optionally substituted heterocyclyl, acyl or amino, each of which can be optionally substituted.

In some embodiments, $R^1$ is a nitrogen containing heteroaryl (e.g., including 1, 2, or 3 nitrogens (e.g., 1 or)). In some embodiments, $R^1$ is a bicyclic heteroaryl. In some embodiments, $R^1$ is a 6-6 fused heteroaryl. In some embodiments, $R^1$ is pyridyl, pyrimidyl, pyridazinyl, pyrazinyl, quinolinyl, naphthyridinyl (e.g., 1,5-naphthyridinyl), quinazolinyl, 5,6,7,8-tetrahydroquinazolinyl, 1,3-benzodioxlyl, 1,2,3-benzotriazolyl, benzoxazolyl, benzothiazolyl, 2,1,3-benzooxadiazole, imidazo[1,2-a]pyridinyl, pyrazolo[1,5-a]pyridinyl, [1,2,4]triazolo[1,5-a]pyridinyl, pyrazolo[1,5-a]pyrimidinyl, [1,2,4]triazolo[1,5-a]pyridinyl, [1,2,3]triazolo[1,5-a]pyrimidinyl, [1,2,4]triazolo[4,3-a]pyrimidinyl, [1,2,4]triazolo[4,3-a]pyridazinyl. In some embodiments, $R^1$ is

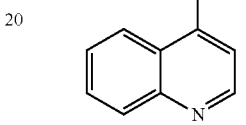

In some embodiments, $R^1$ is

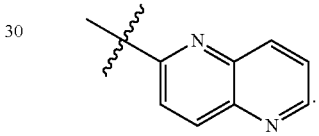

In some embodiments, $R^2$ is aryl, e.g., a substituted aryl. In some embodiments, $R^2$ is a nitrogen comprising heteroaryl (e.g., including 1, 2 or 3 nitrogens (e.g., 1 or 2)). In some embodiments, $R^2$ is an optionally substituted monocyclic heteroaryl (e.g., a six membered heteroaryl such as pyridyl, pyrimidyl, pyridazinyl or pyrazinyl). In some embodiments, $R^2$ is substituted. Exemplary substituents include halo, $C_1$-$C_6$ alkyl, halo$C_1$-$C_6$alkyl, $C_1$-$C_6$ alkoxy, OH, halo$C_1$-$C_6$alkoxy. In some embodiments, $R^2$ is monosubstituted. In some embodiments, $R^2$ is substituted with methyl. In one embodiment, $R^2$ is an optionally substituted pyridyl. In some embodiments, $R^2$ is

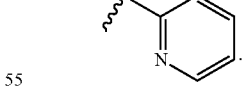

In some embodiments, $R^2$ is

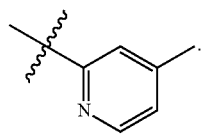 [SMILES: *c1cc(C)ccn1]

Exemplary compounds of formula (V) include:

4-(Pyridin-2-yl)-5-quinolin-4-yl-1,3-thiazol-2-amine;

4-(6-methylpyridin-2-yl)-5-(1,5-naphthyridin-2-yl)-1,3-thiazol-2-amine;

5-([1,5]Naphthyridin-2-yl)-4-pyridin-2-yl-1,3-thiazol-2-amine;

5-[2-(4-Chlorophenyl)pyridin-4-yl]-4-pyridin-2-yl-1,3-thiazol-2-amine;

5-[2-(4-Methoxyphenyl)pyridin-4-yl]-4-pyri-din-2-yl-1,3-thiazol-2-amine;

5-[2-(4-Fluorophenyl)pyridin-4-yl]-4-pyridin-2-yl-1,3-thiazol-2-amine;

5-[2-(4-Ethylphenyl)pyridin-4-yl]-4-pyridin-2-yl-1,3-thiazol-2-amine;

5-[2-(4-Ethoxyphenyl)pyridin-4-yl]-4-pyridin-2-yl-1,3-thiazol-2-amine; and

5-[2-(Thiophen-3-yl)pyridin-4-yl]-4-pyridin-2-yl-1,3-thiazol-2-amine.

In one aspect, the TGF-β inhibitor has the structure shown in formula (VI):

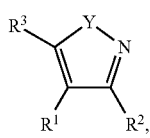

Formula (XI)

wherein:

$R^1$ is H, $C_1$-$C_6$ alkyl, $C_1$-$C_6$ alkenyl, $C_1$-$C_6$ alkynyl, aryl, heteroaryl, cyclyl, heterocyclyl, acyl, amino, or amide (e.g., —$CO_2NH_2$), each of which can be optionally substituted;

$R^2$ is $C_1$-$C_6$ alkyl, —O-alkyl, amino, acyl, aryl, heteroaryl, cyclyl or heterocyclyl, each of which can be optionally substituted;

$R^3$ is H, $C_1$-$C_6$ alkyl, —O-alkyl, amino, amide, —NHC(O)NH-alkyl, acyl, aryl, heteroaryl, cyclyl, heterocyclyl, each of which can be optionally substituted.

In some embodiments, $R^1$ is optionally substituted amide, e.g. —$CO_2NH_2$. In some embodiments, the amide is substituted with $C_1$-$C_6$ alkyl, which can also be optionally substituted, In some embodiments, $R^1$ is aryl, e.g., a substituted aryl. In some embodiments, $R^1$ is substituted with two substituents. In some embodiments, $R^1$ is substituted with two substituents, which together with the carbons to which they are attached form a ring. In some embodiments, $R^1$ is a substituted phenyl. In some embodiments, $R^1$ is a nitrogen containing heteroaryl (e.g., including 1, 2, or 3 nitrogens (e.g., 1 or)). In some embodiments, $R^1$ is a bicyclic heteroaryl. In some embodiments, $R^1$ is a 6-6 fused heteroaryl. In some embodiments, $R^1$ is pyridyl, pyrimidyl, pyridazinyl, pyrazinyl, quinolinyl, naphthyridinyl (e.g., 1,5-naphthyridinyl), quinazolinyl, 5,6,7,8-tetrahydroquinazolinyl, 1,3-benzodioxlyl, 1,2,3-benzotriazolyl, benzoxazolyl, benzothiazolyl, 2,1,3-benzooxadiazole, imidazo[1,2-a]pyridinyl, pyrazolo[1,5-a]pyridinyl, [1,2,4]triazolo[1,5-a]pyridinyl, pyrazolo[1,5-a]pyrimidinyl, [1,2,4]triazolo[1,5-a]pyrimidinyl, [1,2,3]triazolo[1,5-a]pyrimidinyl, [1,2,4]triazolo[4,3-a]pyrimidinyl, [1,2,4]triazolo[4,3-a]pyridazinyl. In some embodiments, $R^1$ is

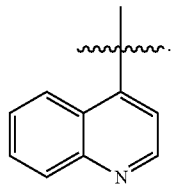 [SMILES: *c1ccnc2ccccc12]

In some embodiments, $R^1$ is

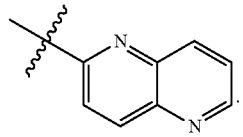

In some embodiments, $R^2$ is optionally substituted —O-alkyl. Exemplary substituents include aryl, heteroaryl, cyclyl and heterocyclyl, each of which can be optionally substituted. In some embodiments, $R^2$ is

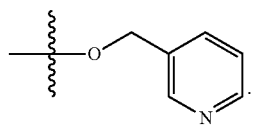 [SMILES: *OCc1cccnc1]

In some embodiments, $R^2$ is aryl, e.g., a substituted aryl. In some embodiments, $R^2$ is a nitrogen comprising heteroaryl (e.g., including 1, 2 or 3 nitrogens (e.g., 1 or 2)). In some embodiments, $R^2$ is an optionally substituted monocyclic heteroaryl (e.g., a six membered heteroaryl such as pyridyl, pyrimidyl, pyridazinyl or pyrazinyl). In some embodiments, $R^2$ is substituted. Exemplary substituents include halo, $C_1$-$C_6$ alkyl, halo$C_1$-$C_6$alkyl, $C_1$-$C_6$ alkoxy, OH, halo$C_1$-$C_6$alkoxy. In some embodiments, $R^2$ is monosubstituted. In some embodiments, $R^2$ is substituted with methyl. In one embodiment, $R^2$ is an optionally substituted pyridyl. In some embodiments, $R^2$ is

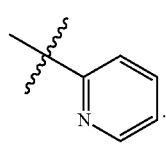 [SMILES: *c1ccccn1]

In some embodiments, $R^3$ is optionally substituted —NHC(O)NH-alkyl. In some embodiments, substituents is aryl or heteroaryl, each of which can be optionally substituted. In one embodiment, $R^3$

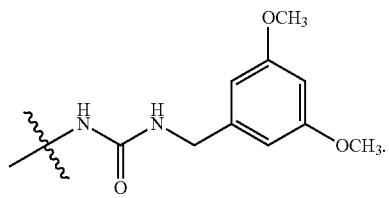 [SMILES: *NC(=O)NCc1cc(OC)cc(OC)c1]

Exemplary compounds of formula (VI) include:
1-(3,5-dimethoxybenzyl)-3-(4-carbamoyl-3-(2-(pyridin-3-yl)ethyl)isothiazol-5-yl)urea;
6-[3-(6-Methyl-pyridin-2-yl)-isoxazol-4-yl]-quinoxaline;
5-[3-(2-Cyclohex-1-enyl-ethyl)-ureido]-3-(pyridin-3-yl-methoxy)-isothiazole-4-carboxylic acid amide;
5-[3-(2,5-Dimethyl-benzyl)-ureido]-3-(pyridin-3-yl-methoxy)-isothiazole-4-carboxylic acid amide;
5-[3-(3,5-Dimethoxy-benzyl)-ureido]-3-(pyridin-3-yl-methoxy)-isothiazole-4-carboxylic acid amide;
5-[3-(2-Ethoxy-benzyl)-ureido]-3-(pyridin-3-ylmethoxy)-isothiazole-4-carboxylic acid amide;
5-{3-[2-(2-Ethoxy-phenyl)-ethyl]-ureido}-3-(pyridin-3-yl-methoxy)-isothiazole-4-carboxylic acid amide;
5-{3-[2-(3,4-Dimethoxy-phenyl)-ethyl]-ureido}-3-(pyridin-3-ylmethoxy)-isothiazole-4-carboxylic acid amide;
5-(3-Phenethyl-ureido)-3-(pyridin-3-yl-methoxy)-isothiazole-4-carboxylic acid amide;
5-{3-[2-(3-Ethoxy-4-methoxy-phenyl)-ethyl]-ureido}-3-(pyridin-3-ylmethoxy)-isothiazole-4-carboxylic acid amide;
5-{3-[2-(4-Ethoxy-phenyl)-ethyl]-ureido}-3-(pyridin-3-yl-methoxy)-isothiazole-4-carboxylic acid amide;
5-{3-[2-(4-Chloro-phenyl)-ethyl]-ureido}-3-(pyridin-3-yl-methoxy)-isothiazole-4-carboxylic acid amide;
5-{3-[2-(3-Chloro-phenyl)-ethyl]ureido}-3-(pyridin-3-yl-methoxy)-isothiazole-4-carboxylic acid amide;
5-{3-[2-(3-Methoxy-phenyl)-ethyl]ureido}-3-(pyridin-3-yl-methoxy)-isothiazole-4-carboxylic acid amide;
5-{3-[2-(4-Methoxy-phenyl)-ethyl]-ureido}-3-(pyridin-3-ylmethoxy)-isothiazole-4-carboxylic acid amide;
5-{3-[2-(3-Bromo-4-methoxy-phenyl)-ethyl]-ureido}-3-(pyridin-3-ylmethoxy)-isothiazole-4-carboxylic acid amide;
5-{3-[2-(4-Bromo-phenyl)-ethyl]-ureido}-3-(pyridin-3-yl-methoxy)-isothiazole-4-carboxylic acid amide;
5-{3-[2-(2-Chloro-phenyl)-ethyl]ureido}-3-(pyridin-3-yl-methoxy)-isothiazole-4-carboxylic acid amide;
5-{3-[2-(3-Chloro-phenyl)-ethyl]ureido}-3-(pyridin-3-yl-methoxy)-isothiazole-4-carboxylic acid amide;
5-{3-[2-(2-Fluoro-phenyl)-ethyl]-ureido}-3-(pyridin-3-yl-methoxy)-isothiazole-4-carboxylic acid amide;
5-{3-[2-(3-Fluoro-phenyl)-ethyl]ureido}-3-(pyridin-3-yl-methoxy)-isothiazole-4-carboxylic acid amide;
5-{3-[2-(4-Fluoro-phenyl)-ethyl]ureido}-3-(pyridin-3-yl-methoxy)-isothiazole-4-carboxylic acid amide;
5-{3-[2-(4-Ethoxy-3-methoxy-phenyl)-ethyl]ureido}-3-(pyridin-3-ylmethoxy)-isothiazole-4-carboxylic acid amide;
5-{3-[2-(3-Ethoxy-4-methoxy-phenyl)-ethyl]-ureido}-3-(pyridin-3-ylmethoxy)-isothiazole-4-carboxylic acid amide;
5-{3-[2-(2,5-Dimethoxy-phenyl)-ethyl]ureido}-3-(pyridin-3-ylmethoxy)-isothiazole-4-carboxylic acid amide;
5-{3-[2-(3-Methoxy-phenyl)-ethyl]ureido}-3-(pyridin-3-yl-methoxy)-isothiazole-4-carboxylic acid amide;
5-[3-(2-Dinuoromethoxy-benzyl)-ureido]-3-(pyridin-3-yl-methoxy)-isothiazole-4-carboxylic acid amide;
5-[3-(2,6-Dimethoxy-benzyl)-ureido]-3-(pyridin-3-yl-methoxy)-isothiazole-4-carboxylic acid amide;
5-[3-(2,5-Dichloro-benzyl)-ureido]-3-(pyridin-3-yl-methoxy)-isothiazole-4-carboxylic acid amide;
5-[3-(3-Morpholin-4-yl-propyl)-ureido]-3-(pyridin-3-yl-methoxy)-isothiazole-4-carboxylic acid amide;
5-[3-(2-Morpholin-4-yl-ethyl)-ureido]-3-(pyridin-3-yl-methoxy)-isothiazole-4-carboxylic acid amide;
5-[3-(2-Diethylamino-ethyl)-ureido]-3-(pyridin-3-yl-methoxy)-isothiazole-4-carboxylic acid amide;
5-[3-(3-Dimethylamino-propyl)-ureido]-3-(pyridin-3-yl-methoxy)-isothiazole-4-carboxylic acid amide;
5-{3-[2-(1-Methyl-pyrrolidin-2-yl)-ethyl]-ureido}-3-(pyridin-3-ylmethoxy)-isothiazole-4-carboxylic acid amide;
5-{3-[3-(2-Methyl-piperidin-1-yl)-propyl]-ureido}-3-(pyridin-3-ylmethoxy)-isothiazole-4-carboxylic acid amide;
(R),(R)-5-[3-(2-Hydroxy-cycloheptylmethyl)-ureido]-3-(pyridin-3-ylmethoxy)-isothiazole-4-carboxylic acid amide;
(R),(R)-5-[3-(2-Hydroxy-cyclooctylmethyl)-ureido]-3-(pyridin-3-ylmethoxy)-isothiazole-4-carboxylic acid amide;
5-[3-(2-Hydroxy-ethyl)-ureido]-3-(pyridin-3-ylmethoxy)-isothiazole-4-carboxylic acid amide;
5-[3-(2-Hydroxy-butyl)-ureido]-3-(pyridin-3-ylmethoxy)-isothiazole-4-carboxylic acid amide;
5-{3-[3-(2-Oxo-pyrrolidin-1-yl)-propyl]ureido}-3-(pyridin-3-ylmethoxy)-isothiazole-4-carboxylic acid amide;
5-[3-(3-Imidazol-1-yl-propyl)-ureido]-3-(pyridin-3-yl-methoxy)-isothiazole-4-carboxylic acid amide;
5-(3-Benzyl-ureido)-3-(pyridin-3-yl-methoxy)-isothiazole-4-carboxylic acid amide;
5-[3-(2,5-Difluoro-benzyl)-ureido]-3-(pyridin-3-yl-methoxy)-isothiazole-4-carboxylic acid amide;
3-(1-Pyridin-3-yl-ethoxy)-5-(3-pyridin-2-yl-methyl-ureido)-isothiazole-4-carboxylic acid amide;
5-[3-(2,6-Dimethoxy-benzyl)-ureido]-3-(1-pyridin-3-yl-ethoxy)-isothiazole-4-carboxylic acid amide;
5-(3-Cyclopropylmethyl-ureido)-3-(pyridin-3-ylmethoxy)-isothiazole-4-carboxylic acid amide;
5-(3-Methyl-ureido)-3-(pyridin-3-yl-methoxy)-isothiazole-4-carboxylic acid amide;
5-(3-Methyl-ureido)-3-(1-pyridin-3-yl-ethoxy)-isothiazole-4-carboxylic acid amide; and
5-[3-(3,5-Dichloro-benzyl)-ureido]-3-(pyri-din-3-yl-methoxy)-isothiazole-4-carboxylic acid amide.

Antibodies

Antibodies that can be used according to the methods described herein include complete immunoglobulins, antigen binding fragments of immunoglobulins, as well as antigen binding proteins that comprise antigen binding domains of immunoglobulins. Antigen binding fragments of immunoglobulins include, for example, Fab, Fab', F(ab')2, scFv and dAbs. Modified antibody formats have been developed which retain binding specificity, but have other characteristics that may be desirable, including for example, bispecificity, multivalence (more than two binding sites), and compact size (e.g., binding domains alone).

Single chain antibodies lack some or all of the constant domains of the whole antibodies from which they are derived. Therefore, they can overcome some of the problems associated with the use of whole antibodies. For example, single-chain antibodies tend to be free of certain undesired interactions between heavy-chain constant regions and other biological molecules. Additionally, single-chain antibodies are considerably smaller than whole antibodies and can have greater permeability than whole antibodies, allowing single-chain antibodies to localize and bind to target antigen-binding sites more efficiently. Furthermore, the relatively small size of single-chain antibodies makes them less likely to provoke an unwanted immune response in a recipient than whole antibodies.

Multiple single chain antibodies, each single chain having one VH and one VL domain covalently linked by a first peptide linker, can be covalently linked by at least one or more peptide linkers to form multivalent single chain antibodies, which can be monospecific or multispecific. Each chain of a multivalent single chain antibody includes a variable light chain fragment and a variable heavy chain fragment, and is linked by a peptide linker to at least one other chain. The peptide linker is composed of at least fifteen amino acid residues. The maximum number of linker amino acid residues is approximately one hundred.

Two single chain antibodies can be combined to form a diabody, also known as a bivalent dimer. Diabodies have two chains and two binding sites, and can be monospecific or bispecific. Each chain of the diabody includes a VH domain connected to a VL domain. The domains are connected with linkers that are short enough to prevent pairing between domains on the same chain, thus driving the pairing between complementary domains on different chains to recreate the two antigen-binding sites.

Three single chain antibodies can be combined to form triabodies, also known as trivalent trimers. Triabodies are constructed with the amino acid terminus of a VL or VH domain directly fused to the carboxyl terminus of a VL or VH domain, i.e., without any linker sequence. The triabody has three Fv heads with the polypeptides arranged in a cyclic, head-to-tail fashion. A possible conformation of the triabody is planar with the three binding sites located in a plane at an angle of 120 degrees from one another. Triabodies can be monospecific, bispecific or trispecific.

Thus, antibodies useful in the methods described herein include, but are not limited to, naturally occurring antibodies, bivalent fragments such as (Fab')2, monovalent fragments such as Fab, single chain antibodies, single chain Fv (scFv), single domain antibodies, multivalent single chain antibodies, diabodies, triabodies, and the like that bind specifically with an antigen (e.g., a TGFβR epitope).

Antibodies for use in the methods described herein can be obtained from commercial sources such as AbCam (Cambridge, Mass.), New England Biolabs (Ipswich, Mass.), Santa Cruz Biotechnologies (Santa Cruz, Calif.), Biovision (Mountain View, Calif.), R&D Systems (Minneapolis, Minn.), and Cell Signaling (Danvers, Mass.), among others. Antibodies can also be raised against a polypeptide or portion of a polypeptide by methods known to those skilled in the art. Antibodies are readily raised in animals such as rabbits or mice by immunization with the gene product, or a fragment thereof. Immunized mice are particularly useful for providing sources of B cells for the manufacture of hybridomas, which in turn are cultured to produce large quantities of monoclonal antibodies. Antibody manufacture methods are described in detail, for example, in Harlow et al., Eds., *Antibodies: A Laboratory Manual*, Cold Spring Harbor Laboratory, New York (1988), which is hereby incorporated by reference in its entirety.

While both polyclonal and monoclonal antibodies can be used in the methods described herein, it is preferred that a monoclonal antibody is used where conditions require increased specificity for a particular protein.

RNA Interference

"RNA interference (RNAi)" is an evolutionarily conserved process whereby the expression or introduction of RNA of a sequence that is identical or highly similar to a target gene results in the sequence specific degradation or specific post-transcriptional gene silencing (PTGS) of messenger RNA (mRNA) transcribed from that targeted gene (see Coburn, G. and Cullen, B., J. of Virology 76(18):9225 (2002)), thereby inhibiting expression of the target gene. In one embodiment, the RNA is double stranded RNA (dsRNA). This process has been described in plants, invertebrates, and mammalian cells. In nature, RNAi is initiated by the dsRNA-specific endonuclease Dicer, which promotes processive cleavage of long dsRNA into double-stranded fragments termed siRNAs. siR-NAs are incorporated into a protein complex (termed "RNA induced silencing complex," or "RISC") that recognizes and cleaves target mRNAs. RNAi can also be initiated by introducing nucleic acid molecules, e.g., synthetic siRNAs or RNA interfering agents, to inhibit or silence the expression of target genes. As used herein, "inhibition of target gene expression" includes any decrease in expression or protein activity or level of the target gene or protein encoded by the target gene as compared to a situation wherein no RNA interference has been induced. The decrease may be of at least 20%, 30%, 40%, 50%, 60%, 70%, 80%, 90%, 95% or 99% or more as compared to the expression of a target gene or the activity or level of the protein encoded by a target gene which has not been targeted by an RNA interfering agent.

"Short interfering RNA" (siRNA), also referred to herein as "small interfering RNA" is defined as a nucleic acid-comprising agent which functions to inhibit expression of a target gene, by RNAi. An siRNA may be chemically synthesized, may be produced by in vitro transcription, or may be produced within a host cell. In one embodiment, siRNA is a double stranded RNA (dsRNA) molecule of about 15 to about 40 nucleotides in length, preferably about 15 to about 28 nucleotides, more preferably about 19 to about 25 nucleotides in length, and more preferably about 19, 20, 21, 22, or 23 nucleotides in length, and may contain a 3' and/or 5' overhang on each strand having a length of about 0, 1, 2, 3, 4, or 5 nucleotides. The length of the overhang is independent between the two strands, i.e., the length of the overhang on one strand is not dependent on the length of the overhang on the second strand. Preferably the siRNA is capable of promoting RNA interference through degradation or specific post-transcriptional gene silencing (PTGS) of the target messenger RNA (mRNA).

siRNAs also include small hairpin (also called stem loop) RNAs (shRNAs). In one embodiment, these shRNAs are composed of a short (e.g., about 19 to about 25 nucleotide) antisense strand, followed by a nucleotide loop of about 5 to about 9 nucleotides, and the analogous sense strand. Alternatively, the sense strand may precede the nucleotide loop structure and the antisense strand may follow. These shRNAs may be encoded by plasmids, retroviruses, and lentiviruses and expressed from, for example, the pol III U6 promoter, or another promoter (see, e.g., Stewart, et al., RNA April; 9(4): 493-501 (2003), incorporated by reference herein in its entirety).

The target gene or sequence of the RNA interfering agent may be a cellular gene or genomic sequence, e.g. the TGFβR sequence. An siRNA may be substantially homologous to the target gene or genomic sequence, or a fragment thereof. As used in this context, the term "homologous" is defined as being substantially identical, sufficiently complementary, or similar to the target mRNA, or a fragment thereof, to effect RNA interference of the target. In addition to native RNA molecules, RNA suitable for inhibiting or interfering with the expression of a target sequence include RNA derivatives and analogs. Preferably, the siRNA is identical in sequence to its target.

The siRNA preferably targets only one sequence. Each of the RNA interfering agents, such as siRNAs, can be screened for potential off-target effects by, for example, expression profiling. Such methods are known to one skilled in the art and are described, for example, in Jackson et al., Nature Biotechnology 6:635-637 (2003). In addition to expression profiling, one may also screen the potential target sequences for similar sequences in the sequence databases to identify potential sequences which may have off-target effects. For example, according to Jackson et al. (Id.) 15, or perhaps as few as 11 contiguous nucleotides, of sequence identity are sufficient to direct silencing of non-targeted transcripts. Therefore, one may initially screen the proposed siRNAs to avoid potential off-target silencing using sequence identity analysis by any known sequence comparison methods, such as BLAST.

siRNA molecules need not be limited to those molecules containing only RNA, but, for example, further encompasses chemically modified nucleotides and non-nucleotides that effect RNA interference, and also include molecules wherein a ribose sugar molecule is substituted for another sugar molecule or a molecule which performs a similar function. Moreover, a non-natural linkage between nucleotide residues can be used, such as a phosphorothioate linkage. The RNA strand can be derivatized with a reactive functional group or a reporter group, such as a fluorophore. Particularly useful derivatives are modified at a terminus or termini of an RNA strand, typically the 3' terminus of the sense strand. For example, the 2'-hydroxyl at the 3' terminus can be readily and selectively derivatized with a variety of groups.

Other useful RNA derivatives incorporate nucleotides having modified carbohydrate moieties, such as 2'O-alkylated residues or 2'-O-methyl ribosyl derivatives and 2'-O-fluoro ribosyl derivatives. The RNA bases may also be modified. Any modified base useful for inhibiting or interfering with the expression of a target sequence may be used. For example, halogenated bases, such as 5-bromouracil and 5-iodouracil can be incorporated. The bases may also be alkylated, for example, 7-methylguanosine can be incorporated in place of a guanosine residue. Non-natural bases that yield successful inhibition can also be incorporated.

The most preferred siRNA modifications include 2'-deoxy-2'-fluorouridine or locked nucleic acid (LNA) nucleotides and RNA duplexes containing either phosphodiester or varying numbers of phosphorothioate linkages. Such modifications are known to one skilled in the art and are described, for example, in Braasch et al., Biochemistry 42: 7967-7975 (2003). Most of the useful modifications to the siRNA molecules can be introduced using chemistries established for antisense oligonucleotide technology. Preferably, the modifications involve minimal 2'-O-methyl modification, preferably excluding such modification. Modifications also preferably exclude modifications of the free 5'-hydroxyl groups of the siRNA.

siRNAs useful for targeting TGFβR or ALK5 expression can be readily designed and tested. Chalk et al. (Nucl. Acids Res. 33: D131-D134 (2005)) describe a database of siRNA sequences and a predictor of siRNA sequences. Linked to the sequences in the database is information such as siRNA thermodynamic properties and the potential for sequence-specific off-target effects. The database and associated predictive tools enable the user to evaluate an siRNA's potential for inhibition and non-specific effects. The database is available at on the world wide web at siRNA.cgb.ki.se.

Synthetic siRNA molecules, including shRNA molecules, can be obtained using a number of techniques known to those of skill in the art. For example, the siRNA molecule can be chemically synthesized or recombinantly produced using methods known in the art, such as using appropriately protected ribonucleoside phosphoramidites and a conventional DNA/RNA synthesizer (see, e.g., Elbashir, S. M. et al., Nature 411:494-498 (2001); Elbashir, S. M., et al., Genes & Development 15:188-200 (2001); Harborth, J. et al., J. Cell Science 114:4557-4565 (2001); Masters, J. R. et al., Proc. Natl. Acad. Sci., USA 98:8012-8017 (2001); and Tuschl, T. et al., Genes & Development 13:3191-3197 (1999)). Alternatively, several commercial RNA synthesis suppliers are available including, but not limited to, Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA), and Cruachem (Glasgow, UK). As such, siRNA molecules are not overly difficult to synthesize and are readily provided in a quality suitable for RNAi. In addition, dsRNAs can be expressed as stem loop structures encoded by plasmid vectors, retroviruses and lentiviruses (Paddison, P. J. et al., Genes Dev. 16:948-958 (2002); McManus, M. T. et al., RNA 8:842-850 (2002); Paul, C. P. et al., Nat. Biotechnol. 20:505-508 (2002); Miyagishi, M. et al., Nat. Biotechnol. 20:497-500 (2002); Sui, G. et al., Proc. Natl. Acad. Sci., USA 99:5515-5520 (2002); Brummelkamp, T. et al., Cancer Cell 2:243 (2002); Lee, N. S., et al., Nat. Biotechnol. 20:500-505 (2002); Yu, J. Y., et al., Proc. Natl. Acad. Sci., USA 99:6047-6052 (2002); Zeng, Y., et al., Mol. Cell. 9:1327-1333 (2002); Rubinson, D. A., et al., Nat. Genet. 33:401-406 (2003); Stewart, S. A., et al., RNA 9:493-501 (2003)).

In the methods described herein, the RNA interference molecule is contacted with somatic cells in culture, thus eliminating delivery problems inherent with administering e.g., siRNA in vivo to a patient in need thereof.

Confirming Pluripotency and Cell Reprogramming

To confirm the induction of pluripotent stem cells, isolated clones can be tested for the expression of a stem cell marker. Such expression identifies the cells as induced pluripotent stem cells. Stem cell markers can be selected from the non-limiting group including SSEA1, CD9, Nanog, Fbx15, Ecat1, Esg1, Eras, Gdf3, Fgf4, Cripto, Dax1, Zpf296, Slc2a3, Rex1, Utf1, and Nat1. Methods for detecting the expression of such markers can include, for example, RT-PCR and immunological methods that detect the presence of the encoded polypeptides.

The pluripotent stem cell character of the isolated cells can be confirmed by any of a number of tests evaluating the expression of ES markers and the ability to differentiate to cells of each of the three germ layers. As one example, teratoma formation in nude mice can be used to evaluate the pluripotent character of the isolated clones. The cells are introduced to nude mice and histology is performed on a tumor arising from the cells. The growth of a tumor comprising cells from all three germ layers further indicates that the cells are pluripotent stem cells.

As used in this specification and the appended claims, the singular forms "a," "an," and "the" include plural references unless the context clearly dictates otherwise. Thus for example, references to "the method" includes one or more methods, and/or steps of the type described herein and/or which will become apparent to those persons skilled in the art upon reading this disclosure and so forth.

It is understood that the foregoing detailed description and the following examples are illustrative only and are not to be taken as limitations upon the scope of the invention. Various changes and modifications to the disclosed embodiments, which will be apparent to those of skill in the art, may be made without departing from the spirit and scope of the present invention. Further, all patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and do not constitute any admission as to the correctness of the dates or contents of these documents.

The present invention may be as defined in any one of the following numbered paragraphs.

1. A method for producing an induced pluripotent stem cell from a somatic cell, the method comprising:
   (a) treating a somatic cell to re-program it or its progeny to a pluripotent stem cell phenotype;
   (b) contacting the somatic cell or its progeny with an inhibitor of the TGF-β signaling pathway; and
   (c) isolating a pluripotent stem cell from cells of step (b).
2. The method of paragraph 1, wherein the treating comprises introducing a nucleic acid sequence encoding one or more transcription factors selected from the group consisting of Oct4, Sox2, c-MYC and Klf4 to a somatic cell.
3. The method of paragraph 1, wherein the inhibitor of the TGF-β signaling pathway comprises an inhibitor of TGF-β receptor activity.
4. The method of paragraph 3, wherein the inhibitor of TGF-β receptor activity comprises an inhibitor of ALK4, ALK5, or ALK7.
5. The method of paragraph 3, wherein the inhibitor of TGF-β receptor activity is selected from the group consisting of an antibody, a small molecule, and an RNA interference molecule.
6. The method of paragraph 5, wherein the small molecule is selected from the group consisting of 2-(3-(6-Methylpyridin-2-yl)-1H-pyrazol-4-yl)-1,5 napththyridine, [3-(Pyridin-2-yl)-4-(4-quinoyl)]-1H-pyrazole, and 3-(6-Methylpyridin-2-yl)-4-(4-quinolyl)-1-phenylthiocarbamoyl-1H-pyrazole.
7. The method of paragraph 2, wherein the nucleic acid sequences are comprised in a viral vector or a plasmid.
8. The method of paragraph 1, wherein production of the induced pluripotent stem cell is determined by detection of a stem cell marker.
9. The method of paragraph 8, wherein the stem cell marker is selected from the group consisting of SSEA1, CD9, Nanog, Fbx15 Ecat1, Esg1, Eras, Gdf3, Fgf4, Cripto, Dax1, Zpf296, Slc2a3, Rex1, Utf1, and Nat1.
10. A method for increasing the efficiency of induced pluripotent stem cell production, the method comprising:
    (a) treating a somatic cell to re-program it or its progeny to a pluripotent stem cell phenotype; and
    (b) contacting the somatic cells subjected to the process of step (a) with an inhibitor of the TGF-β signaling pathway,
    wherein the efficiency of induced pluripotent stem cell generation is increased relative to such generation occurring without the contacting.
11. The method of paragraph 10, wherein the treating comprises introducing a nucleic acid sequence encoding one or more transcription factors selected from the group consisting of Oct4, Sox2, c-MYC and Klf4 to a somatic cell.
12. The method of paragraph 10, wherein the inhibitor of the TGF-β signaling pathway comprises an inhibitor of TGF-β receptor activity.
13. The method of paragraph 12, wherein the inhibitor of TGF-β receptor activity comprises an inhibitor of ALK4, ALK5, or ALK7.
14. The method of paragraph 12, wherein the inhibitor of TGF-β receptor activity is selected from the group consisting of an antibody, a small molecule, and an RNA interference molecule.
15. The method of paragraph 14, wherein the small molecule is selected from the group consisting of 2-(3-(6-Methylpyridin-2-yl)-1H-pyrazol-4-yl)-1,5 napththyridine, [3-(Pyridin-2-yl)-4-(4-quinoyl)]-1H-pyrazole, and 3-(6-Methylpyridin-2-yl)-4-(4-quinolyl)-1-phenylthiocarbamoyl-1H-pyrazole.
16. The method of paragraph 11, wherein the nucleic acid sequences are comprised in a viral vector or a plasmid.
17. The method of paragraph 10, wherein production of the induced pluripotent stem cell is confirmed by detection of a stem cell marker.
18. The method of paragraph 17, wherein the stem cell marker is selected from the group consisting of SSEA1, CD9, Nanog, Fbx15, Ecat1, Esg1, Eras, Gdf3, Fgf4, Cripto, Dax1, Zpf296, Slc2a3, Rex1, Utf1, and Nat1.
19. A method for increasing the rate of induced pluripotent stem cell production, the method comprising:
    (a) treating a somatic cell to re-program it or its progeny to a pluripotent stem cell phenotype; and
    (b) contacting the somatic cell with an inhibitor of the TGF-β signaling pathway, wherein the rate of induced pluripotent stem cell generation is increased relative to the rate of the generation occurring without the contacting.
20. The method of paragraph 19, wherein the treating comprises introducing a nucleic acid sequence encoding one or more transcription factors selected from the group consisting of Oct4, Sox2, c-MYC and Klf4 to a somatic cell.
21. The method of paragraph 19, wherein the inhibitor of the TGF-β signaling pathway comprises an inhibitor of TGF-β receptor activity.
22. The method of paragraph 21, wherein the inhibitor of TGF-β receptor activity comprises an inhibitor of ALK4, ALK5, or ALK7.
23. The method of paragraph 21, wherein the inhibitor of TGF-β receptor activity is selected from the group consisting of an antibody, a small molecule, and an RNA interference molecule.
24. The method of paragraph 23, wherein the small molecule is selected from the group consisting of 2-(3-(6-Methylpyridin-2-yl)-1H-pyrazol-4-yl)-1,5 napththyridine, [3-(Pyridin-2-yl)-4-(4-quinoyl)]-1H-pyrazole, and 3-(6-Methylpyridin-2-yl)-4-(4-quinolyl)-1-phenylthiocarbamoyl-1H-pyrazole.
25. The method of paragraph 20, wherein the nucleic acid sequences are comprised in a viral vector or a plasmid.
26. The method of paragraph 19, wherein production of the induced pluripotent stem cell is confirmed by detection of a stem cell marker.
27. The method of paragraph 26, wherein the stem cell marker is selected from the group consisting of SSEA1, CD9, Nanog, Fbx15, Ecat1, Esg1, Eras, Gdf3, Fgf4, Cripto, Daxa1, Zpf296, Slc2a3, Rex1, Utf1, and Nat1.
28. An induced pluripotent stem cell composition comprising an induced pluripotent stem cell in an admixture with an inhibitor of the TGF-β signaling pathway.
29. The composition of paragraph 28, wherein the inhibitor of the TGF-β signaling pathway comprises an inhibitor of TGF-β receptor activity.
30. The composition of paragraph 29, wherein the inhibitor of TGF-β receptor activity comprises an inhibitor of ALK4, ALK5, or ALK7.
31. The composition of paragraph 29, wherein the inhibitor of TGF-β receptor activity is selected from the group consisting of an antibody, a small molecule, and an RNA interference molecule.

32. The composition of paragraph 31, wherein the small molecule is selected from the group consisting of 2-(3-(6-Methylpyridin-2-yl)-1H-pyrazol-4-yl)-1,5 napththyridine, [3-(Pyridin-2-yl)-4-(4-quinoyl)]-1H-pyrazole, and 3-(6-Methylpyridin-2-yl)-4-(4-quinolyl)-1-phenylthiocarbamoyl-1H-pyrazole.

33. The composition of paragraph 29, wherein the induced pluripotent stem cell expresses a stem cell marker.

34. The composition of paragraph 33, wherein the stem cell marker is selected from the group consisting of SSEA1, CD9, Nanog, Fbx15, Ecat1, Esg1, Eras, Gdf3, Fgf4, Cripto, Dax1, Zpf296, Slc2a3, Rex1, Utf1, and Nat1.

35. A kit for producing induced pluripotent stem cells, the kit comprising:
    (a) nucleic acid sequences encoding one or more transcription factors selected from the group consisting of Oct4, Sox2, c-MYC and Klf4,
    (b) an inhibitor of the TGF-β receptor signaling pathway,
    (c) packaging materials therefor.

36. The kit of paragraph 35, wherein the inhibitor of the TGF-β signaling pathway comprises an inhibitor of TGF-β receptor activity.

37. The kit of paragraph 35, wherein the inhibitor of TGF-β receptor activity comprises an inhibitor of ALK4, ALK5, or ALK7.

38. The kit of paragraph 35, wherein the inhibitor of TGF-β receptor activity is selected from the group consisting of an antibody, a small molecule, and an RNA interference molecule.

39. The kit of paragraph 38, wherein the small molecule is selected from the group consisting of 2-(3-(6-Methylpyridin-2-yl)-1H-pyrazol-4-yl)-1,5 napththyridine, [3-(Pyridin-2-yl)-4-(4-quinoyl)]-1H-pyrazole, and 3-(6-Methylpyridin-2-yl)-4-(4-quinolyl)-1-phenylthiocarbamoyl-1H-pyrazole.

40. The kit of paragraph 35, wherein the nucleic acid sequences are comprised in a viral vector or a plasmid.

41. The kit of paragraph 35, comprising each of the transcription factors selected from the group consisting of Oct4, Sox2, c-MYC and Klf4.

42. A cell composition prepared by the method of any one of paragraphs 1-27.

EXAMPLES

The following Examples indicate that inhibition of the TGF-β signaling pathway acts as a cooperative factor in the reprogramming of murine fibroblasts, enabling more efficient and faster induction of iPSCs in a dose-dependent manner, while activation of TGF-β signaling blocks reprogramming. In addition to a strong cooperative effect, use of a TGF-β receptor inhibitor bypasses the requirement of exogenous cMyc or Sox2, highlighting its dual role as both a cooperative and a replacement factor. The identification of a highly characterized pathway that operates in reprogramming will open up new avenues for mechanistic dissection of the reprogramming process, as well as facilitate the derivation of iPSCs using small molecules.

The TGFβ signaling pathway is identified as a cooperative pathway in reprogramming during functional validation of a constructed network that linked retroviral insertion sites across several mouse iPSC lines (Varas, F., et al., (2008) Stem Cells). Although the biological validation of network targets was largely negative, in agreement with statistical analyses indicating that the network did not differ from randomly constructed networks, it was found that use of a TGF-β receptor I kinase/activin-like kinase 5 (Alk5) inhibitor enhances the efficiency of iPSC derivation.

Example 1

Figure 1B:
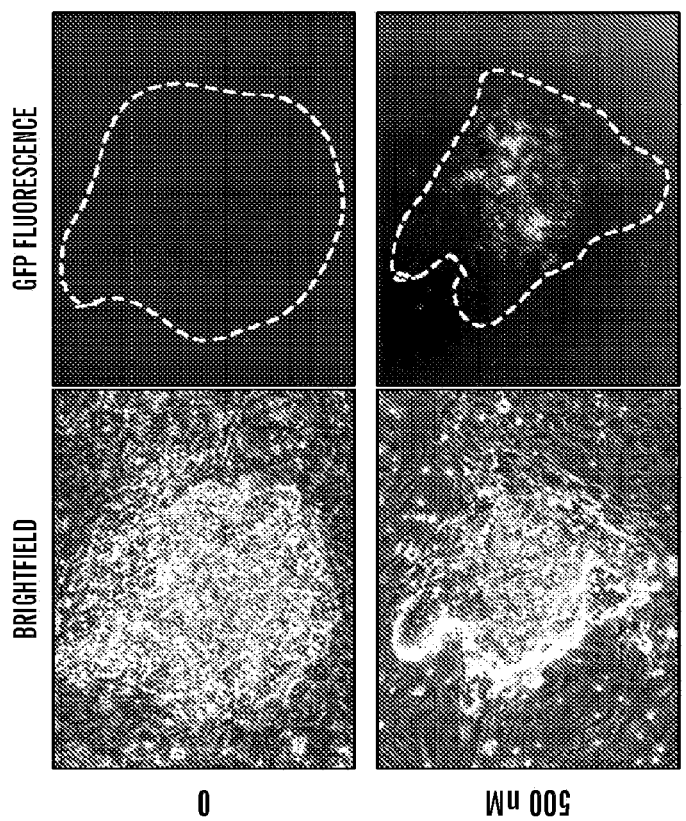
FIG. 1:
1A. Effect of Alk5 inhibitor treatment on the number of Sox2-GFP+iPS colonies
1B. Example of untreated (top image) and Alk5 inhibitor-treated emerging iPS colonies. Note lack of GFP expression in the untreated colony.
Figure 1A:
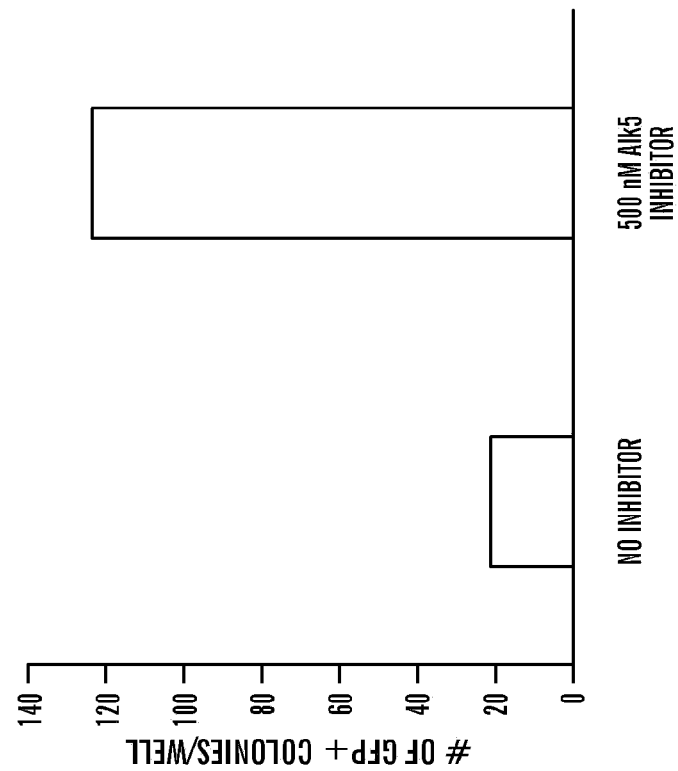

Fibroblasts cultures were established from mice expressing green-fluorescent protein (GFP) from the genomic locus of the pluripotency gene Sox2. Sox2-GFP fibroblasts were then infected with viruses expressing the reprogramming factors c-Myc, Klf4, Oct4 and Sox2 in the presence and absence of a chemical inhibitor highly specific for the TGF-beta receptor Alk5 (ALK5 inhibitor II). GFP+colonies with embryonic stem (ES) cell morphology were scored 20 days after infection. In the presence of Alk5 inhibitor II, 5-10 fold more GFP+colonies were observed, which after picking could be expanded like ES cells (see FIG. 1A). In addition, those colonies that formed in the presence of the Alk5 inhibitor started expressing GFP earlier than those that formed in the absence of the chemical, indicating that inhibiting Alk5 accelerates the activation of endogenous pluripotency genes (see FIG. 1B). These observations indicate that using chemicals to interfere with TGF-beta signaling is a way to increase both the kinetics and the efficiency of reprogramming.

Example 2

Figure 2B:
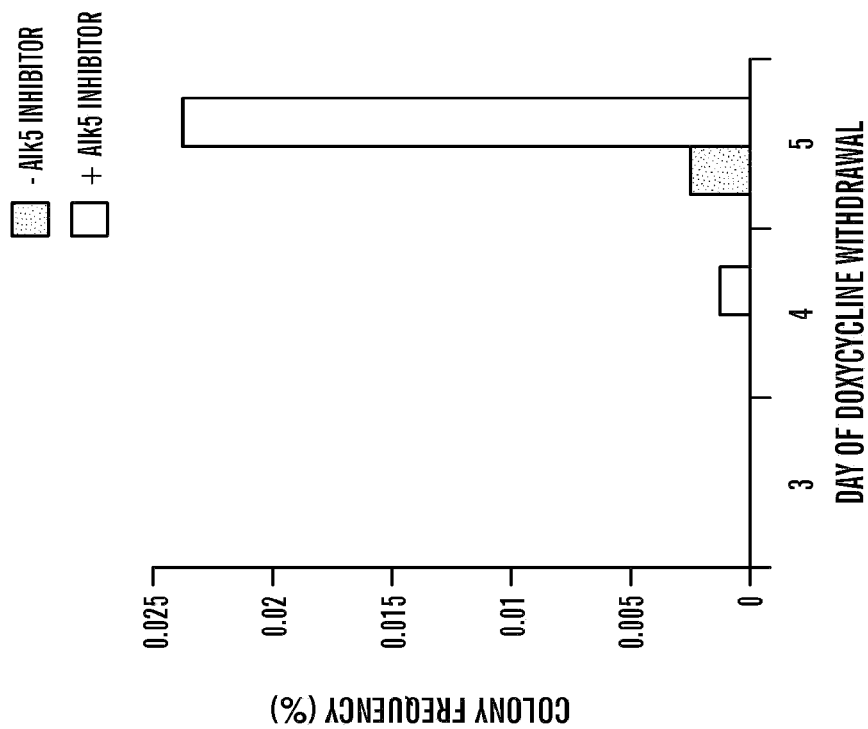
FIG. 2. An Alk5 Inhibitor Acts Cooperatively to Promote iPSC Induction
2A. Alkaline phosphatase stain for primary iPSC colonies, treated with or without the Alk5 inhibitor (1 µM) during dox induction. MEFs were infected with four factors and colonies were stained on day 12 (8d+dox/4d−dox).
2B. Kinetics of reprogramming in MEFs infected with four factors. Dox was applied for either 3, 4, or 5 days, with or without the Alk5 inhibitor (2 µM). Colonies were counted on day 16 based on morphology; all picked clones were capable of generating dox-independent lines.
2C. Pluripotency of iPSCs derived after four days of dox induction using the Alk5 inhibitor. (i-iii) Immunostaining for pluripotency markers, (i) Nanog, (ii) Oct4, and (iii) Sox2. Colonies were stained after three passages without dox, thus reflecting endogenous expression. (iv-vi) Teratoma formation, demonstrating differentiation into lineages from all three germ layers: (iv) neural tissue, (v) cartilage, (vi) gut-like epithelium.
2D. Dose-response curve for the Alk5 inhibitor in MEFs induced with four factors. Dox and the inhibitor were applied for 8 days; colonies were quantified on day 12 based on Oct4 immunostaining.
2E Effect of TGF-β ligands in reprogramming, using four-factor infected MEFs (dox for 12d; counts on day 16 based on Oct4 immunostaining). TGF-β concentrations: low, 1 ng/mL; medium, 2.5 ng/mL; high, 5 ng/mL.
2F. Timing of Alk5 inhibitor action. The Alk5 inhibitor (1 µM) was applied in 4-day time intervals. Control=no inhibitor, Full-time=inhibitor added days 1-16. Dox was withdrawn on day 12, and colonies were quantified on day 16 based on Oct4 immunostaining.
2G. Priming effect of the Alk5 inhibitor. Inhibitor (1 µM) was applied for either 3 days before (−3 to 0d) or during the first 3 days of dox induction (0 to +3d), or both (−3d to +3d). Control=no inhibitor. Dox was withdrawn on day 8 and colonies were quantified on day 12 by Oct4 immunostaining.
Figure 2A:
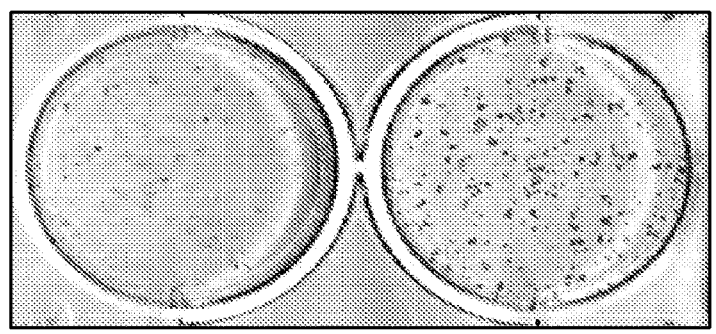
Figure 2C:
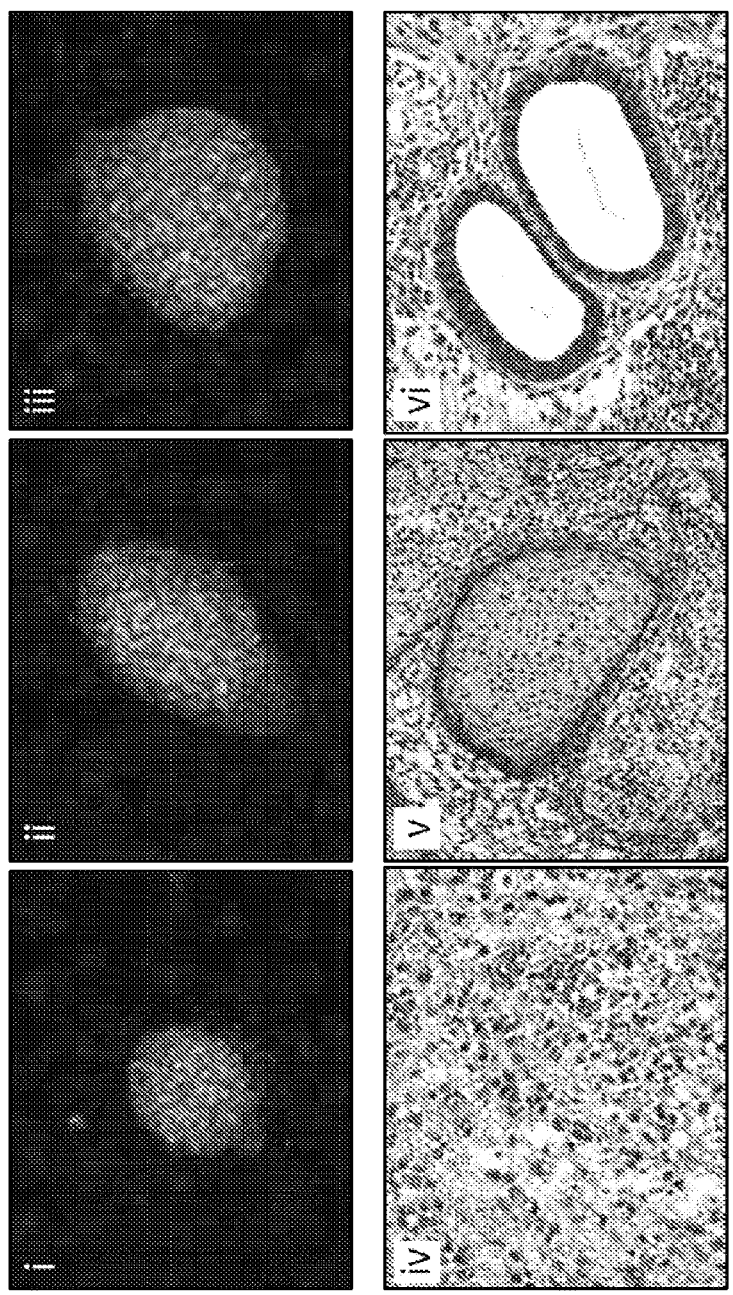

To induce reprogramming, MEFs were infected with a reverse tetracycline transactivator (rtTA) transgene with doxycycline-inducible lentiviruses encoding the four reprogramming factors as previously described (Stadtfeld, M., et al., (2008) Cell Stem Cell 2, 230-240). Administration of the Alk5 inhibitor during the course of doxycycline (dox) induction elicited a striking increase in the number of iPSC colonies (FIG. 2A). These iPSC clones could be expanded in the absence of dox, which is a strong indicator of successful reprogramming (Stadtfeld, M., et al., (2008) Cell Stem Cell 2, 230-240; Maherali, N., et al., (2008) Cell Stem Cell 3, 340-345). This robust increase in efficiency prompted experiments examining whether the Alk5 inhibitor could also reduce the temporal requirement of factor expression, thus reflecting an increase in the kinetics of reprogramming. To test this, doxycycline was applied for three, four, or five days on four-factor infected MEFs, either in the presence or absence of the Alk5 inhibitor (FIG. 2B). While iPSCs were not obtained with three days of dox treatment in either condition, four days of dox treatment was sufficient to give rise to iPSC colonies at a frequency of 0.0013% in the inhibitor-treated condition. These colonies were not immediately apparent and took at least one week after dox withdrawal to emerge. No colonies were observed in the control condition, demonstrating that the inhibitor promoted faster induction of iPSCs. 4-day iPSCs expressed the pluripotency markers Nanog, Oct4, and Sox2 (FIG. 2C), which was tested three passages after dox withdrawal to ensure a lack of residual transgene expression (Maherali, N., et al., (2008) Cell Stem Cell 3, 340-345). These cells were also competent to form lineages from all three germ layers in the context of a teratoma (FIG. 2C), providing a functional test of pluripotency and indicating that use of the Alk5 inhibitor during reprogramming has no adverse effect on the resulting iPSCs.

Figure 2E:
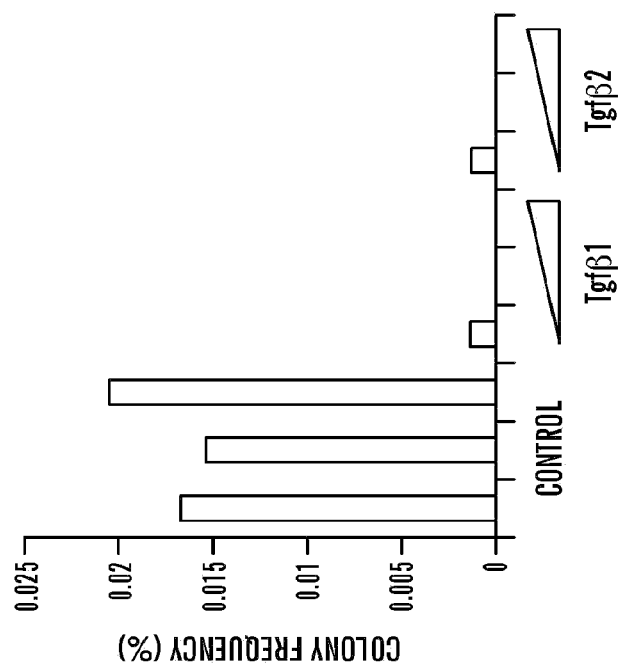
Figure 2D:
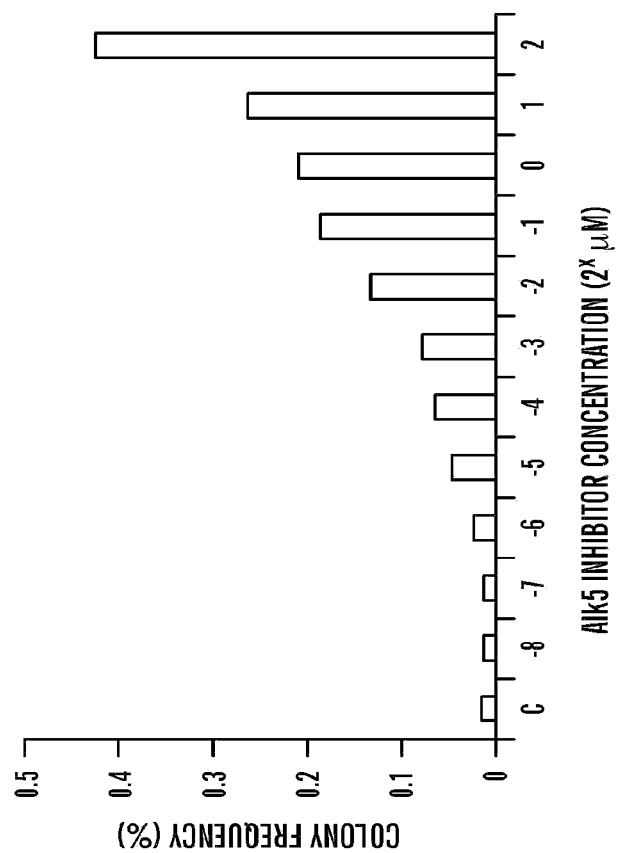
Figure 2G:
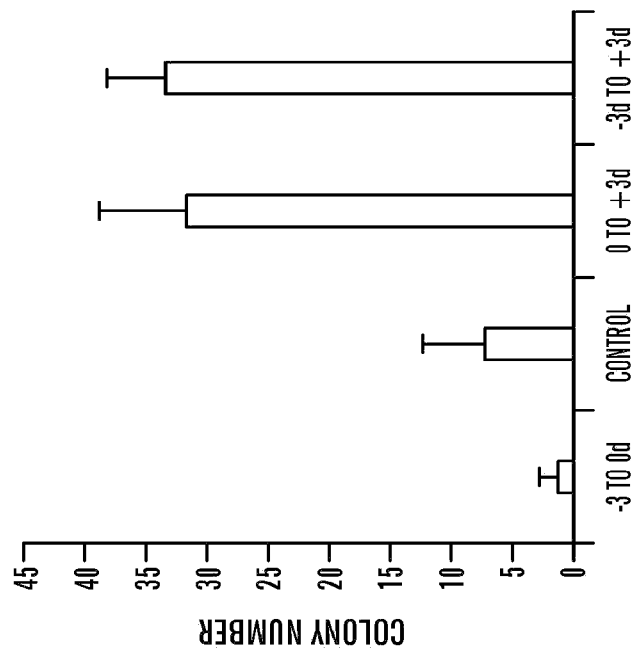

It was next sought to establish a dose-response curve for the Alk5 inhibitor. Using four-factor infected MEFs, concentrations of the Alk5 inhibitor were tested over a 1000-fold range, from 4 nM to 4 μM. Increasing concentrations of inhibitor led to a progressive increase in the number of iPSC colonies obtained, resulting in a 30-fold enhancement at the highest dose tested (FIG. 2D). To verify that manipulation of TGF-β signaling affects reprogramming, it was investigated whether pathway activation would inhibit iPSC formation. Using four-factor infected MEFs, increasing concentrations of TGF-β1 or TGF-β2 were applied during the time of dox induction. Under control conditions, an average of 14 colonies per well (~0.017%) were obtained; however, upon addition of 1 ng/mL TGF-β1 or TGF-β2, the efficiency was reduced to one colony per well (~0.0013%), and at 2.5 ng/mL and 5 ng/mL, iPSC formation was undetectable (FIG. 2E).

Figure 2F:
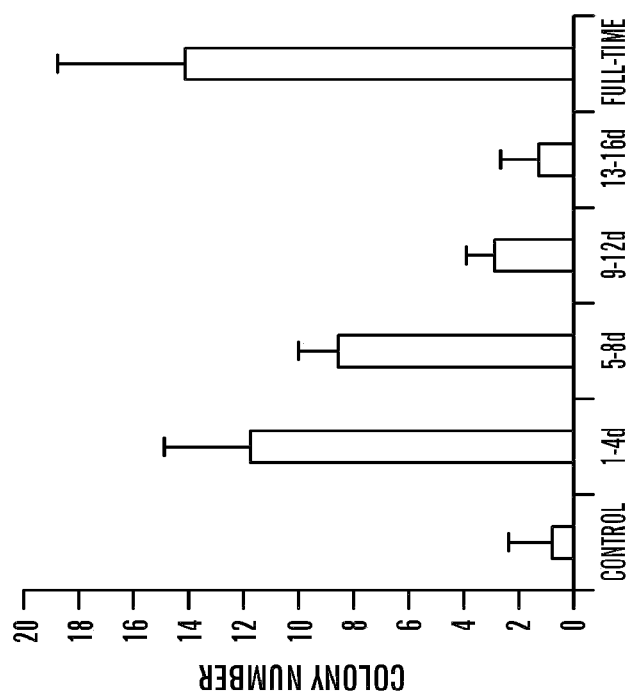

The opposing effects of pathway activation and inhibition confirm the involvement of TGF-β signaling in reprogramming. To gain further insight into the mode of action of the Alk5 inhibitor, the temporal window during which the inhibitor elicited its strongest effect was examined. In four-factor infected MEFs, the inhibitor was applied in 4-day intervals from days 0-16 of reprogramming. The largest increase in efficiency was observed during the first four days of reprogramming, yielding an increase comparable to full-time application of the inhibitor (FIG. 2F). A strong enhancement was also observed with application during the 5-8 day interval, while after dox withdrawal (day 12), the inhibitor appeared to have no effect. This early-acting effect prompted experiments to investigate whether the Alk5 inhibitor was acting to 'prime' the cells, thus altering or destabilizing the fibroblast state so that it is more amenable to reprogramming. To test this, the inhibitor was applied in 3-day time intervals: before dox administration (days −3 to 0) to test for a priming effect, during the first 3 days of reprogramming (days 0 to +3) as a control for the efficiency increase, during both intervals (days −3 to +3) to test for a synergistic effect, and a no-inhibitor control as a baseline measure (FIG. 1G).

Administration of the Alk5 inhibitor prior to expression of the reprogramming factors (days 3 to 0) led to a slight reduction in efficiency, thus arguing against a priming effect. In contrast, addition of the inhibitor during the first 3 days of factor expression led to −5-fold enhancement in efficiency, consistent with previous findings. The increase in efficiency seen in the −3d/+3d group was comparable to the 0 to +3d group, indicating a lack of a synergistic effect. It therefore appears that Alk5 inhibition must coincide with expression of the reprogramming factors in order to elicit its effect. One limitation of direct infection is that not every cell receives the full complement of reprogramming factors, and there is a large amount of heterogeneity in expression, as each cell harbors a unique pattern of viral insertions. It is therefore difficult to ascertain whether the increase in efficiency observed so far is due solely to a cooperative effect, where the inhibitor enhances efficiency in the presence of all four factors, or a replacement effect, where the inhibitor substitutes for specific reprogramming factors. To this end, we employed a "secondary system" consisting of MEFs isolated from iPSC-derived chimeras. These MEFs contain a homogenous set of inducible lentiviral integrations that were permissive for conversion into primary iPSCs; thus, the levels and stoichiometry of the re-expressed factors are unique to each MEF line (Maherali, N., et al., (2008) Cell Stem Cell 3, 340-345; Wernig, M., et al., (2008) Nat Biotechnol 26, 916-924).

Figure 3A:
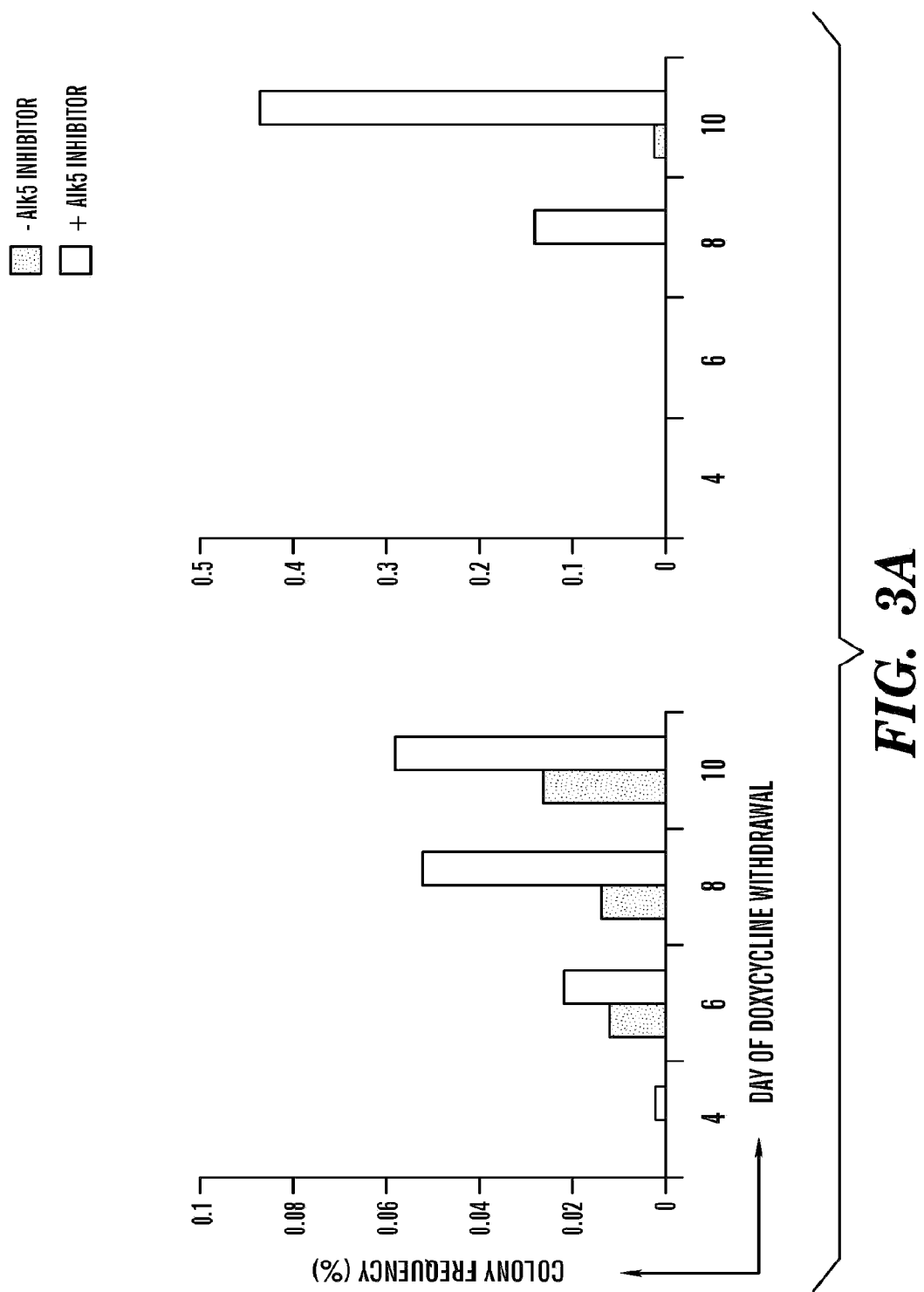
FIG. 3. An Alk5 Inhibitor Replaces the Individual Roles of cMyc and Sox2.
3A. Kinetics of reprogramming in two secondary MEF lines. Dox was applied for either 4, 6, 8, or 10 days, with or without the Alk5 inhibitor (2 µM). Colonies were quantified on day 16 based on morphology and dox independence.
3B. Dose-response curve for the Alk5 inhibitor in secondary STEMCCA MEFs. Dox and the inhibitor were applied for 8 days, and colonies were quantified on day 12 based on Oct4 immunostaining.
3C. Replacement of the role of cMyc with the Alk5 inhibitor (1 µM). MEFs were infected with either three (OSK) or four (OSMK) factors. Dox was withdrawn on day 8 and colonies were quantified on day 12 based on morphology and dox independence.
3D. Replacement of the role of Sox2 with the Alk5 inhibitor (1 µM). MEFs were infected with three (OMK) or two (OK) factors and induced with dox for 16 days, then split on day 18 into media without dox. Image depicts alkaline phosphatase stain of passage 1 cultures.

In two different secondary MEF lines, the effect of Alk5 inhibition on both the efficiency and kinetics of reprogramming was tested. In this experiment, dox was applied for 4, 6, 8, or 10 days, either in the presence or absence of the Alk5 inhibitor, then quantified iPSC colony number on day 16. The baseline levels of reprogramming differed between the two lines (FIG. 2A), which was not unexpected given that efficiency is dependent upon the levels and stoichiometry of factor expression as previously reported (Wernig, M., et al., (2008) Nat Biotechnol 26, 916-924). In both lines, addition of the Alk5 inhibitor mediated an increase in both efficiency and kinetics of reprogramming, consistent with a cooperative effect (FIG. 3A). However, the degree to which reprogramming was enhanced was different between the two lines, with one line showing a 2-fold increase and the other a 30-fold increase.

Without wishing to be bound by theory it was reasoned that a purely cooperative action would produce a consistent fold-increase between the different lines regardless of variation in factor expression levels, which was not the case. Thus, to further discern between a cooperative and a replacement effect, a polycistronic construct was employed that linked all four reprogramming factors on a single transcript ("STEM-CCA") (Sommer, C. A., et al., (2009) Stem Cells 27, 543-549), which in the context of a secondary system enables expression of all factors in >95% of cells (data not shown). In such a system, only a cooperative effect would be revealed, as co-expression of all factors precludes factor replacement.

Figures 3B, 3C:
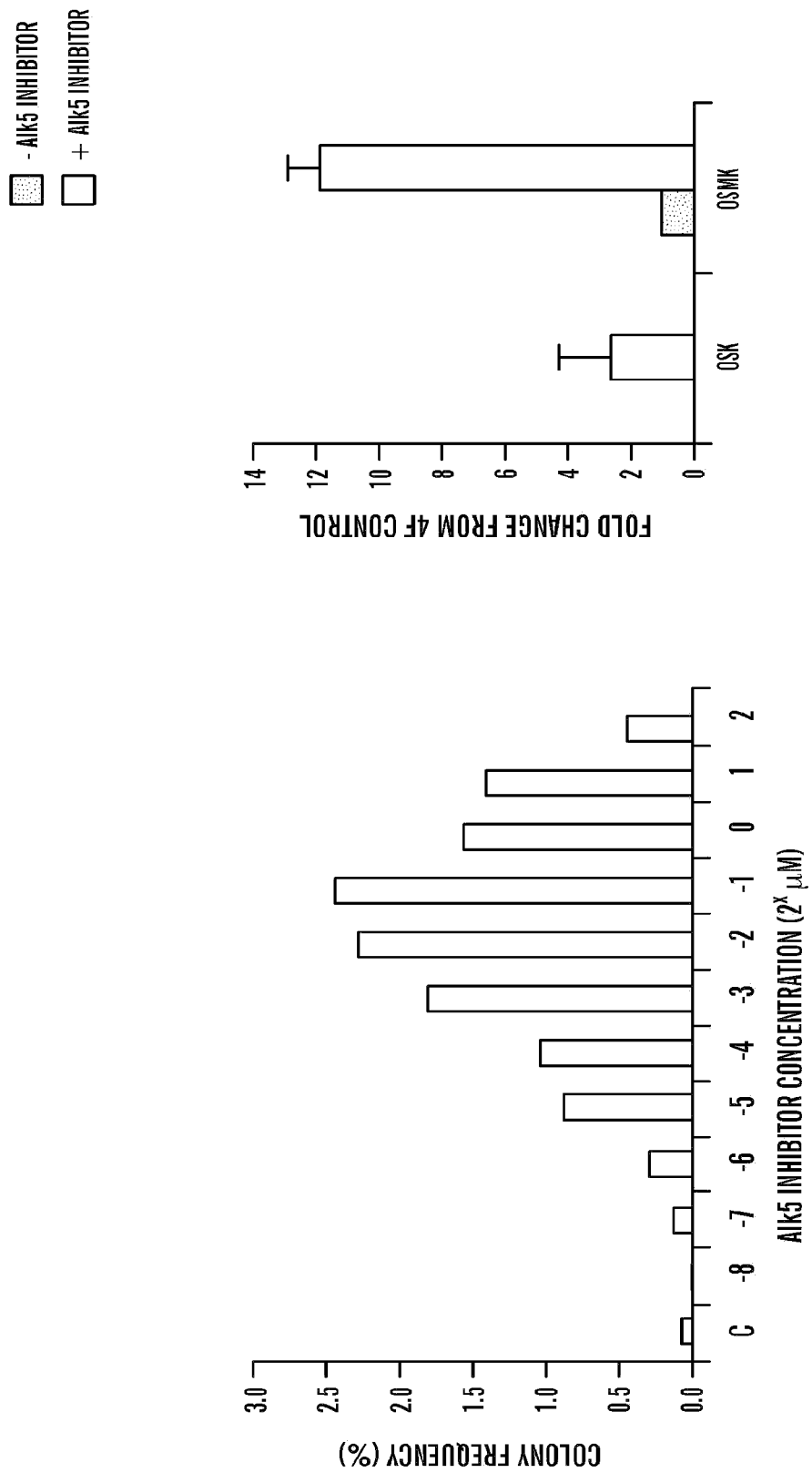

Secondary STEMCCA MEFs were used to establish another dose-response curve for the Alk5 inhibitor. In contrast to primary infected MEFs, which demonstrated a steady increase across the entire dose range tested (FIG. 2D), the STEMCCA MEFs reached a maximum efficiency at 0.5 µM, representing a ~60-fold increase, and began to decline at higher doses (FIG. 3B). A similar pattern was also observed with another inhibitor, SB-431542, that targets the type I Tgfβ receptors, Alk-4, -5, and -7 (FIG. 5). These data corroborate the notion of a cooperative effect and also introduce the possibility of a factor replacement effect that operates at a different dose range, thus explaining the persistent efficiency increase with higher doses of the Alk5 inhibitor in primary infected MEFs, yet a decline in the secondary STEMCCA MEFs.

Experiments were designed to investigate whether the Alk5 inhibitor could function to replace exogenous expression of any of the reprogramming factors. To this end, primary MEFs were infected with different combinations of the four factors in the presence or absence of inhibitor (FIG. 4) and then scored for iPSC formation. In the four-factor control infection (OSMK; O=Oct4, S=Sox2, M=cMyc, K=Klf4), colonies were already apparent after 6 days; dox was withdrawn on day 8 to avoid detrimental effects of prolonged factor expression (Mikkelsen, T. S., et al., (2008) Nature 454, 49-55). At this time colonies were observed in the cMyc replacement condition (OSK+inhibitor), but none without the inhibitor; thus, dox was withdrawn from these cultures on day 8 as well. Remarkably, use of the Alk5 inhibitor (OSK+inhibitor) in place of cMyc resulted in a 2.5-fold higher efficiency than with the four factors alone (OSK+M), indicating that Alk5 inhibition was more potent than the action of c-Myc in promoting reprogramming (FIG. 3C).

For all of the other replacement conditions, dox was withdrawn on day 16, which would provide sufficient time for reprogramming. While most conditions did not yield any obvious colonies, the Sox2 replacement condition contained numerous colonies morphologically similar to iPSCs. These colonies appeared late in reprogramming, becoming readily apparent after 14 days. Based on morphology, 50 colonies were observed in the inhibitor-treated culture and 4 colonies in the control condition that were identical to iPSCs (data not shown). Withdrawal of dox, however, led to regression of many colonies in both conditions, indicating that the cells were not independent of factor expression. Nonetheless, colonies were picked from both conditions and tested for their potential to form dox-independent lines. From the control condition, 0/4 were capable of expansion, indicating that infection with the three factors (OMK) was not sufficient to induce reprogramming, while in the inhibitor-treated culture, 3/22 colonies formed dox-independent iPSC lines, demonstrating successful replacement of Sox2. The efficiency of expansion was low compared to that of four-factor iPSC clones, where all picked colonies (6/6 in this set of experiments) were capable of forming stable dox-independent lines.

Figure 3E:
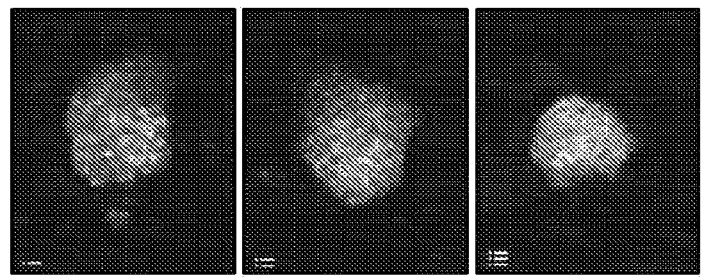
Figure 3D:
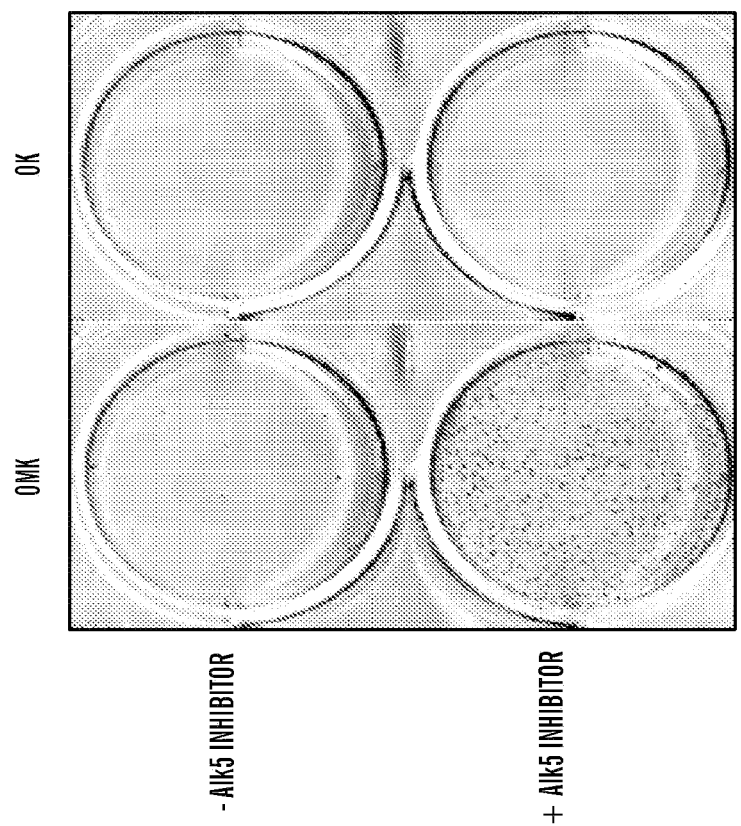
Figure 3G:
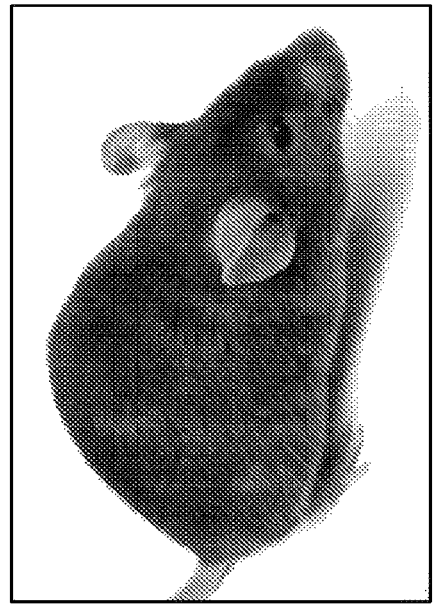
Figure 3F:
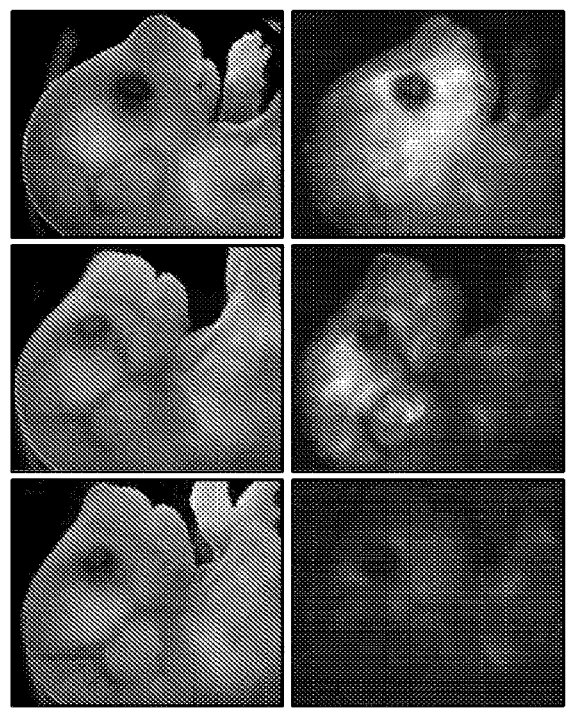
Figure 6B:
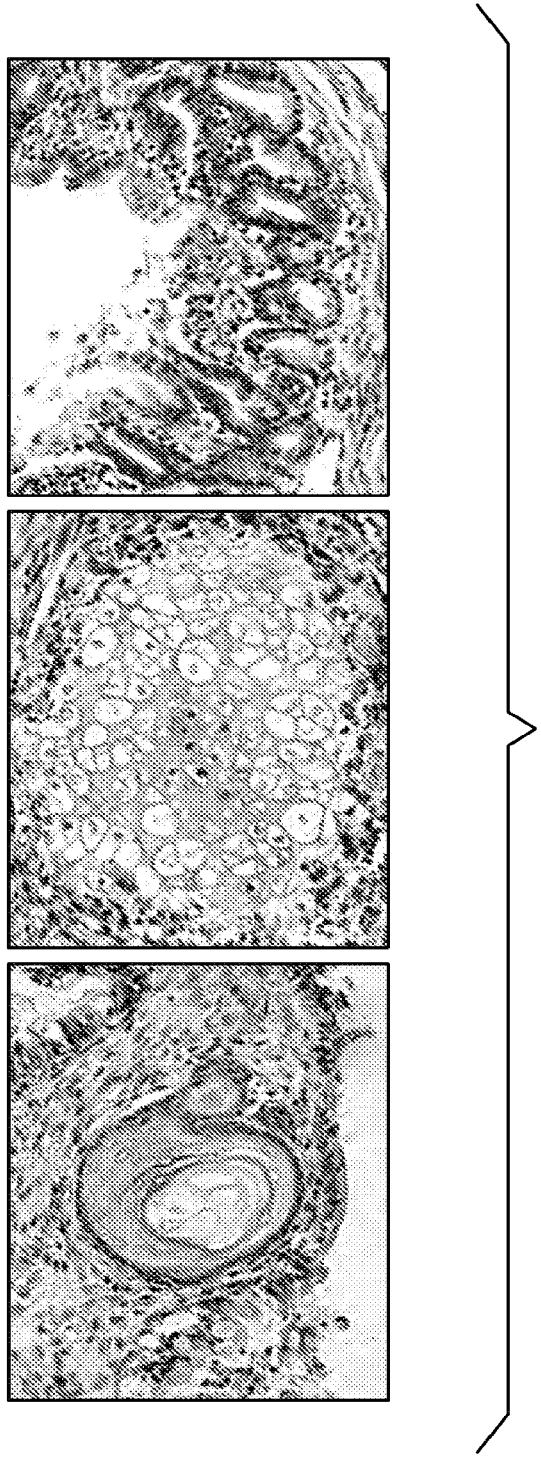

Immunostaining of the OMK+inhibitor iPSC lines demonstrated expression of Nanog, Oct4, and Sox2 (tested after three passages without dox) (FIG. 3E). To further verify expression of pluripotency genes, quantitative RT-PCR analysis was performed using primer sets that distinguish endogenous and viral transcripts (FIG. 6A), which revealed pluripotency gene activation and viral gene silencing. To functionally assess pluripotency of the OMK+inhibitor iPSCs, teratomas were generated, which contained lineages from all three germ layers (FIG. 6B). The ability of these cells to contribute to chimeric mice was tested; to this end, iPSCs were labeled with a lentivirus constitutively expressing the fluorescent protein, tdTomato, sorted the cells by flow cytometry, and injected them into blastocysts. Mice harvested on embryonic day E16.5 showed varying degrees of contribution (FIG. 3F).

Figure 6C:
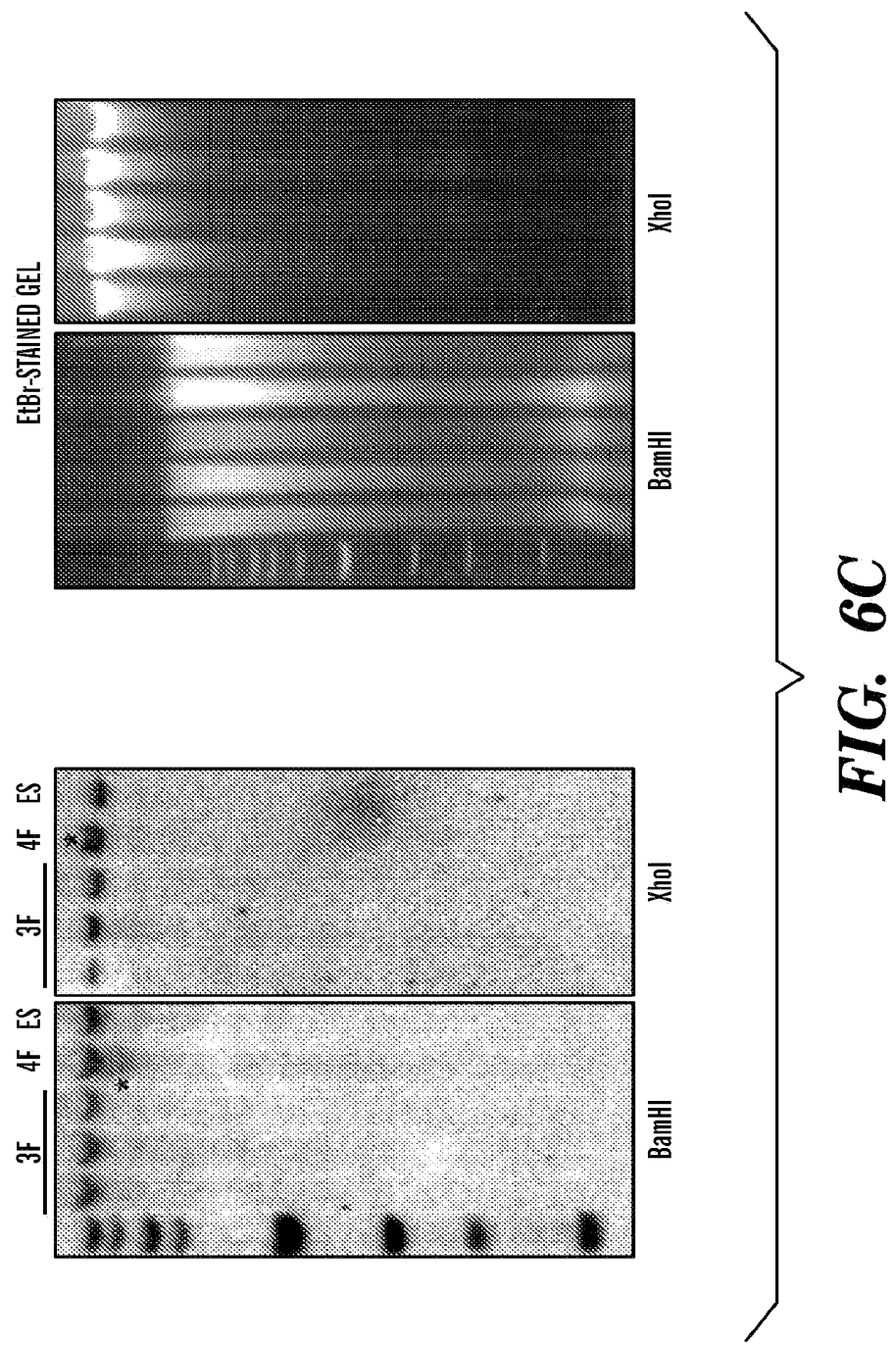

As a more stringent test of pluripotency, the cells were able to generate adult chimeras (FIG. 3G), though their potential for germline transmission has not yet been evaluated. To ensure that these iPSCs were free of Sox2 viral integrations, Southern blot analysis was performed using a Sox2 cDNA probe. No extraneous bands were observed in the OMK+ inhibitor lines, confirming the absence of exogenous Sox2 (FIG. 6C).

As a final test to determine whether the Alk5 inhibitor enabled iPSC formation under any of the replacement conditions, the primary cultures were passaged in the absence of dox, which permit the amplification and selection of dox-independent cells that may not have been visible in the initial culture. OSK and OSMK conditions were excluded since these readily formed iPSCs. Confirming the observations from the primary cultures, only the Sox2 replacement condition (OMK+inhibitor) gave rise to dox-independent colonies (FIG. 3D). The control condition (OMK−inhibitor) also contained colonies that expressed alkaline phosphatase (FIG. 3D, upper left); however, these colonies appeared fibroblastic and did not grow, indicating that they were not iPSCs. Interestingly, while the Alk5 inhibitor enabled colony formation in the absence of either cMyc or Sox2, colonies could not be obtained in the absence of both factors (OK; FIG. 3D), indicating that the inhibitor performs distinct functions from Sox2 and cMyc but can preferentially assume their role in the context of reprogramming with the three remaining factors.

The results presented here demonstrate that TGF-β receptor I kinase inhibition enhances both the efficiency and kinetics of reprogramming in a dose-dependent manner, while activation of the TGF-β signaling pathway blocks reprogramming. The Alk5 inhibitor exerts its strongest effect during the early stages of iPSC induction and acts in concert with the reprogramming factors to mediate its effect, rather than converting the fibroblasts to a state more amenable to reprogramming. In addition to its cooperative action, the Alk5 inhibitor can replace the individual roles of cMyc or Sox2, although it cannot replace them simultaneously. These results provide the first defined pathway that produces both a strong cooperative effect and can preferentially replace the roles of specific reprogramming factors.

Figure 7A:
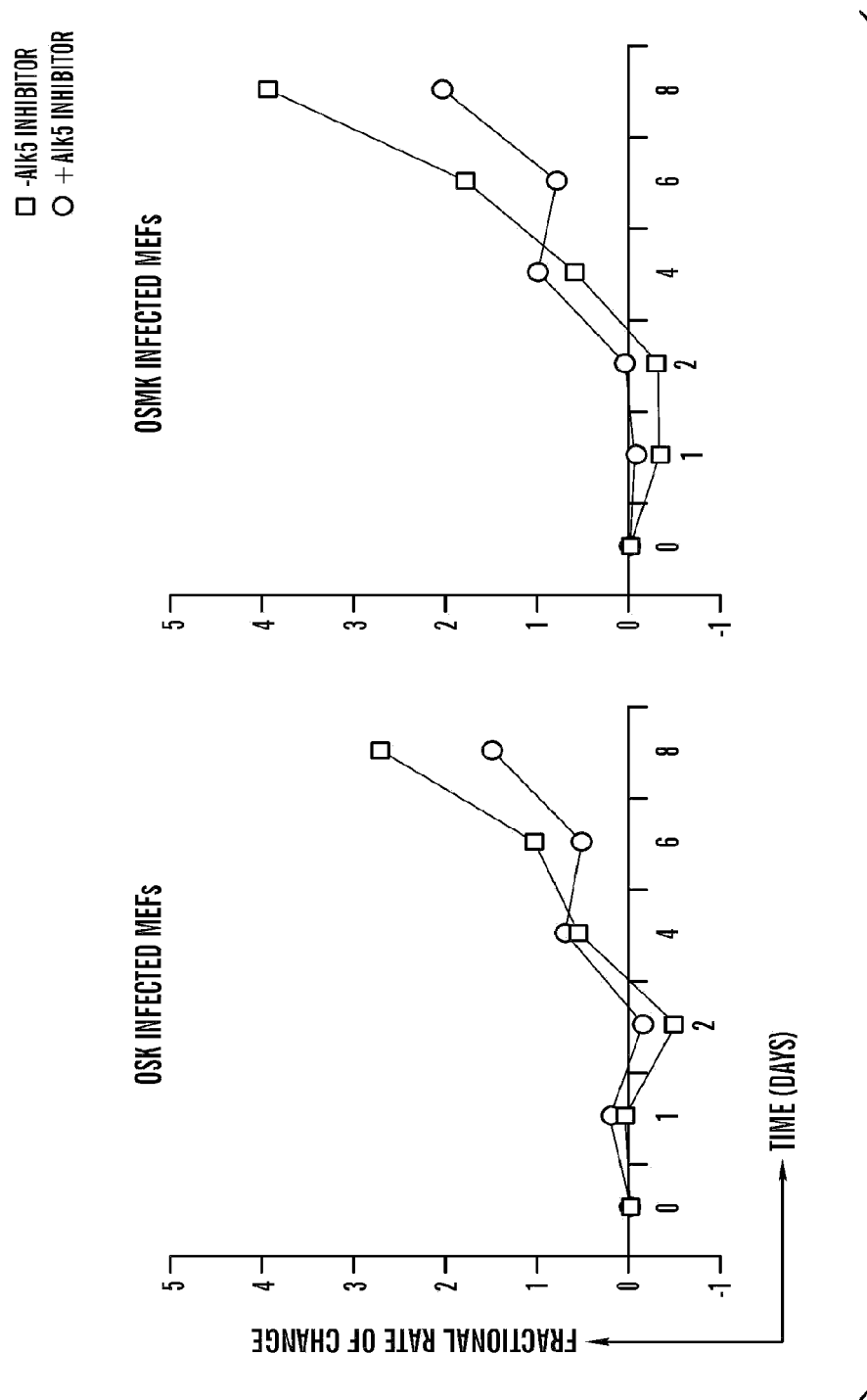
Figure 7B:
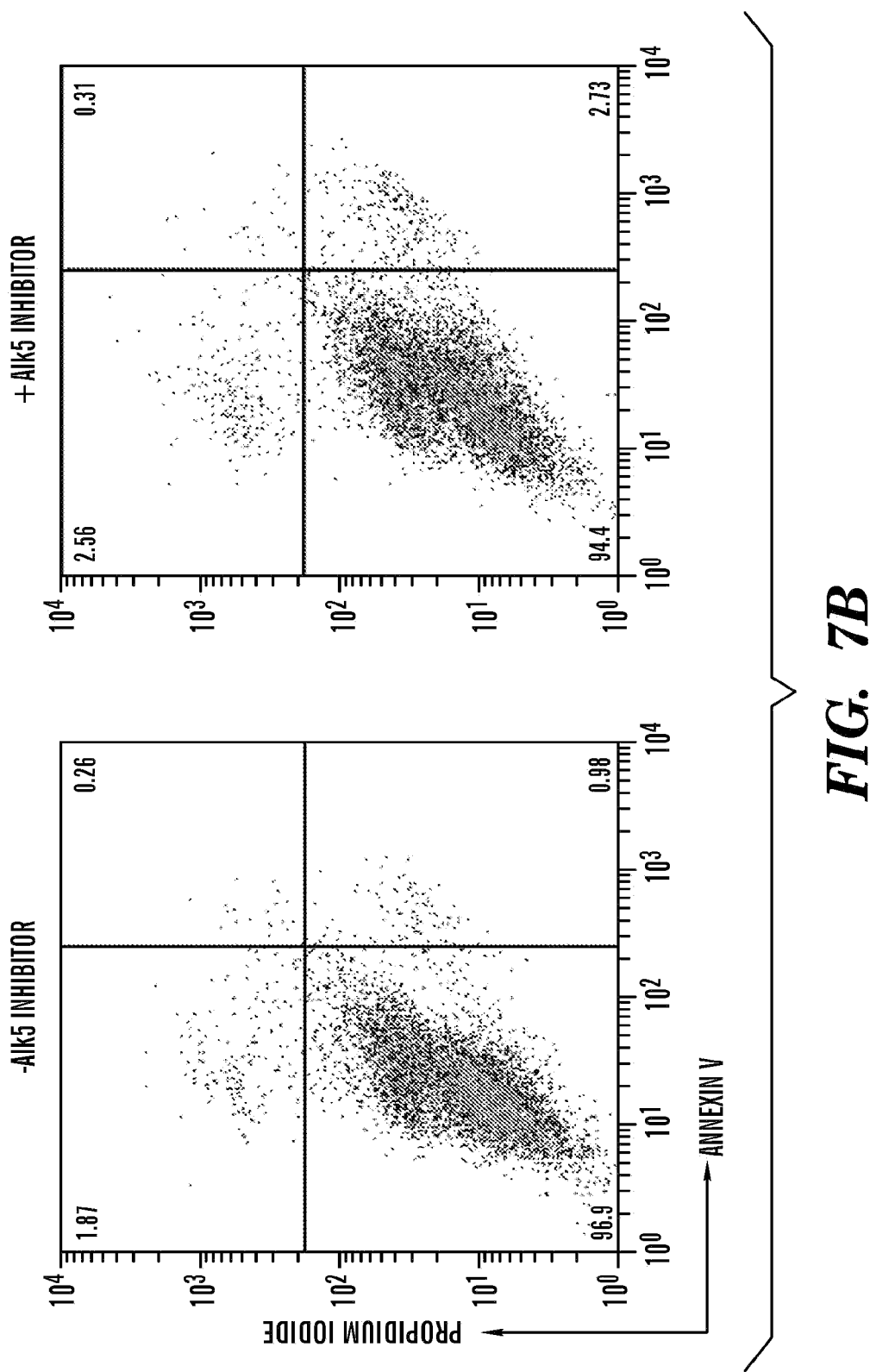

An important question that remains is how Alk5 inhibition acts on a molecular level to enhance reprogramming. It was observed that application of the inhibitor prior to factor expression was unable to mediate an increase in efficiency, indicative of a transient effect and/or one that is context-dependent, requiring expression of the reprogramming factors to carry out its role. The observation that the Alk5 inhibitor acts early in reprogramming raises the question of whether it helps shut down the fibroblast gene expression program. In support of this, it has been shown that activation of TGF-β signaling can promote an epithelial-to-mesenchymal transition (Valcourt, U., et al., (2005) *Mol Biol Cell* 16, 1987-2002); fibroblast reprogramming involves a mesenchymal-to-epithelial conversion, which may be enhanced by inhibition of the TGF-β signaling pathway. An enhancement in efficiency could also be mediated through increased proliferation. This possibility was tested by examining proliferation rates during reprogramming, but it was found that the inhibitor led to a decrease in proliferation around day 6 (FIG. 7A). It was noted that the inhibitor also mitigated the decrease in cell number that normally accompanies reprogramming (day 2) (FIG. 7A); however, the magnitude of this effect was unlikely to explain the large increase in overall reprogramming efficiency. Further, quantification of apoptosis with Annexin V staining showed a negligible difference between inhibitor-treated and untreated cells (FIG. 7B).

As yet another possibility, the Alk5 inhibitor was tested in the context of reprogramming by cell fusion (embryonic stem cells+MEFs), which led to a negative result (data not shown). This observation raises the question of whether Alk5 inhibition acts on pathways in direct reprogramming that are already operational in embryonic stem cells (ESCs), or whether the mechanisms of reprogramming by direct factors or cell fusion are fundamentally different. Without wishing to be bound by theory, the finding that the Alk5 inhibitor could replace either cMyc or Sox2, but not both together, indicates that its functions are distinct from these reprogramming factors. It is possible that replacement of both factors could occur with different doses of the inhibitor or with a longer period of dox administration; however, the conditions used that enabled replacement of the individual factors were unable to elicit simultaneous replacement, indicating a unique mode of action. It was tested whether the Alk5 inhibitor simply led to induction of Sox2 or cMyc expression; however, analysis by qRT-PCR revealed that only cMyc was significantly induced (1.3-fold) in OSK+inhibitor treated cells (FIG. 8), and there was no significant induction of Sox2 or cMyc in any of the other cells (OMK or OSMK). A possibility is that the Alk5 inhibitor acts on a pathway that completely bypasses the need for the individual reprogramming factors; for instance, it has been shown that Sox2 is not required for reprogramming by fusion of mESCs and human B lymphocytes (Pereira, C. F., et al., (2008) *PLoS Genet.* 4, e1000170).

Several TGF-β superfamily members represent important contributors to the pluripotent state. For instance, BMP4 signaling helps maintain mouse ESCs in an undifferentiated state (Ying, Q. L., et al., (2003) *Cell* 115, 281-292), and use of an Alk5 inhibitor in conjunction with GSK3β and MEK inhibitors facilitates rat and human iPSC line propagation and supports a mouse ESC-like phenotype (Li, W., et al., (2009) *Cell Stem Cell* 4, 16-19). In contrast to its pluripotency-promoting effect in mouse ESCs, BMP4 induces differentiation of human ESCs towards trophectoderm (Xu, R. H., et al., (2002) *Nat Biotechnol* 20, 1261-1264), while Activin signaling maintains pluripotency of hESCs (Xu, RE., et al., (2008) *Cell Stem Cell* 3, 196-206). The differential requirements of TGF-β signaling in mouse and human ESCs may explain why an increase in the efficiency of human fibroblast reprogramming was not observed (data not shown); it will be interesting to see whether activation of other pathways that promote the undifferentiated state also enhance reprogramming.

The highly characterized nature of the TGF-β signaling pathway makes it an attractive model for examining how interactions between downstream targets and the four factors synergize to enhance reprogramming. The identification of such pathways will greatly facilitate our understanding of reprogramming at the molecular level, potentially leading to the discovery of novel targets that promote reprogramming and are of therapeutic value.

Example 3

Exemplary Methods Useful for the Methods Described Herein

Virus Production

Vectors were constructed as previously described (Stadtfeld, M., et al., (2008) Cell Stem Cell 2, 230-240). For all experiments, cells were infected overnight at an MOI of 10 in the presence of polybrene 6 μg/mL, which was experimentally determined to infect >90% of cells.

Cell Culture and iPSC Induction

Cells were obtained from mice harboring a reverse tetracycline transactivator (rtTA) in the Rosa locus (Hochedlinger, K., et al. (2005) Cell 121, 465-477). Fibroblasts were derived from E14.5 mice; all experiments were conducted prior to passage 3. To induce reprogramming, cells were infected with the viral cocktail, then split two days later into ESC media (15% FBS, Invitrogen; 1000 U/mL LIF) with doxycycline (1 μg/mL). Fibroblast feeder cells were used only to maintain iPSC lines, not during reprogramming. The Alk5 inhibitor (Calbiochem/EMD 616452) was used at a concentration of 4 μM, unless otherwise noted. The Alk-4/5/7 inhibitor, SB-431542, was obtained from Sigma; TGF-β ligands were obtained from Peprotech (TGF-β1, 100-21; TGF-β2, 100-35).

Alkaline Phosphatase and Immunostaining

Alkaline phosphatase (AP) staining was done using an AP substrate kit according to manufacturer directions (VectorLabs, SK-5100). The following antibodies were used for immunostaining: α-Nanog (1:200, ab21603, Abeam), α-Oct4 (1:100sc-8628, Santa Cruz Biotech), α-Sox2 (1:200, AB5603, Millipore).

Quantitative RT-PCR

RNA was extracted by using a Qiagen RNeasy kit (74104), then converted to cDNA with the Superscript III First-Strand synthesis system (Invitrogen) using oligo-dT primers. qRT-PCRs were carried out using Brilliant II SYBR Green mix (Stratagene) and run on a Stratagene MXPro400. Reactions were carried out in duplicate with -RT controls, and data were analyzed using the delta-delta Ct method.

Apoptosis Assay

Annexin V and propidium iodide staining was done using the Annexin V-FITC kit (BD Pharmingen, 556547) according to manufacturer directions. Cells were analyzed by flow cytometry on a FACSCalibur (BD).

Teratomas

A 25 cm$^2$ equivalent of confluent iPSCs grown on feeders was harvested and injected subcutaneously into SCID mice. Teratomas were harvested 3 weeks later and stained with hematoxylin/eosin.

Blastocyst Injections

BDF1 females were superovulated with PMS and hCG, then mated with BDF1 males. Blastocysts were flushed from uterine horns on day 3.5, and 10-20 labelled iPSCs were injected per blastocyst. Swiss-webster mice were set up with vasectomized males and used as recipients for the injected blastocysts.

The invention claimed is:

1. A composition comprising a reprogrammed pluripotent cell comprising an exogenous Oct3/4, exogenous Sox2, and an inhibitor of TGFβ receptor activity.

2. The composition of claim 1, wherein said inhibitor of TGFβ receptor activity is selected from the group consisting of an antibody that inhibits TGFβ receptor activity, a small molecule that inhibits TGFβ receptor activity, and an RNA interference molecule that inhibits TGFβ receptor activity.

3. The composition of claim 2, wherein said small molecule that inhibits TGFβ receptor activity is selected from the group consisting of: 2-(3-(6-Methylpyridin-2-yl)-1H-pyrazol-4-yl)-1,5-naphthyridine; [3-(Pyridin-2-yl)-4-(4- quinoyl)]-1H-pyrazole; and 3-(6-Methylpyridin-2-yl)-4-(4-quinolyl)-1-phenylthiocarbamoyl-1H-pyrazole.

4. The composition of claim 1, wherein said exogenous Oct3/4 and said exogenous Sox2 are expressed from an expression vector.

5. The composition of claim 4, wherein the expression vector is present in a viral vector or a plasmid.

6. The composition of claim 1, wherein the reprogrammed pluripotent cell further comprises exogenous Klf4 and/or exogenous c-Myc.

7. The composition of claim 1, wherein the composition further comprises at least one agent that increases the efficiency of reprogramming.

8. The composition of claim 7, wherein the agent that increases the efficiency of reprogramming is selected from the group consisting of: soluble Wnt; Wnt conditioned media; a G9a histone methyltransferase; BIX-01294; a MEK inhibitor; PD0325901; a DNA methyltransferase inhibitor; a histone deacetylase (HDAC) inhibitor; valproic acid; 5'-azacytidine; dexamethasone; suberoylanilide; hydroxamic acid (SAHA); and trichostatin (TSA).

9. A composition comprising: a mammalian cell comprising ectopic Oct3/4 and ectopic Sox2 and an inhibitor of TGFβ receptor activity.

10. The composition of claim 9, wherein the mammalian cell further comprises an ectopically-introduced Klf4 and/or c-Myc.

11. The composition of claim 10, wherein said inhibitor of TGFβ receptor activity is selected from the group consisting of an antibody that inhibits TGFβ receptor activity, a small molecule that inhibits TGFβ receptor activity, and an RNA interference molecule that inhibits TGFβ receptor activity.

12. The composition of claim 11, wherein said small molecule that inhibits TGFβ receptor activity is selected from the group consisting of: 2-(3-(6-methylpyridin-2-yl)-1H-pyrazol-4-yl)-1,5-naphthyridine; [3-(Pyridin-2-yl)-4-(4-quinoyl)]-1H-pyrazole; and 3-(6-Methylpyridin-2-yl)-4-(4-quinolyl)-1-phenylthiocarbamoyl-1H-pyrazole.

* * * * *

SEQUENCE LISTING

```
<160> NUMBER OF SEQ ID NOS: 5

<210> SEQ ID NO 1
<211> LENGTH: 503
<212> TYPE: PRT
<213> ORGANISM: Homo sapiens

<400> SEQUENCE: 1

Met Glu Ala Ala Val Ala Ala Pro Arg Pro Arg Leu Leu Leu Leu Val
1               5                   10                  15

Leu Ala Ala Ala Ala Ala Ala Ala Ala Leu Leu Pro Gly Ala Thr
            20                  25                  30

Ala Leu Gln Cys Phe Cys His Leu Cys Thr Lys Asp Asn Phe Thr Cys
        35                  40                  45

Val Thr Asp Gly Leu Cys Phe Val Ser Val Thr Glu Thr Thr Asp Lys
    50                  55                  60

Val Ile His Asn Ser Met Cys Ile Ala Glu Ile Asp Leu Ile Pro Arg
65                  70                  75                  80

Asp Arg Pro Phe Val Cys Ala Pro Ser Ser Lys Thr Gly Ser Val Thr
                85                  90                  95

Thr Thr Tyr Cys Cys Asn Gln Asp His Cys Asn Lys Ile Glu Leu Pro
            100                 105                 110

Thr Thr Val Lys Ser Ser Pro Gly Leu Gly Pro Val Glu Leu Ala Ala
            115                 120                 125
```

```
Val Ile Ala Gly Pro Val Cys Phe Val Cys Ile Ser Leu Met Leu Met
130                 135                 140

Val Tyr Ile Cys His Asn Arg Thr Val Ile His His Arg Val Pro Asn
145                 150                 155                 160

Glu Glu Asp Pro Ser Leu Asp Arg Pro Phe Ile Ser Glu Gly Thr Thr
                165                 170                 175

Leu Lys Asp Leu Ile Tyr Asp Met Thr Thr Ser Gly Ser Gly Ser Gly
            180                 185                 190

Leu Pro Leu Leu Val Gln Arg Thr Ile Ala Arg Thr Ile Val Leu Gln
        195                 200                 205

Glu Ser Ile Gly Lys Gly Arg Phe Gly Glu Val Trp Arg Gly Lys Trp
210                 215                 220

Arg Gly Glu Glu Val Ala Val Lys Ile Phe Ser Ser Arg Glu Glu Arg
225                 230                 235                 240

Ser Trp Phe Arg Glu Ala Glu Ile Tyr Gln Thr Val Met Leu Arg His
                245                 250                 255

Glu Asn Ile Leu Gly Phe Ile Ala Ala Asp Asn Lys Asp Asn Gly Thr
            260                 265                 270

Trp Thr Gln Leu Trp Leu Val Ser Asp Tyr His Glu His Gly Ser Leu
        275                 280                 285

Phe Asp Tyr Leu Asn Arg Tyr Thr Val Thr Val Glu Gly Met Ile Lys
    290                 295                 300

Leu Ala Leu Ser Thr Ala Ser Gly Leu Ala His Leu His Met Glu Ile
305                 310                 315                 320

Val Gly Thr Gln Gly Lys Pro Ala Ile Ala His Arg Asp Leu Lys Ser
                325                 330                 335

Lys Asn Ile Leu Val Lys Lys Asn Gly Thr Cys Cys Ile Ala Asp Leu
            340                 345                 350

Gly Leu Ala Val Arg His Asp Ser Ala Thr Asp Thr Ile Asp Ile Ala
        355                 360                 365

Pro Asn His Arg Val Gly Thr Lys Arg Tyr Met Ala Pro Glu Val Leu
370                 375                 380

Asp Asp Ser Ile Asn Met Lys His Phe Glu Ser Phe Lys Arg Ala Asp
385                 390                 395                 400

Ile Tyr Ala Met Gly Leu Val Phe Trp Glu Ile Ala Arg Arg Cys Ser
                405                 410                 415

Ile Gly Gly Ile His Glu Asp Tyr Gln Leu Pro Tyr Tyr Asp Leu Val
            420                 425                 430

Pro Ser Asp Pro Ser Val Glu Met Arg Lys Val Val Cys Glu Gln
        435                 440                 445

Lys Leu Arg Pro Asn Ile Pro Asn Arg Trp Gln Ser Cys Glu Ala Leu
450                 455                 460

Arg Val Met Ala Lys Ile Met Arg Glu Cys Trp Tyr Ala Asn Gly Ala
465                 470                 475                 480

Ala Arg Leu Thr Ala Leu Arg Ile Lys Lys Thr Leu Ser Gln Leu Ser
                485                 490                 495

Gln Gln Glu Gly Ile Lys Met
            500
```

<210> SEQ ID NO 2
<211> LENGTH: 503
<212> TYPE: PRT
<213> ORGANISM: Homo sapiens

<400> SEQUENCE: 2

```
Met Glu Ala Ala Val Ala Ala Pro Arg Pro Arg Leu Leu Leu Val
1               5                   10                  15

Leu Ala Ala Ala Ala Ala Ala Ala Leu Leu Pro Gly Ala Thr
            20                  25              30

Ala Leu Gln Cys Phe Cys His Leu Cys Thr Lys Asp Asn Phe Thr Cys
        35              40              45

Val Thr Asp Gly Leu Cys Phe Val Ser Val Thr Glu Thr Thr Asp Lys
    50              55                  60

Val Ile His Asn Ser Met Cys Ile Ala Glu Ile Asp Leu Ile Pro Arg
65              70              75                  80

Asp Arg Pro Phe Val Cys Ala Pro Ser Ser Lys Thr Gly Ser Val Thr
                85                  90              95

Thr Thr Tyr Cys Cys Asn Gln Asp His Cys Asn Lys Ile Glu Leu Pro
            100             105             110

Thr Thr Val Lys Ser Ser Pro Gly Leu Gly Pro Val Glu Leu Ala Ala
            115             120             125

Val Ile Ala Gly Pro Val Cys Phe Val Cys Ile Ser Leu Met Leu Met
        130             135             140

Val Tyr Ile Cys His Asn Arg Thr Val Ile His His Arg Val Pro Asn
145             150             155             160

Glu Glu Asp Pro Ser Leu Asp Arg Pro Phe Ile Ser Glu Gly Thr Thr
                165             170             175

Leu Lys Asp Leu Ile Tyr Asp Met Thr Thr Ser Gly Ser Gly Ser Gly
            180             185             190

Leu Pro Leu Leu Val Gln Arg Thr Ile Ala Arg Thr Ile Val Leu Gln
        195             200             205

Glu Ser Ile Gly Lys Gly Arg Phe Gly Glu Val Trp Arg Gly Lys Trp
    210             215             220

Arg Gly Glu Glu Val Ala Val Lys Ile Phe Ser Ser Arg Glu Glu Arg
225             230             235             240

Ser Trp Phe Arg Glu Ala Glu Ile Tyr Gln Thr Val Met Leu Arg His
                245             250             255

Glu Asn Ile Leu Gly Phe Ile Ala Ala Asp Asn Lys Asp Asn Gly Thr
            260             265             270

Trp Thr Gln Leu Trp Leu Val Ser Asp Tyr His Glu His Gly Ser Leu
        275             280             285

Phe Asp Tyr Leu Asn Arg Tyr Thr Val Thr Val Glu Gly Met Ile Lys
    290             295             300

Leu Ala Leu Ser Thr Ala Ser Gly Leu Ala His Leu His Met Glu Ile
305             310             315             320

Val Gly Thr Gln Gly Lys Pro Ala Ile Ala His Arg Asp Leu Lys Ser
                325             330             335

Lys Asn Ile Leu Val Lys Lys Asn Gly Thr Cys Cys Ile Ala Asp Leu
            340             345             350

Gly Leu Ala Val Arg His Asp Ser Ala Thr Asp Thr Ile Asp Ile Ala
        355             360             365

Pro Asn His Arg Val Gly Thr Lys Arg Tyr Met Ala Pro Glu Val Leu
    370             375             380

Asp Asp Ser Ile Asn Met Lys His Phe Glu Ser Phe Lys Arg Ala Asp
385             390             395             400

Ile Tyr Ala Met Gly Leu Val Phe Trp Glu Ile Ala Arg Arg Cys Ser
                405             410             415

Ile Gly Gly Ile His Glu Asp Tyr Gln Leu Pro Tyr Tyr Asp Leu Val
            420             425             430
```

Pro Ser Asp Pro Ser Val Glu Glu Met Arg Lys Val Val Cys Glu Gln
            435                 440                 445

Lys Leu Arg Pro Asn Ile Pro Asn Arg Trp Gln Ser Cys Glu Ala Leu
450                 455                 460

Arg Val Met Ala Lys Ile Met Arg Glu Cys Trp Tyr Ala Asn Gly Ala
465                 470                 475                 480

Ala Arg Leu Thr Ala Leu Arg Ile Lys Lys Thr Leu Ser Gln Leu Ser
            485                 490                 495

Gln Gln Glu Gly Ile Lys Met
            500

<210> SEQ ID NO 3
<211> LENGTH: 426
<212> TYPE: PRT
<213> ORGANISM: Homo sapiens

<400> SEQUENCE: 3

Met Glu Ala Ala Val Ala Ala Pro Arg Pro Arg Leu Leu Leu Leu Val
1               5                   10                  15

Leu Ala Ala Ala Ala Ala Ala Ala Leu Leu Pro Gly Ala Thr
                20                  25                  30

Ala Leu Gln Cys Phe Cys His Leu Cys Thr Lys Asp Asn Phe Thr Cys
            35                  40                  45

Val Thr Asp Gly Leu Cys Phe Val Ser Val Thr Glu Thr Thr Asp Lys
    50                  55                  60

Val Ile His Asn Ser Met Cys Ile Ala Glu Ile Asp Leu Ile Pro Arg
65                  70                  75                  80

Asp Arg Pro Phe Val Cys Ala Pro Ser Ser Lys Thr Gly Ser Val Thr
                85                  90                  95

Thr Thr Tyr Cys Cys Asn Gln Asp His Cys Asn Lys Ile Glu Leu Pro
            100                 105                 110

Thr Thr Gly Leu Pro Leu Leu Val Gln Arg Thr Ile Ala Arg Thr Ile
        115                 120                 125

Val Leu Gln Glu Ser Ile Gly Lys Gly Arg Phe Gly Glu Val Trp Arg
    130                 135                 140

Gly Lys Trp Arg Gly Glu Glu Val Ala Val Lys Ile Phe Ser Ser Arg
145                 150                 155                 160

Glu Glu Arg Ser Trp Phe Arg Glu Ala Glu Ile Tyr Gln Thr Val Met
                165                 170                 175

Leu Arg His Glu Asn Ile Leu Gly Phe Ile Ala Ala Asp Asn Lys Asp
            180                 185                 190

Asn Gly Thr Trp Thr Gln Leu Trp Leu Val Ser Asp Tyr His Glu His
        195                 200                 205

Gly Ser Leu Phe Asp Tyr Leu Asn Arg Tyr Thr Val Thr Val Glu Gly
    210                 215                 220

Met Ile Lys Leu Ala Leu Ser Thr Ala Ser Gly Leu Ala His Leu His
225                 230                 235                 240

Met Glu Ile Val Gly Thr Gln Gly Lys Pro Ala Ile Ala His Arg Asp
                245                 250                 255

Leu Lys Ser Lys Asn Ile Leu Val Lys Lys Asn Gly Thr Cys Cys Ile
            260                 265                 270

Ala Asp Leu Gly Leu Ala Val Arg His Asp Ser Ala Thr Asp Thr Ile
        275                 280                 285

Asp Ile Ala Pro Asn His Arg Val Gly Thr Lys Arg Tyr Met Ala Pro
    290                 295                 300

```
Glu Val Leu Asp Asp Ser Ile Asn Met Lys His Phe Glu Ser Phe Lys
305                 310                 315                 320

Arg Ala Asp Ile Tyr Ala Met Gly Leu Val Phe Trp Glu Ile Ala Arg
                325                 330                 335

Arg Cys Ser Ile Gly Gly Ile His Glu Asp Tyr Gln Leu Pro Tyr Tyr
                340                 345                 350

Asp Leu Val Pro Ser Asp Pro Ser Val Glu Glu Met Arg Lys Val Val
                355                 360                 365

Cys Glu Gln Lys Leu Arg Pro Asn Ile Pro Asn Arg Trp Gln Ser Cys
                370                 375                 380

Glu Ala Leu Arg Val Met Ala Lys Ile Met Arg Glu Cys Trp Tyr Ala
385                 390                 395                 400

Asn Gly Ala Ala Arg Leu Thr Ala Leu Arg Ile Lys Lys Thr Leu Ser
                405                 410                 415

Gln Leu Ser Gln Gln Glu Gly Ile Lys Met
                420                 425

<210> SEQ ID NO 4
<211> LENGTH: 567
<212> TYPE: PRT
<213> ORGANISM: Homo sapiens

<400> SEQUENCE: 4

Met Gly Arg Gly Leu Leu Arg Gly Leu Trp Pro Leu His Ile Val Leu
1               5                   10                  15

Trp Thr Arg Ile Ala Ser Thr Ile Pro Pro His Val Gln Lys Ser Val
                20                  25                  30

Asn Asn Asp Met Ile Val Thr Asp Asn Asn Gly Ala Val Lys Phe Pro
                35                  40                  45

Gln Leu Cys Lys Phe Cys Asp Val Arg Phe Ser Thr Cys Asp Asn Gln
        50                  55                  60

Lys Ser Cys Met Ser Asn Cys Ser Ile Thr Ser Ile Cys Glu Lys Pro
65                  70                  75                  80

Gln Glu Val Cys Val Ala Val Trp Arg Lys Asn Asp Glu Asn Ile Thr
                85                  90                  95

Leu Glu Thr Val Cys His Asp Pro Lys Leu Pro Tyr His Asp Phe Ile
                100                 105                 110

Leu Glu Asp Ala Ala Ser Pro Lys Cys Ile Met Lys Glu Lys Lys Lys
                115                 120                 125

Pro Gly Glu Thr Phe Phe Met Cys Ser Cys Ser Ser Asp Glu Cys Asn
                130                 135                 140

Asp Asn Ile Ile Phe Ser Glu Glu Tyr Asn Thr Ser Asn Pro Asp Leu
145                 150                 155                 160

Leu Leu Val Ile Phe Gln Val Thr Gly Ile Ser Leu Leu Pro Pro Leu
                165                 170                 175

Gly Val Ala Ile Ser Val Ile Ile Ile Phe Tyr Cys Tyr Arg Val Asn
                180                 185                 190

Arg Gln Gln Lys Leu Ser Ser Thr Trp Glu Thr Gly Lys Thr Arg Lys
                195                 200                 205

Leu Met Glu Phe Ser Glu His Cys Ala Ile Ile Leu Glu Asp Asp Arg
                210                 215                 220

Ser Asp Ile Ser Ser Thr Cys Ala Asn Asn Ile Asn His Asn Thr Glu
225                 230                 235                 240

Leu Leu Pro Ile Glu Leu Asp Thr Leu Val Gly Lys Gly Arg Phe Ala
                245                 250                 255
```

```
Glu Val Tyr Lys Ala Lys Leu Lys Gln Asn Thr Ser Glu Gln Phe Glu
            260                 265                 270

Thr Val Ala Val Lys Ile Phe Pro Tyr Glu Glu Tyr Ala Ser Trp Lys
            275                 280                 285

Thr Glu Lys Asp Ile Phe Ser Asp Ile Asn Leu Lys His Glu Asn Ile
            290                 295                 300

Leu Gln Phe Leu Thr Ala Glu Arg Lys Thr Glu Leu Gly Lys Gln
305                 310                 315                 320

Tyr Trp Leu Ile Thr Ala Phe His Ala Lys Gly Asn Leu Gln Glu Tyr
            325                 330                 335

Leu Thr Arg His Val Ile Ser Trp Glu Asp Leu Arg Lys Leu Gly Ser
            340                 345                 350

Ser Leu Ala Arg Gly Ile Ala His Leu His Ser Asp His Thr Pro Cys
            355                 360                 365

Gly Arg Pro Lys Met Pro Ile Val His Arg Asp Leu Lys Ser Ser Asn
            370                 375                 380

Ile Leu Val Lys Asn Asp Leu Thr Cys Cys Leu Cys Asp Phe Gly Leu
385                 390                 395                 400

Ser Leu Arg Leu Asp Pro Thr Leu Ser Val Asp Asp Leu Ala Asn Ser
            405                 410                 415

Gly Gln Val Gly Thr Ala Arg Tyr Met Ala Pro Glu Val Leu Glu Ser
            420                 425                 430

Arg Met Asn Leu Glu Asn Val Glu Ser Phe Lys Gln Thr Asp Val Tyr
            435                 440                 445

Ser Met Ala Leu Val Leu Trp Glu Met Thr Ser Arg Cys Asn Ala Val
            450                 455                 460

Gly Glu Val Lys Asp Tyr Glu Pro Pro Phe Gly Ser Lys Val Arg Glu
465                 470                 475                 480

His Pro Cys Val Glu Ser Met Lys Asp Asn Val Leu Arg Asp Arg Gly
            485                 490                 495

Arg Pro Glu Ile Pro Ser Phe Trp Leu Asn His Gln Gly Ile Gln Met
            500                 505                 510

Val Cys Glu Thr Leu Thr Glu Cys Trp Asp His Asp Pro Glu Ala Arg
            515                 520                 525

Leu Thr Ala Gln Cys Val Ala Glu Arg Phe Ser Glu Leu Glu His Leu
            530                 535                 540

Asp Arg Leu Ser Gly Arg Ser Cys Ser Glu Glu Lys Ile Pro Glu Asp
545                 550                 555                 560

Gly Ser Leu Asn Thr Thr Lys
            565

<210> SEQ ID NO 5
<211> LENGTH: 850
<212> TYPE: PRT
<213> ORGANISM: Homo sapiens

<400> SEQUENCE: 5

Met Thr Ser His Tyr Val Ile Ala Ile Phe Ala Leu Met Ser Ser Cys
1               5                   10                  15

Leu Ala Thr Ala Gly Pro Glu Pro Gly Ala Leu Cys Glu Leu Ser Pro
            20                  25                  30

Val Ser Ala Ser His Pro Val Gln Ala Leu Met Glu Ser Phe Thr Val
            35                  40                  45

Leu Ser Gly Cys Ala Ser Arg Gly Thr Thr Gly Leu Pro Gln Glu Val
            50                  55                  60
```

-continued

His Val Leu Asn Leu Arg Thr Ala Gly Gln Gly Pro Gly Gln Leu Gln
65                  70                  75                  80

Arg Glu Val Thr Leu His Leu Asn Pro Ile Ser Ser Val His Ile His
                85                  90                  95

His Lys Ser Val Val Phe Leu Leu Asn Ser Pro His Pro Leu Val Trp
            100                 105                 110

His Leu Lys Thr Glu Arg Leu Ala Thr Gly Val Ser Arg Leu Phe Leu
            115                 120                 125

Val Ser Glu Gly Ser Val Val Gln Phe Ser Ser Ala Asn Phe Ser Leu
130                 135                 140

Thr Ala Glu Thr Glu Glu Arg Asn Phe Pro His Gly Asn Glu His Leu
145                 150                 155                 160

Leu Asn Trp Ala Arg Lys Glu Tyr Gly Ala Val Thr Ser Phe Thr Glu
                165                 170                 175

Leu Lys Ile Ala Arg Asn Ile Tyr Ile Lys Val Gly Glu Asp Gln Val
                180                 185                 190

Phe Pro Pro Lys Cys Asn Ile Gly Lys Asn Phe Leu Ser Leu Asn Tyr
            195                 200                 205

Leu Ala Glu Tyr Leu Gln Pro Lys Ala Ala Glu Gly Cys Val Met Ser
210                 215                 220

Ser Gln Pro Gln Asn Glu Glu Val His Ile Ile Glu Leu Ile Thr Pro
225                 230                 235                 240

Asn Ser Asn Pro Tyr Ser Ala Phe Gln Val Asp Ile Thr Ile Asp Ile
                245                 250                 255

Arg Pro Ser Gln Glu Asp Leu Glu Val Val Lys Asn Leu Ile Leu Ile
                260                 265                 270

Leu Lys Cys Lys Lys Ser Val Asn Trp Val Ile Lys Ser Phe Asp Val
            275                 280                 285

Lys Gly Ser Leu Lys Ile Ile Ala Pro Asn Ser Ile Gly Phe Gly Lys
290                 295                 300

Glu Ser Glu Arg Ser Met Thr Met Thr Lys Ser Ile Arg Asp Asp Ile
305                 310                 315                 320

Pro Ser Thr Gln Gly Asn Leu Val Lys Trp Ala Leu Asp Asn Gly Tyr
                325                 330                 335

Ser Pro Ile Thr Ser Tyr Thr Met Ala Pro Val Ala Asn Arg Phe His
                340                 345                 350

Leu Arg Leu Glu Asn Asn Glu Glu Met Gly Asp Glu Val His Thr
            355                 360                 365

Ile Pro Pro Glu Leu Arg Ile Leu Leu Asp Pro Gly Ala Leu Pro Ala
370                 375                 380

Leu Gln Asn Pro Pro Ile Arg Gly Gly Glu Gly Gln Asn Gly Gly Leu
385                 390                 395                 400

Pro Phe Pro Phe Pro Asp Ile Ser Arg Arg Val Trp Asn Glu Glu Gly
                405                 410                 415

Glu Asp Gly Leu Pro Arg Pro Lys Asp Pro Val Ile Pro Ser Ile Gln
            420                 425                 430

Leu Phe Pro Gly Leu Arg Glu Pro Glu Val Gln Gly Ser Val Asp
            435                 440                 445

Ile Ala Leu Ser Val Lys Cys Asp Asn Glu Lys Met Ile Val Ala Val
450                 455                 460

Glu Lys Asp Ser Phe Gln Ala Ser Gly Tyr Ser Gly Met Asp Val Thr
465                 470                 475                 480

Leu Leu Asp Pro Thr Cys Lys Ala Lys Met Asn Gly Thr His Phe Val

-continued

```
                      485                 490                 495
Leu Glu Ser Pro Leu Asn Gly Cys Gly Thr Arg Pro Arg Trp Ser Ala
            500                 505                 510

Leu Asp Gly Val Val Tyr Tyr Asn Ser Ile Val Ile Gln Val Pro Ala
            515                 520                 525

Leu Gly Asp Ser Ser Gly Trp Pro Asp Gly Tyr Glu Asp Leu Glu Ser
            530                 535                 540

Gly Asp Asn Gly Phe Pro Gly Asp Met Asp Glu Gly Asp Ala Ser Leu
545                 550                 555                 560

Phe Thr Arg Pro Glu Ile Val Val Phe Asn Cys Ser Leu Gln Gln Val
                565                 570                 575

Arg Asn Pro Ser Ser Phe Gln Glu Gln Pro His Gly Asn Ile Thr Phe
            580                 585                 590

Asn Met Glu Leu Tyr Asn Thr Asp Leu Phe Leu Val Pro Ser Gln Gly
            595                 600                 605

Val Phe Ser Val Pro Glu Asn Gly His Val Tyr Val Glu Val Ser Val
            610                 615                 620

Thr Lys Ala Glu Gln Glu Leu Gly Phe Ala Ile Gln Thr Cys Phe Ile
625                 630                 635                 640

Ser Pro Tyr Ser Asn Pro Asp Arg Met Ser His Tyr Thr Ile Ile Glu
                645                 650                 655

Asn Ile Cys Pro Lys Asp Glu Ser Val Lys Phe Tyr Ser Pro Lys Arg
                660                 665                 670

Val His Phe Pro Ile Pro Gln Ala Asp Met Asp Lys Lys Arg Phe Ser
                675                 680                 685

Phe Val Phe Lys Pro Val Phe Asn Thr Ser Leu Leu Phe Leu Gln Cys
            690                 695                 700

Glu Leu Thr Leu Cys Thr Lys Met Glu Lys His Pro Gln Lys Leu Pro
705                 710                 715                 720

Lys Cys Val Pro Pro Asp Glu Ala Cys Thr Ser Leu Asp Ala Ser Ile
                725                 730                 735

Ile Trp Ala Met Met Gln Asn Lys Lys Thr Phe Thr Lys Pro Leu Ala
                740                 745                 750

Val Ile His His Glu Ala Glu Ser Lys Glu Lys Gly Pro Ser Met Lys
            755                 760                 765

Glu Pro Asn Pro Ile Ser Pro Pro Ile Phe His Gly Leu Asp Thr Leu
            770                 775                 780

Thr Val Met Gly Ile Ala Phe Ala Ala Phe Val Ile Gly Ala Leu Leu
785                 790                 795                 800

Thr Gly Ala Leu Trp Tyr Ile Tyr Ser His Thr Gly Glu Thr Ala Gly
                805                 810                 815

Arg Gln Gln Val Pro Thr Ser Pro Pro Ala Ser Glu Asn Ser Ser Ala
            820                 825                 830

Ala His Ser Ile Gly Ser Thr Gln Ser Thr Pro Cys Ser Ser Ser Ser
            835                 840                 845

Thr Ala
    850
```